(12) United States Patent
Bathe et al.

(10) Patent No.: US 8,080,395 B2
(45) Date of Patent: Dec. 20, 2011

(54) ALLELES OF THE PRPD1 GENE FROM CORYNEFORM BACTERIA

(75) Inventors: Brigitte Bathe, Salzkotten (DE); Caroline Kreutzer, Oerlinghausen (DE); Georg Thierbach, Bielefeld (DE)

(73) Assignee: Evonik Degussa GmbH, Duesseldorf (DE)

( * ) Notice: Subject to any disclaimer, the term of this patent is extended or adjusted under 35 U.S.C. 154(b) by 0 days.

(21) Appl. No.: 13/009,051

(22) Filed: Jan. 19, 2011

(65) Prior Publication Data

US 2011/0171695 A1    Jul. 14, 2011

Related U.S. Application Data

(62) Division of application No. 11/923,942, filed on Oct. 25, 2007, now Pat. No. 7,893,231.

(30) Foreign Application Priority Data

Oct. 26, 2006  (DE) .......................... 10 2006 050 489

(51) Int. Cl.
| | |
|---|---|
| *C07H 21/02* | (2006.01) |
| *C12P 21/06* | (2006.01) |
| *C12P 21/04* | (2006.01) |
| *C12P 13/04* | (2006.01) |
| *C12N 1/20* | (2006.01) |
| *C12N 15/00* | (2006.01) |

(52) U.S. Cl. ................ 435/106; 435/252.3; 435/252.32; 435/252.8; 435/320.1; 435/69.1; 435/71.1; 536/23.1

(58) Field of Classification Search ........................ None
See application file for complete search history.

(56) References Cited

OTHER PUBLICATIONS

Claes et al. (Identification of Two prpDBC Gene Clusters in Corynebacterium glutamicum and Their Involvement in Propionate Degradation via the 2-Methylcitrate Cycle, Journal of Bacteriology, May 2002, p. 2728-2739 vol. 184, No. 10).*

* cited by examiner

*Primary Examiner* — Suzanne M Noakes
*Assistant Examiner* — Jae W Lee
(74) *Attorney, Agent, or Firm* — Oblon, Spivak, McClelland, Maier & Neustadt, L.L.P.

(57) ABSTRACT

An isolated mutant of coryneform bacteria comprising a gene encodes a polypeptide having 2-methylcitrate dehydratase activity, where the polypeptide comprises an amino acid sequence in which one of the proteinogenic amino acids except L-proline is present at position 272 or a corresponding or comparable position. In addition, an isolated polynucleotide encoding a polypeptide having 2-methylcitrate dehydratase enzymic activity, which comprises at position 272 of the amino acid sequence or a corresponding or comparable position a proteinogenic amino acid except L-proline is described. A method for producing a recombinant coryneform bacterium and L-amino acids. A recombinant microorganism, L-Lysine-containing feed additive, and L-Tryptophan-containing feed additive is also described.

25 Claims, 1 Drawing Sheet

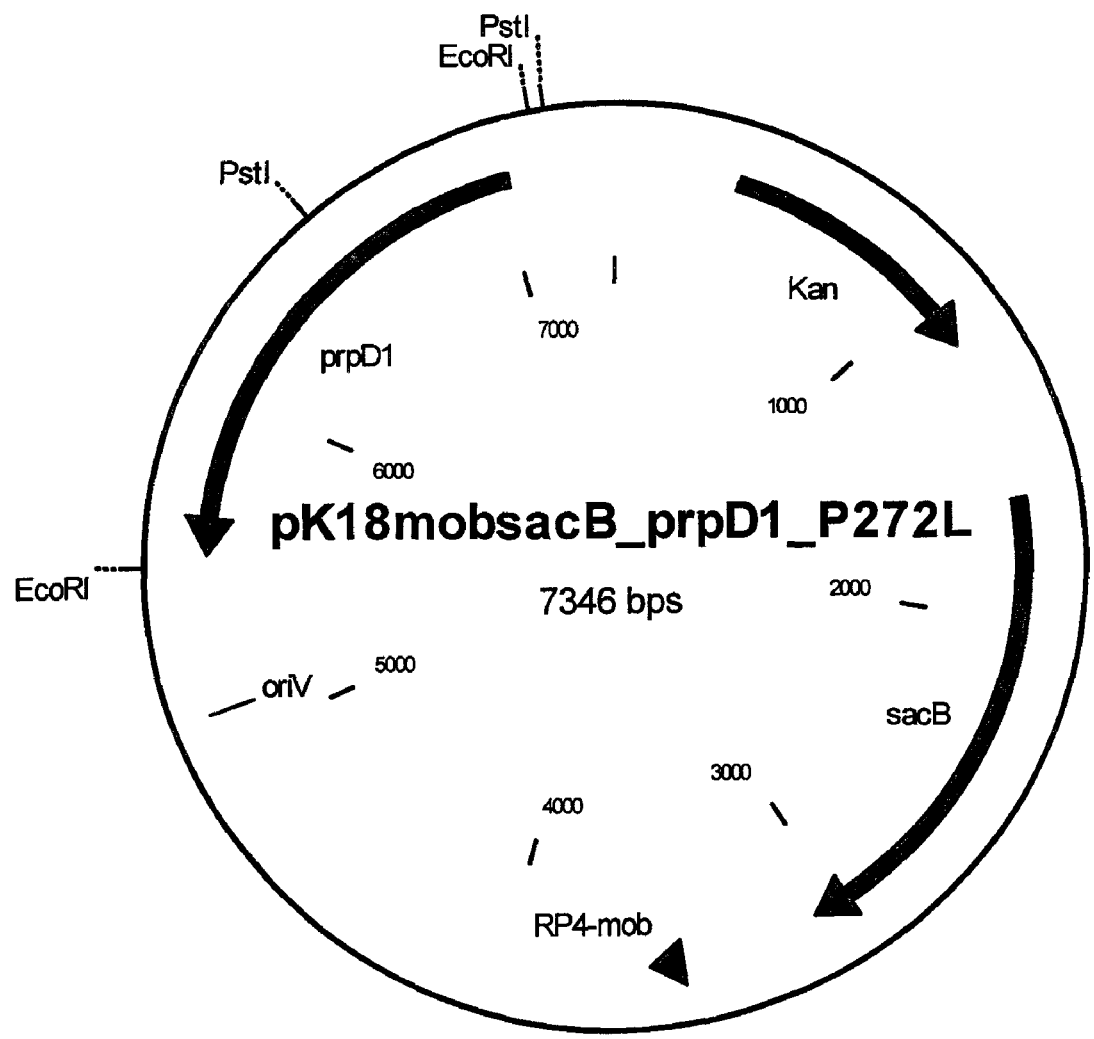

SEQUENCE LISTING

<160> NUMBER OF SEQ ID NOS: 23

<210> SEQ ID NO 1
<211> LENGTH: 1497
<212> TYPE: DNA
<213> ORGANISM: Corynebacterium glutamicum
<220> FEATURE:
<221> NAME/KEY: CDS
<222> LOCATION: (1)..(1494)
<223> OTHER INFORMATION: prpD1 wilde type gene coding region
<220> FEATURE:
<221> NAME/KEY: misc_feature
<222> LOCATION: (815)..(815)
<223> OTHER INFORMATION: Cytosin

<400> SEQUENCE: 1

| | | | | | | | | | | | | | | | | |
|---|---|---|---|---|---|---|---|---|---|---|---|---|---|---|---|---|
| atg | cgc | atc | cac | gat | gtt | tat | acc | cac | ctt | tcg | gcc | gat | aac | ttt | ccc | 48 |
| Met | Arg | Ile | His | Asp | Val | Tyr | Thr | His | Leu | Ser | Ala | Asp | Asn | Phe | Pro | |
| 1 | | | | 5 | | | | | 10 | | | | | 15 | | |
| aaa | gca | gag | cac | ctt | gcg | tgg | aaa | ttc | tcc | gag | ctt | gcc | acc | gac | ccc | 96 |
| Lys | Ala | Glu | His | Leu | Ala | Trp | Lys | Phe | Ser | Glu | Leu | Ala | Thr | Asp | Pro | |
| | | | 20 | | | | | 25 | | | | | 30 | | | |
| gtg | gag | gtg | aca | ccg | gat | gtt | tcg | gag | atg | atc | atc | aac | cgg | atc | atc | 144 |
| Val | Glu | Val | Thr | Pro | Asp | Val | Ser | Glu | Met | Ile | Ile | Asn | Arg | Ile | Ile | |
| | | | 35 | | | | | 40 | | | | | 45 | | | |
| gac | aac | gcg | gcg | gtg | tct | gcc | gcg | tcg | gtg | ttg | cgc | cgg | cct | gtg | act | 192 |
| Asp | Asn | Ala | Ala | Val | Ser | Ala | Ala | Ser | Val | Leu | Arg | Arg | Pro | Val | Thr | |
| | | 50 | | | | | 55 | | | | | 60 | | | | |
| gtg | gcc | agg | caa | caa | gcg | cag | tcc | cat | ccg | cgg | gaa | aag | ggc | gga | aaa | 240 |
| Val | Ala | Arg | Gln | Gln | Ala | Gln | Ser | His | Pro | Arg | Glu | Lys | Gly | Gly | Lys | |
| 65 | | | | | 70 | | | | | 75 | | | | | 80 | |
| gtt | ttt | gga | att | tca | ggc | agc | tac | tca | cca | gag | tgg | gct | gcc | ttt | gct | 288 |
| Val | Phe | Gly | Ile | Ser | Gly | Ser | Tyr | Ser | Pro | Glu | Trp | Ala | Ala | Phe | Ala | |
| | | | | 85 | | | | | 90 | | | | | 95 | | |
| aat | ggt | gtg | gcc | gta | cgt | gaa | ttg | gac | ttc | cac | gat | aca | ttt | tta | gca | 336 |
| Asn | Gly | Val | Ala | Val | Arg | Glu | Leu | Asp | Phe | His | Asp | Thr | Phe | Leu | Ala | |
| | | | 100 | | | | | 105 | | | | | 110 | | | |
| gct | gaa | tac | tcc | cat | ccc | ggc | gac | aat | att | cca | cca | ctt | ctt | gca | gta | 384 |
| Ala | Glu | Tyr | Ser | His | Pro | Gly | Asp | Asn | Ile | Pro | Pro | Leu | Leu | Ala | Val | |
| | | | 115 | | | | | 120 | | | | | 125 | | | |
| gcg | cag | gct | cag | aga | agc | agc | ggc | agg | gat | ctc | att | cgg | ggt | atc | gcc | 432 |
| Ala | Gln | Ala | Gln | Arg | Ser | Ser | Gly | Arg | Asp | Leu | Ile | Arg | Gly | Ile | Ala | |
| | | 130 | | | | | 135 | | | | | 140 | | | | |
| act | gcc | tat | gag | gtg | cag | gtg | gaa | ttg | gtg | agg | ggg | atc | tgc | ttg | cat | 480 |
| Thr | Ala | Tyr | Glu | Val | Gln | Val | Glu | Leu | Val | Arg | Gly | Ile | Cys | Leu | His | |
| 145 | | | | | 150 | | | | | 155 | | | | | 160 | |
| gag | cac | aaa | att | gat | cac | gta | gcc | cac | ctt | ggt | ccc | agc | gct | gca | gcg | 528 |
| Glu | His | Lys | Ile | Asp | His | Val | Ala | His | Leu | Gly | Pro | Ser | Ala | Ala | Ala | |
| | | | | 165 | | | | | 170 | | | | | 175 | | |
| ggt | ttg | ggc | acg | ttg | ttg | cat | gta | gat | gag | gaa | acc | atc | tac | cag | gcg | 576 |
| Gly | Leu | Gly | Thr | Leu | Leu | His | Val | Asp | Glu | Glu | Thr | Ile | Tyr | Gln | Ala | |
| | | | 180 | | | | | 185 | | | | | 190 | | | |
| atc | ggc | cag | gca | ttg | cac | acc | acg | acg | gct | acg | agg | cag | tcg | cga | aaa | 624 |
| Ile | Gly | Gln | Ala | Leu | His | Thr | Thr | Thr | Ala | Thr | Arg | Gln | Ser | Arg | Lys | |
| | | | 195 | | | | | 200 | | | | | 205 | | | |
| ggt | gag | att | tcc | agc | tgg | aag | gcg | ttc | gcg | cca | gcg | ttt | gcg | gga | aag | 672 |
| Gly | Glu | Ile | Ser | Ser | Trp | Lys | Ala | Phe | Ala | Pro | Ala | Phe | Ala | Gly | Lys | |
| | | 210 | | | | | 215 | | | | | 220 | | | | |
| atg | gcc | att | gag | gcg | atg | gat | cgt | gcg | atg | cgt | ggg | gag | ggt | tcg | ccc | 720 |
| Met | Ala | Ile | Glu | Ala | Met | Asp | Arg | Ala | Met | Arg | Gly | Glu | Gly | Ser | Pro | |
| 225 | | | | | 230 | | | | | 235 | | | | | 240 | |

```
gca ccg att tgg gag ggc gaa gac ggg gtc atc gcg tgg ctg tta tcg      768
Ala Pro Ile Trp Glu Gly Glu Asp Gly Val Ile Ala Trp Leu Leu Ser
            245                 250                 255 ggc aaa gat cat gtt tat cat gtg cca ttg ccg gaa cac ggc gag ccc      816
Gly Lys Asp His Val Tyr His Val Pro Leu Pro Glu His Gly Glu Pro
        260                 265                 270 aag ctg ggg att cta gag act tac aca aag gaa cat tca gcg gaa tat      864
Lys Leu Gly Ile Leu Glu Thr Tyr Thr Lys Glu His Ser Ala Glu Tyr
    275                 280                 285 caa tcg cag gca ccg att gat ctg gcg cgc agg atg aag cca ctg gtt      912
Gln Ser Gln Ala Pro Ile Asp Leu Ala Arg Arg Met Lys Pro Leu Val
290                 295                 300 gac gcg gct ggc gga acg gaa cac att gca gag att gtg ctg cgc acc      960
Asp Ala Ala Gly Gly Thr Glu His Ile Ala Glu Ile Val Leu Arg Thr
305                 310                 315                 320 agt cac cac acg cat tat gtg att ggc act ggg gcg aac gat ccg cag     1008
Ser His His Thr His Tyr Val Ile Gly Thr Gly Ala Asn Asp Pro Gln
                325                 330                 335 aag atg gat ccg cag gcc tcg cgt gaa acc ctg gat cat tcc atc atg     1056
Lys Met Asp Pro Gln Ala Ser Arg Glu Thr Leu Asp His Ser Ile Met
            340                 345                 350 tac att ttc gcc gtc gcg ctt caa gat ggc gtg tgg cac cac gag ttt     1104
Tyr Ile Phe Ala Val Ala Leu Gln Asp Gly Val Trp His His Glu Phe
        355                 360                 365 tcc tac acc cgc aag cgt tcc acc cgc ccg gaa act gtg gag ctg tgg     1152
Ser Tyr Thr Arg Lys Arg Ser Thr Arg Pro Glu Thr Val Glu Leu Trp
    370                 375                 380 cac aag att cgc acc gtg gag gat cct gaa tgg acg cgc cga tac cat     1200
His Lys Ile Arg Thr Val Glu Asp Pro Glu Trp Thr Arg Arg Tyr His
385                 390                 395                 400 tct gat gat cct gca aaa aag gcc ttt ggt gcg aaa gca gtg atc aca     1248
Ser Asp Asp Pro Ala Lys Lys Ala Phe Gly Ala Lys Ala Val Ile Thr
                405                 410                 415 atg gct gat ggc acc gtg att gag gat gaa ttg gct gtc gcg gat gcc     1296
Met Ala Asp Gly Thr Val Ile Glu Asp Glu Leu Ala Val Ala Asp Ala
            420                 425                 430 cac ccg ctg ggt gct cgg ccg ttt gcg cgg gag aat tac att gaa aaa     1344
His Pro Leu Gly Ala Arg Pro Phe Ala Arg Glu Asn Tyr Ile Glu Lys
        435                 440                 445 ttc cgc aca ctc gcg cag ggg att gtc att gat tca gaa cag gaa cgc     1392
Phe Arg Thr Leu Ala Gln Gly Ile Val Ile Asp Ser Glu Gln Glu Arg
    450                 455                 460 ttc ttg cat gcc gtg caa agc ctg cct gac ctg gat gat ctt gat cag     1440
Phe Leu His Ala Val Gln Ser Leu Pro Asp Leu Asp Asp Leu Asp Gln
465                 470                 475                 480 ctc aac atc gaa gtc gac ata agc aac cag gcc gcg acg aaa gcg ggg     1488
Leu Asn Ile Glu Val Asp Ile Ser Asn Gln Ala Ala Thr Lys Ala Gly
                485                 490                 495 ctg tta tga                                                         1497
Leu Leu <210> SEQ ID NO 2
<211> LENGTH: 498
<212> TYPE: PRT
<213> ORGANISM: Corynebacterium glutamicus

<400> SEQUENCE: 2

Met Arg Ile His Asp Val Tyr Thr His Leu Ser Ala Asp Asn Phe Pro
1               5                   10                  15

Lys Ala Glu His Leu Ala Trp Lys Phe Ser Glu Leu Ala Thr Asp Pro
            20                  25                  30
```

```
Val Glu Val Thr Pro Asp Val Ser Glu Met Ile Ile Asn Arg Ile Ile
         35                  40                  45
Asp Asn Ala Ala Val Ser Ala Ser Val Leu Arg Arg Pro Val Thr
 50                  55                  60
Val Ala Arg Gln Gln Ala Gln Ser His Pro Arg Glu Lys Gly Gly Lys
 65                  70                  75                  80
Val Phe Gly Ile Ser Gly Ser Tyr Ser Pro Glu Trp Ala Ala Phe Ala
                 85                  90                  95
Asn Gly Val Ala Val Arg Glu Leu Asp Phe His Asp Thr Phe Leu Ala
             100                 105                 110
Ala Glu Tyr Ser His Pro Gly Asp Asn Ile Pro Pro Leu Leu Ala Val
             115                 120                 125
Ala Gln Ala Gln Arg Ser Ser Gly Arg Asp Leu Ile Arg Gly Ile Ala
 130                 135                 140
Thr Ala Tyr Glu Val Gln Val Glu Leu Val Arg Gly Ile Cys Leu His
145                 150                 155                 160
Glu His Lys Ile Asp His Val Ala His Leu Gly Pro Ser Ala Ala Ala
                 165                 170                 175
Gly Leu Gly Thr Leu Leu His Val Asp Glu Thr Ile Tyr Gln Ala
             180                 185                 190
Ile Gly Gln Ala Leu His Thr Thr Thr Ala Thr Arg Gln Ser Arg Lys
             195                 200                 205
Gly Glu Ile Ser Ser Trp Lys Ala Phe Ala Pro Ala Phe Ala Gly Lys
             210                 215                 220
Met Ala Ile Glu Ala Met Asp Arg Ala Met Arg Gly Glu Gly Ser Pro
225                 230                 235                 240
Ala Pro Ile Trp Glu Gly Glu Asp Gly Val Ile Ala Trp Leu Leu Ser
                 245                 250                 255
Gly Lys Asp His Val Tyr His Val Pro Leu Pro Glu His Gly Glu Pro
             260                 265                 270
Lys Leu Gly Ile Leu Glu Thr Tyr Thr Lys Glu His Ser Ala Glu Tyr
             275                 280                 285
Gln Ser Gln Ala Pro Ile Asp Leu Ala Arg Arg Met Lys Pro Leu Val
 290                 295                 300
Asp Ala Ala Gly Gly Thr Glu His Ile Ala Glu Ile Val Leu Arg Thr
305                 310                 315                 320
Ser His His Thr His Tyr Val Ile Gly Thr Gly Ala Asn Asp Pro Gln
                 325                 330                 335
Lys Met Asp Pro Gln Ala Ser Arg Glu Thr Leu Asp His Ser Ile Met
             340                 345                 350
Tyr Ile Phe Ala Val Ala Leu Gln Asp Gly Val Trp His His Glu Phe
             355                 360                 365
Ser Tyr Thr Arg Lys Arg Ser Thr Arg Pro Glu Thr Val Glu Leu Trp
             370                 375                 380
His Lys Ile Arg Thr Val Glu Asp Pro Glu Trp Thr Arg Arg Tyr His
385                 390                 395                 400
Ser Asp Asp Pro Ala Lys Lys Ala Phe Gly Ala Lys Ala Val Ile Thr
                 405                 410                 415
Met Ala Asp Gly Thr Val Ile Glu Asp Glu Leu Ala Val Ala Asp Ala
             420                 425                 430
His Pro Leu Gly Ala Arg Pro Phe Ala Arg Glu Asn Tyr Ile Glu Lys
             435                 440                 445
Phe Arg Thr Leu Ala Gln Gly Ile Val Ile Asp Ser Glu Gln Glu Arg
```

```
            450                 455                 460
Phe Leu His Ala Val Gln Ser Leu Pro Asp Leu Asp Asp Leu Asp Gln
465                 470                 475                 480

Leu Asn Ile Glu Val Asp Ile Ser Asn Gln Ala Ala Thr Lys Ala Gly
            485                 490                 495

Leu Leu

<210> SEQ ID NO 3
<211> LENGTH: 3000
<212> TYPE: DNA
<213> ORGANISM: Corynebacterium glutamicum
<220> FEATURE:
<221> NAME/KEY: misc_feature
<222> LOCATION: (1)..(750)
<223> OTHER INFORMATION: sequence upstream of CDS sequence
<220> FEATURE:
<221> NAME/KEY: misc_feature
<222> LOCATION: (751)..(2244)
<223> OTHER INFORMATION: prpD1 wild type coding region
<220> FEATURE:
<221> NAME/KEY: misc_feature
<222> LOCATION: (1565)..(1565)
<223> OTHER INFORMATION: Cytosin
<220> FEATURE:
<221> NAME/KEY: misc_feature
<222> LOCATION: (2245)..(3000)
<223> OTHER INFORMATION: sequence downstream from CDS sequence

<400> SEQUENCE: 3
ggttccacct tcgccataac gcttgacgac gcctccctcc ttcactctcg gcgcatcatt      60
ttggcccacg gcgccgttga cgatctgcca gaggtagaag gactgtcaga tttttgggga     120
accaaagtgt tgcactgcgc ttactgccac ggctttgagg cccgcgattc tgaaatcgtc     180
gtggtgggta cctcgcccat ggctgcgcac caagcgttga tgttctcgca gttgtccaaa     240
actgtcagct tggtgggcac gatcgacatt gatgaacaaa ccagcgagag cctagatagt     300
gctggagtaa aagtgttggg caccaatgcg gtgcgcgtat ccgccgaagg tgatggcctg     360
tctgtggaac tgtccgaagg cgatcattta agctgcgaca acatcgtggt ggcatctcgt     420
ccactggtgg atggcacgct gtacacccaa cttggtggtc agatggaaga aaacccgatg     480
ggcaggttca ttccaggtac ccaaaccggg cgcactccta ttgaaggtgt gtgggctgcc     540
ggaaacgcgc aagctcccat ggcgatggtc tatggttccg ctgctcaagg cgtgatggct     600
ggagcagaga tcaactttga tctgatcctg gaagatattt ccgtggcaag cgcgcagagc     660
taaactgcgt gaggttgtgg cctgtcacac ataatcggcc tagggtggga ctttaaggaa     720
acagtgcaca aataaatctc aaggagcccc atgcgcatcc acgatgttta tacccacctt     780
tcggccgata actttcccaa agcagagcac cttgcgtgga aattctccga gcttgccacc     840
gaccccgtgg aggtgacacc ggatgtttcg gagatgatca tcaaccggat catcgacaac     900
gcggcggtgt ctgccgcgtc ggtgttgcgc cggcctgtga ctgtggccag caacaagcg      960 cagtcccatc cgcgggaaaa gggcggaaaa gttttggaa tttcaggcag ctactcacca     1020
gagtgggctg cctttgctaa tggtgtggcc gtacgtgaat tggacttcca cgatacattt     1080
ttagcagctg aatactccca tcccggcgac aatattccac cacttcttgc agtagcgcag     1140
gctcagagaa gcagcggcag ggatctcatt cggggtatcg ccactgccta tgaggtgcag     1200
gtggaattgg tgaggggat ctgcttgcat gagcacaaaa ttgatcacgt agcccacctt     1260
ggtcccagcg ctgcagcggg tttgggcacg ttgttgcatg tagatgagga aaccatctac     1320
caggcgatcg gccaggcatt gcacaccacg acggctacga ggcagtcgcg aaaaggtgag     1380
```

-continued

```
atttccagct ggaaggcgtt cgcgccagcg tttgcgggaa agatggccat tgaggcgatg    1440
gatcgtgcga tgcgtgggga gggttcgccc gcaccgattt ggagggcga agacggggtc    1500 atcgcgtggc tgttatcggg caaagatcat gtttatcatg tgccattgcc ggaacacggc    1560
gagcccaagc tggggattct agagacttac acaaaggaac attcagcgga atatcaatcg    1620
caggcaccga ttgatctggc gcgcaggatg aagccactgg ttgacgcggc tggcggaacg    1680
gaacacattg cagagattgt gctgcgcacc agtcaccaca cgcattatgt gattggcact    1740
ggggcgaacg atccgcagaa gatggatccg caggcctcgc gtgaaaccct ggatcattcc    1800
atcatgtaca ttttcgccgt cgcgcttcaa gatggcgtgt ggcaccacga gttttcctac    1860
acccgcaagc gttccacccg cccggaaact gtggagctgt ggcacaagat cgcaccgtg    1920 gaggatcctg aatggacgcg ccgataccat tctgatgatc ctgcaaaaaa ggcctttggt    1980
gcgaaagcag tgatcacaat ggctgatggc accgtgattg aggatgaatt ggctgtcgcg    2040
gatgcccacc cgctgggtgc tcggccgttt gcgcgggaga attacattga aaaattccgc    2100
acactcgcgc aggggattgt cattgattca gaacaggaac gcttcttgca tgccgtgcaa    2160
agcctgcctg acctggatga tcttgatcag ctcaacatcg aagtcgacat aagcaaccag    2220
gccgcgacga agcggggct gttatgaatc tcttttcgaa tggtgttgat gtggggaggc    2280
gtcgacaagc atttaaagcg gcactcgccg cactccacat cgcccggctg cccggcgcat    2340
tctcccctct gattgcgcgc tccatcgaag aagccggctt cgaaggcgtc tacgtttccg    2400
gcgccgtcat agctgctgac ctggcactac ccgatatcgg cttgacgacg ctgaccgaag    2460
tcgcccaccg cgcgcggcaa attgcgcgcg tcacagacct aggagtgctt gtcgacgccg    2520
acaccggctt tggcgaaccc atgtcggcc acgcaccgt cgccgaattg gaggacgccg    2580
gtgtggccgg atgccacctt gaagaccaag tcaacccaa acgttgcggg cacttggacg    2640
gcaaagaagt cgtgcgcaca gacgtgatgg ttcgacgcat cgcagccgcc gtctcggccc    2700
ggcgcgaccc gaactttgtc atctgcgccc gcaccgacgc cgctggagtg gaaggaatcg    2760
acgccgccat tgagcgcgcg aaagcctact tagatgcggg cgccgacatg atttcaccg    2820 aagccctcca cagcgaagcc gacttccgat acttccggca cgccatccct gatgccttgt    2880
tgctggcgaa tatgaccgaa tttggcaaaa cgacgctgct gtcagccgac gtgttggaag    2940
agattggcta caacgccgtg atctaccccg tgaccacgct gcgtattgcc atgggacaag    3000
```

<210> SEQ ID NO 4
<211> LENGTH: 498
<212> TYPE: PRT
<213> ORGANISM: Corynebacterium glutamicus

<400> SEQUENCE: 4

```
Met Arg Ile His Asp Val Tyr Thr His Leu Ser Ala Asp Asn Phe Pro
1               5                   10                  15

Lys Ala Glu His Leu Ala Trp Lys Phe Ser Glu Leu Ala Thr Asp Pro
            20                  25                  30

Val Glu Val Thr Pro Asp Val Ser Glu Met Ile Ile Asn Arg Ile Ile
        35                  40                  45

Asp Asn Ala Ala Val Ser Ala Ala Ser Val Leu Arg Arg Pro Val Thr
    50                  55                  60

Val Ala Arg Gln Gln Ala Gln Ser His Pro Arg Glu Lys Gly Gly Lys
65                  70                  75                  80

Val Phe Gly Ile Ser Gly Ser Tyr Ser Pro Glu Trp Ala Ala Phe Ala
                85                  90                  95
```

```
Asn Gly Val Ala Val Arg Glu Leu Asp Phe His Asp Thr Phe Leu Ala
            100                 105                 110

Ala Glu Tyr Ser His Pro Gly Asp Asn Ile Pro Pro Leu Leu Ala Val
        115                 120                 125

Ala Gln Ala Gln Arg Ser Ser Gly Arg Asp Leu Ile Arg Gly Ile Ala
    130                 135                 140

Thr Ala Tyr Glu Val Gln Val Glu Leu Val Arg Gly Ile Cys Leu His
145                 150                 155                 160

Glu His Lys Ile Asp His Val Ala His Leu Gly Pro Ser Ala Ala Ala
                165                 170                 175

Gly Leu Gly Thr Leu Leu His Val Asp Glu Thr Ile Tyr Gln Ala
            180                 185                 190

Ile Gly Gln Ala Leu His Thr Thr Thr Ala Thr Arg Gln Ser Arg Lys
        195                 200                 205

Gly Glu Ile Ser Ser Trp Lys Ala Phe Ala Pro Ala Phe Ala Gly Lys
    210                 215                 220

Met Ala Ile Glu Ala Met Asp Arg Ala Met Arg Gly Glu Gly Ser Pro
225                 230                 235                 240

Ala Pro Ile Trp Glu Gly Glu Asp Gly Val Ile Ala Trp Leu Leu Ser
                245                 250                 255

Gly Lys Asp His Val Tyr His Val Pro Leu Pro Glu His Gly Glu Pro
            260                 265                 270

Lys Leu Gly Ile Leu Glu Thr Tyr Thr Lys Glu His Ser Ala Glu Tyr
        275                 280                 285

Gln Ser Gln Ala Pro Ile Asp Leu Ala Arg Arg Met Lys Pro Leu Val
    290                 295                 300

Asp Ala Ala Gly Gly Thr Glu His Ile Ala Glu Ile Val Leu Arg Thr
305                 310                 315                 320

Ser His His Thr His Tyr Val Ile Gly Thr Gly Ala Asn Asp Pro Gln
                325                 330                 335

Lys Met Asp Pro Gln Ala Ser Arg Glu Thr Leu Asp His Ser Ile Met
            340                 345                 350

Tyr Ile Phe Ala Val Ala Leu Gln Asp Gly Val Trp His His Glu Phe
        355                 360                 365

Ser Tyr Thr Arg Lys Arg Ser Thr Arg Pro Glu Thr Val Glu Leu Trp
    370                 375                 380

His Lys Ile Arg Thr Val Glu Asp Pro Glu Trp Thr Arg Arg Tyr His
385                 390                 395                 400

Ser Asp Asp Pro Ala Lys Lys Ala Phe Gly Ala Lys Ala Val Ile Thr
                405                 410                 415

Met Ala Asp Gly Thr Val Ile Glu Asp Glu Leu Ala Val Ala Asp Ala
            420                 425                 430

His Pro Leu Gly Ala Arg Pro Phe Ala Arg Glu Asn Tyr Ile Glu Lys
        435                 440                 445

Phe Arg Thr Leu Ala Gln Gly Ile Val Ile Asp Ser Glu Gln Glu Arg
    450                 455                 460

Phe Leu His Ala Val Gln Ser Leu Pro Asp Leu Asp Asp Leu Asp Gln
465                 470                 475                 480

Leu Asn Ile Glu Val Asp Ile Ser Asn Gln Ala Ala Thr Lys Ala Gly
                485                 490                 495

Leu Leu

<210> SEQ ID NO 5
<211> LENGTH: 1497
```

```
<212> TYPE: DNA
<213> ORGANISM: Corynebacterium glutamicum
<220> FEATURE:
<221> NAME/KEY: CDS
<222> LOCATION: (1)..(1494)
<223> OTHER INFORMATION: prpD1 allele
<220> FEATURE:
<221> NAME/KEY: misc_feature
<222> LOCATION: (815)..(815)
<223> OTHER INFORMATION: C to T translation

<400> SEQUENCE: 5 atg cgc atc cac gat gtt tat acc cac ctt tcg gcc gat aac ttt ccc      48
Met Arg Ile His Asp Val Tyr Thr His Leu Ser Ala Asp Asn Phe Pro
1               5                   10                  15 aaa gca gag cac ctt gcg tgg aaa ttc tcc gag ctt gcc acc gac ccc      96
Lys Ala Glu His Leu Ala Trp Lys Phe Ser Glu Leu Ala Thr Asp Pro
            20                  25                  30 gtg gag gtg aca ccg gat gtt tcg gag atg atc atc aac cgg atc atc     144
Val Glu Val Thr Pro Asp Val Ser Glu Met Ile Ile Asn Arg Ile Ile
        35                  40                  45 gac aac gcg gcg gtg tct gcc gcg tcg gtg ttg cgc cgg cct gtg act     192
Asp Asn Ala Ala Val Ser Ala Ala Ser Val Leu Arg Arg Pro Val Thr
    50                  55                  60 gtg gcc agg caa caa gcg cag tcc cat ccg cgg gaa aag ggc gga aaa     240
Val Ala Arg Gln Gln Ala Gln Ser His Pro Arg Glu Lys Gly Gly Lys
65                  70                  75                  80 gtt ttt gga att tca ggc agc tac tca cca gag tgg gct gcc ttt gct     288
Val Phe Gly Ile Ser Gly Ser Tyr Ser Pro Glu Trp Ala Ala Phe Ala
                85                  90                  95 aat ggt gtg gcc gta cgt gaa ttg gac ttc cac gat aca ttt tta gca     336
Asn Gly Val Ala Val Arg Glu Leu Asp Phe His Asp Thr Phe Leu Ala
            100                 105                 110 gct gaa tac tcc cat ccc ggc gac aat att cca cca ctt ctt gca gta     384
Ala Glu Tyr Ser His Pro Gly Asp Asn Ile Pro Pro Leu Leu Ala Val
        115                 120                 125 gcg cag gct cag aga agc agc ggc agg gat ctc att cgg ggt atc gcc     432
Ala Gln Ala Gln Arg Ser Ser Gly Arg Asp Leu Ile Arg Gly Ile Ala
    130                 135                 140 act gcc tat gag gtg cag gtg gaa ttg gtg agg ggg atc tgc ttg cat     480
Thr Ala Tyr Glu Val Gln Val Glu Leu Val Arg Gly Ile Cys Leu His
145                 150                 155                 160 gag cac aaa att gat cac gta gcc cac ctt ggt ccc agc gct gca gcg     528
Glu His Lys Ile Asp His Val Ala His Leu Gly Pro Ser Ala Ala Ala
                165                 170                 175 ggt ttg ggc acg ttg ttg cat gta gat gag gaa acc atc tac cag gcg     576
Gly Leu Gly Thr Leu Leu His Val Asp Glu Glu Thr Ile Tyr Gln Ala
            180                 185                 190 atc ggc cag gca ttg cac acc acg acg gct acg agg cag tcg cga aaa     624
Ile Gly Gln Ala Leu His Thr Thr Thr Ala Thr Arg Gln Ser Arg Lys
        195                 200                 205 ggt gag att tcc agc tgg aag gcg ttc gcg cca gcg ttt gcg gga aag     672
Gly Glu Ile Ser Ser Trp Lys Ala Phe Ala Pro Ala Phe Ala Gly Lys
    210                 215                 220 atg gcc att gag gcg atg gat cgt gcg atg cgt ggg gag ggt tcg ccc     720
Met Ala Ile Glu Ala Met Asp Arg Ala Met Arg Gly Glu Gly Ser Pro
225                 230                 235                 240 gca ccg att tgg gag ggc gaa gac ggg gtc atc gcg tgg ctg tta tcg     768
Ala Pro Ile Trp Glu Gly Glu Asp Gly Val Ile Ala Trp Leu Leu Ser
                245                 250                 255 ggc aaa gat cat gtt tat cat gtg cca ttg ccg gaa cac ggc gag ctc     816
Gly Lys Asp His Val Tyr His Val Pro Leu Pro Glu His Gly Glu Leu
            260                 265                 270
```

```
aag ctg ggg att cta gag act tac aca aag gaa cat tca gcg gaa tat         864
Lys Leu Gly Ile Leu Glu Thr Tyr Thr Lys Glu His Ser Ala Glu Tyr
            275                 280                 285 caa tcg cag gca ccg att gat ctg gcg cgc agg atg aag cca ctg gtt         912
Gln Ser Gln Ala Pro Ile Asp Leu Ala Arg Arg Met Lys Pro Leu Val
        290                 295                 300 gac gcg gct ggc gga acg gaa cac att gca gag att gtg ctg cgc acc         960
Asp Ala Ala Gly Gly Thr Glu His Ile Ala Glu Ile Val Leu Arg Thr
305                 310                 315                 320 agt cac cac acg cat tat gtg att ggc act ggg gcg aac gat ccg cag        1008
Ser His His Thr His Tyr Val Ile Gly Thr Gly Ala Asn Asp Pro Gln
                325                 330                 335 aag atg gat ccg cag gcc tcg cgt gaa acc ctg gat cat tcc atc atg        1056
Lys Met Asp Pro Gln Ala Ser Arg Glu Thr Leu Asp His Ser Ile Met
            340                 345                 350 tac att ttc gcc gtc gcg ctt caa gat ggc gtg tgg cac cac gag ttt        1104
Tyr Ile Phe Ala Val Ala Leu Gln Asp Gly Val Trp His His Glu Phe
        355                 360                 365 tcc tac acc cgc aag cgt tcc acc cgc ccg gaa act gtg gag ctg tgg        1152
Ser Tyr Thr Arg Lys Arg Ser Thr Arg Pro Glu Thr Val Glu Leu Trp
370                 375                 380 cac aag att cgc acc gtg gag gat cct gaa tgg acg cgc cga tac cat        1200
His Lys Ile Arg Thr Val Glu Asp Pro Glu Trp Thr Arg Arg Tyr His
385                 390                 395                 400 tct gat gat cct gca aaa aag gcc ttt ggt gcg aaa gca gtg atc aca        1248
Ser Asp Asp Pro Ala Lys Lys Ala Phe Gly Ala Lys Ala Val Ile Thr
                405                 410                 415 atg gct gat ggc acc gtg att gag gat gaa ttg gct gtc gcg gat gcc        1296
Met Ala Asp Gly Thr Val Ile Glu Asp Glu Leu Ala Val Ala Asp Ala
            420                 425                 430 cac ccg ctg ggt gct cgg ccg ttt gcg cgg gag aat tac att gaa aaa        1344
His Pro Leu Gly Ala Arg Pro Phe Ala Arg Glu Asn Tyr Ile Glu Lys
        435                 440                 445 ttc cgc aca ctc gcg cag ggg att gtc att gat tca gaa cag gaa cgc        1392
Phe Arg Thr Leu Ala Gln Gly Ile Val Ile Asp Ser Glu Gln Glu Arg
450                 455                 460 ttc ttg cat gcc gtg caa agc ctg cct gac ctg gat gat ctt gat cag        1440
Phe Leu His Ala Val Gln Ser Leu Pro Asp Leu Asp Asp Leu Asp Gln
465                 470                 475                 480 ctc aac atc gaa gtc gac ata agc aac cag gcc gcg acg aaa gcg ggg        1488
Leu Asn Ile Glu Val Asp Ile Ser Asn Gln Ala Ala Thr Lys Ala Gly
                485                 490                 495 ctg tta tga                                                            1497
Leu Leu <210> SEQ ID NO 6
<211> LENGTH: 498
<212> TYPE: PRT
<213> ORGANISM: Corynebacterium glutamicus

<400> SEQUENCE: 6

Met Arg Ile His Asp Val Tyr Thr His Leu Ser Ala Asp Asn Phe Pro
1               5                   10                  15

Lys Ala Glu His Leu Ala Trp Lys Phe Ser Glu Leu Ala Thr Asp Pro
            20                  25                  30

Val Glu Val Thr Pro Asp Val Ser Glu Met Ile Ile Asn Arg Ile Ile
        35                  40                  45

Asp Asn Ala Ala Val Ser Ala Ala Ser Val Leu Arg Arg Pro Val Thr
    50                  55                  60
```

```
Val Ala Arg Gln Gln Ala Gln Ser His Pro Arg Glu Lys Gly Gly Lys
 65                  70                  75                  80

Val Phe Gly Ile Ser Gly Ser Tyr Ser Pro Glu Trp Ala Ala Phe Ala
             85                  90                  95

Asn Gly Val Ala Val Arg Glu Leu Asp Phe His Asp Thr Phe Leu Ala
        100                 105                 110

Ala Glu Tyr Ser His Pro Gly Asp Asn Ile Pro Pro Leu Leu Ala Val
        115                 120                 125

Ala Gln Ala Gln Arg Ser Ser Gly Arg Asp Leu Ile Arg Gly Ile Ala
        130                 135                 140

Thr Ala Tyr Glu Val Gln Val Glu Leu Val Arg Gly Ile Cys Leu His
145                 150                 155                 160

Glu His Lys Ile Asp His Val Ala His Leu Gly Pro Ser Ala Ala Ala
                165                 170                 175

Gly Leu Gly Thr Leu Leu His Val Asp Glu Glu Thr Ile Tyr Gln Ala
            180                 185                 190

Ile Gly Gln Ala Leu His Thr Thr Ala Thr Arg Gln Ser Arg Lys
        195                 200                 205

Gly Glu Ile Ser Ser Trp Lys Ala Phe Ala Pro Ala Phe Ala Gly Lys
210                 215                 220

Met Ala Ile Glu Ala Met Asp Arg Ala Met Arg Gly Glu Gly Ser Pro
225                 230                 235                 240

Ala Pro Ile Trp Glu Gly Asp Gly Val Ile Ala Trp Leu Leu Ser
            245                 250                 255

Gly Lys Asp His Val Tyr His Val Pro Leu Pro Glu His Gly Glu Leu
            260                 265                 270

Lys Leu Gly Ile Leu Glu Thr Tyr Thr Lys Glu His Ser Ala Glu Tyr
            275                 280                 285

Gln Ser Gln Ala Pro Ile Asp Leu Ala Arg Arg Met Lys Pro Leu Val
        290                 295                 300

Asp Ala Ala Gly Gly Thr Glu His Ile Ala Glu Ile Val Leu Arg Thr
305                 310                 315                 320

Ser His His Thr His Tyr Val Ile Gly Thr Gly Ala Asn Asp Pro Gln
                325                 330                 335

Lys Met Asp Pro Gln Ala Ser Arg Glu Thr Leu Asp His Ser Ile Met
            340                 345                 350

Tyr Ile Phe Ala Val Ala Leu Gln Asp Gly Val Trp His His Glu Phe
        355                 360                 365

Ser Tyr Thr Arg Lys Arg Ser Thr Arg Pro Glu Thr Val Glu Leu Trp
    370                 375                 380

His Lys Ile Arg Thr Val Glu Asp Pro Glu Trp Thr Arg Arg Tyr His
385                 390                 395                 400

Ser Asp Asp Pro Ala Lys Lys Ala Phe Gly Ala Lys Ala Val Ile Thr
                405                 410                 415

Met Ala Asp Gly Thr Val Ile Glu Asp Glu Leu Ala Val Ala Asp Ala
            420                 425                 430

His Pro Leu Gly Ala Arg Pro Phe Ala Arg Glu Asn Tyr Ile Glu Lys
        435                 440                 445

Phe Arg Thr Leu Ala Gln Gly Ile Val Ile Asp Ser Glu Gln Glu Arg
450                 455                 460

Phe Leu His Ala Val Gln Ser Leu Pro Asp Leu Asp Asp Leu Asp Gln
465                 470                 475                 480

Leu Asn Ile Glu Val Asp Ile Ser Asn Gln Ala Ala Thr Lys Ala Gly
            485                 490                 495
```

Leu Leu

<210> SEQ ID NO 7
<211> LENGTH: 3035
<212> TYPE: DNA
<213> ORGANISM: Corynebacterium glutamicum
<220> FEATURE:
<221> NAME/KEY: misc_feature
<222> LOCATION: (1)..(750)
<223> OTHER INFORMATION: sequence upstream of CDS coding sequence
<220> FEATURE:
<221> NAME/KEY: primer_bind
<222> LOCATION: (661)..(680)
<223> OTHER INFORMATION: binding site of prpD1_XL_A1 primer
<220> FEATURE:
<221> NAME/KEY: misc_feature
<222> LOCATION: (751)..(2244)
<223> OTHER INFORMATION: prpD1 allele
<220> FEATURE:
<221> NAME/KEY: mutation
<222> LOCATION: (1565)..(1565)
<223> OTHER INFORMATION: C to T transition
<220> FEATURE:
<221> NAME/KEY: misc_feature
<222> LOCATION: (2245)..(3000)
<223> OTHER INFORMATION: sequence downstream from CDS sequence
<220> FEATURE:
<221> NAME/KEY: primer_bind
<222> LOCATION: (2258)..(2277)
<223> OTHER INFORMATION: binding site of prpD1_XL_E1 primer

<400> SEQUENCE: 7

```
ggttccacct tcgccataac gcttgacgac gcctccctcc ttcactctcg gcgcatcatt      60
ttggcccacg gcgccgttga cgatctgcca gaggtagaag gactgtcaga ttttgggga     120
accaaagtgt tgcactgcgc ttactgccac ggctttgagg cccgcgattc tgaaatcgtc    180
gtggtgggta cctcgcccat ggctgcgcac caagcgttga tgttctcgca gttgtccaaa    240
actgtcagct tggtgggcac gatcgacatt gatgaacaaa ccagcgagag cctagatagt    300
gctggagtaa aagtgttggg caccaatgcg gtgcgcgtat ccgccgaagg tgatggcctg    360
tctgtggaac tgtccgaagg cgatcattta agctgcgaca acatcgtggt ggcatctcgt    420
ccactggtgg atggcacgct gtacacccaa cttggtggtc agatggaaga aaacccgatg    480
ggcaggttca ttccaggtac ccaaaccggg cgcactccta ttgaaggtgt gtgggctgcc    540
ggaaacgcgc aagctcccat ggcgatggtc tatggttccg ctgctcaagg cgtgatggct    600
ggagcagaga tcaactttga tctgatcctg gaagatattt ccgtggcaag cgcgcagagc    660
taaactgcgt gaggttgtgg cctgtcacac ataatcggcc tagggtggga ctttaaggaa    720
acagtgcaca aataaatctc aaggagcccc atgcgcatcc acgatgttta tcccaccttt    780
tcggccgata actttcccaa agcagagcac cttgcgtgga aattctccga gcttgccacc    840
gaccccgtgg aggtgacacc ggatgttttcg gagatgatca tcaaccggat catcgacaac    900
gcggcggtgt ctgccgcgtc ggtgttgcgc cggcctgtga ctgtggccag gcaacaagcg    960
cagtcccatc cgcgggaaaa gggcggaaaa gtttttggaa tttcaggcag ctactcacca   1020
gagtgggctg cctttgctaa tggtgtggcc gtacgtgaat tggacttcca cgatacattt   1080
ttagcagctg aatactccca tcccggcgac aatattccac cacttcttgc agtagcgcag   1140
gctcagagaa gcagcggcag ggatctcatt cggggtatcg ccactgccta tgaggtgcag   1200
gtggaattgg tgagggggat ctgcttgcat gagcacaaaa ttgatcacgt agcccacctt   1260
ggtcccagcg ctgcagcggg tttgggcacg ttgttgcatg tagatgagga aaccatctac   1320
caggcgatcg gccaggcatt gcacaccacg acggctacga ggcagtcgcg aaaaggtgag   1380
```

```
atttccagct ggaaggcgtt cgcgccagcg tttgcgggaa agatggccat tgaggcgatg      1440
gatcgtgcga tgcgtgggga gggttcgccc gcaccgattt ggggagggcga agacggggtc      1500 atcgcgtggc tgttatcggg caaagatcat gtttatcatg tgccattgcc ggaacacggc      1560
gagctcaagc tggggattct agagacttac acaaaggaac attcagcgga atatcaatcg      1620
caggcaccga ttgatctggc gcgcaggatg aagccactgg ttgacgcggc tggcggaacg      1680
gaacacattg cagagattgt gctgcgcacc agtcaccaca cgcattatgt gattggcact      1740
ggggcgaacg atccgcagaa gatggatccg caggcctcgc gtgaaaccct ggatcattcc      1800
atcatgtaca ttttcgccgt cgcgcttcaa gatggcgtgt ggcaccacga gttttcctac      1860
acccgcaagc gttccaccas gyvatrhshs ghsrtyrthr argysargsr thrcgcccgg      1920
aaactgtgga gctgtggcac aagattcgca ccgtggagga tcctgaatgg acgcgccgat      1980
accattctga tgatcctgca aaaaaggcct ttggtgcgaa agcagtgatc acaatggctg      2040
atggcaccgt gattgaggat gaattggctg tcgcggatgc ccacccgctg ggtgctcggc      2100
cgtttgcgcg ggagaattac attgaaaaat tccgcacact cgcgcagggg attgtcattg      2160
attcagaaca ggaacgcttc ttgcatgccg tgcaaagcct gcctgacctg gatgatcttg      2220
atcagctcaa catcgaagtc gacataagca accaggccgc gacgaaagcg gggctgttat      2280
gaatctcttt tcgaatggtg ttgatgtggg gaggcgtcga caagcattta aagcggcact      2340
cgccgcaccc cacatcgccc ggctgcccgg cgcattctcc cctctgattg cgcgctccat      2400
cgaagaagcc ggcttcgaag gcgtctacgt ttccggcgcc gtcatagctg ctgacctggc      2460
actacccgat atcggcttga cgacgctgac cgaagtcgcc caccgcgcgc ggcaaattgc      2520
gcgcgtcaca gacctaggag tgcttgtcga gccgacacc ggctttggcg aacccatgtc      2580
ggccgcacgc accgtcgccg aattggagga cgccggtgtg gccggatgcc accttgaaga      2640
ccaagtcaac cccaaacgtt gcgggcactt ggacggcaaa gaagtcgtgc gcacagacgt      2700
gatggttcga cgcatcgcag ccgccgtctc ggcccggcgc gacccgaact tgtcatctg      2760 cgcccgcacc gacgccgctg gagtggaagg aatcgacgcc gccattgagc gcgcgaaagc      2820
ctacttagat gcgggcgccg acatgatttt caccgaagcc ctccacagcg aagccgactt      2880
ccgatacttc cggcacgcca tccctgatgc cttgttgctg gcgaatatga ccgaatttgg      2940
caaaacgacg ctgctgtcag ccgacgtgtt ggaagagatt ggctacaacg ccgtgatcta      3000
ccccgtgacc acgctgcgta ttgccatggg acaag                                3035
```

<210> SEQ ID NO 8
<211> LENGTH: 498
<212> TYPE: PRT
<213> ORGANISM: Corynebacterium glutamicus

<400> SEQUENCE: 8

Met Arg Ile His Asp Val Tyr Thr His Leu Ser Ala Asp Asn Phe Pro
1               5                  10                  15

Lys Ala Glu His Leu Ala Trp Lys Phe Ser Glu Leu Ala Thr Asp Pro
            20                  25                  30

Val Glu Val Thr Pro Asp Val Ser Glu Met Ile Ile Asn Arg Ile Ile
        35                  40                  45

Asp Asn Ala Ala Val Ser Ala Ala Ser Val Leu Arg Arg Pro Val Thr
    50                  55                  60

Val Ala Arg Gln Gln Ala Gln Ser His Pro Arg Glu Lys Gly Gly Lys
65                  70                  75                  80

```
Val Phe Gly Ile Ser Gly Ser Tyr Ser Pro Glu Trp Ala Ala Phe Ala
                85                  90                  95

Asn Gly Val Ala Val Arg Glu Leu Asp Phe His Asp Thr Phe Leu Ala
            100                 105                 110

Ala Glu Tyr Ser His Pro Gly Asp Asn Ile Pro Pro Leu Leu Ala Val
        115                 120                 125

Ala Gln Ala Gln Arg Ser Ser Gly Arg Asp Leu Ile Arg Gly Ile Ala
    130                 135                 140

Thr Ala Tyr Glu Val Gln Val Glu Leu Val Arg Gly Ile Cys Leu His
145                 150                 155                 160

Glu His Lys Ile Asp His Val Ala His Leu Gly Pro Ser Ala Ala Ala
                165                 170                 175

Gly Leu Gly Thr Leu Leu His Val Asp Glu Gly Thr Ile Tyr Gln Ala
            180                 185                 190

Ile Gly Gln Ala Leu His Thr Thr Thr Ala Thr Arg Gln Ser Arg Lys
        195                 200                 205

Gly Glu Ile Ser Ser Trp Lys Ala Phe Ala Pro Ala Phe Ala Gly Lys
    210                 215                 220

Met Ala Ile Glu Ala Met Asp Arg Ala Met Arg Gly Glu Gly Ser Pro
225                 230                 235                 240

Ala Pro Ile Trp Glu Gly Glu Asp Gly Val Ile Ala Trp Leu Leu Ser
                245                 250                 255

Gly Lys Asp His Val Tyr His Val Pro Leu Pro Glu His Gly Glu Leu
            260                 265                 270

Lys Leu Gly Ile Leu Glu Thr Tyr Thr Lys Glu His Ser Ala Glu Tyr
        275                 280                 285

Gln Ser Gln Ala Pro Ile Asp Leu Ala Arg Arg Met Lys Pro Leu Val
    290                 295                 300

Asp Ala Ala Gly Gly Thr Glu His Ile Ala Glu Ile Val Leu Arg Thr
305                 310                 315                 320

Ser His His Thr His Tyr Val Ile Gly Thr Gly Ala Asn Asp Pro Gln
                325                 330                 335

Lys Met Asp Pro Gln Ala Ser Arg Glu Thr Leu Asp His Ser Ile Met
            340                 345                 350

Tyr Ile Phe Ala Val Ala Leu Gln Asp Gly Val Trp His His Glu Phe
        355                 360                 365

Ser Tyr Thr Arg Lys Arg Ser Thr Arg Pro Glu Thr Val Glu Leu Trp
    370                 375                 380

His Lys Ile Arg Thr Val Glu Asp Pro Glu Trp Thr Arg Arg Tyr His
385                 390                 395                 400

Ser Asp Asp Pro Ala Lys Lys Ala Phe Gly Ala Lys Ala Val Ile Thr
                405                 410                 415

Met Ala Asp Gly Thr Val Ile Glu Asp Glu Leu Ala Val Ala Asp Ala
            420                 425                 430

His Pro Leu Gly Ala Arg Pro Phe Ala Arg Glu Asn Tyr Ile Glu Lys
        435                 440                 445

Phe Arg Thr Leu Ala Gln Gly Ile Val Ile Asp Ser Glu Gln Glu Arg
    450                 455                 460

Phe Leu His Ala Val Gln Ser Leu Pro Asp Leu Asp Asp Leu Asp Gln
465                 470                 475                 480

Leu Asn Ile Glu Val Asp Ile Ser Asn Gln Ala Ala Thr Lys Ala Gly
                485                 490                 495

Leu Leu
```

```
<210> SEQ ID NO 9
<211> LENGTH: 28
<212> TYPE: DNA
<213> ORGANISM: Artificial Sequence
<220> FEATURE:
<223> OTHER INFORMATION: Primer prpD1_XL_A1
<220> FEATURE:
<221> NAME/KEY: misc_feature
<222> LOCATION: (1)..(2)
<220> FEATURE:
<221> NAME/KEY: misc_feature
<222> LOCATION: (3)..(8)
<223> OTHER INFORMATION: EcoRI restriction site

<400> SEQUENCE: 9
gcgaattcta aactgcgtga ggttgtgg                                28

<210> SEQ ID NO 10
<211> LENGTH: 28
<212> TYPE: DNA
<213> ORGANISM: Artificial Sequence
<220> FEATURE:
<223> OTHER INFORMATION: Primer prpD1_XL_E1
<220> FEATURE:
<221> NAME/KEY: misc_feature
<222> LOCATION: (1)..(2)
<220> FEATURE:
<221> NAME/KEY: misc_feature
<222> LOCATION: (3)..(8)
<223> OTHER INFORMATION: EcoRI restriction site

<400> SEQUENCE: 10
gcgaattctc cccacatcaa caccattc                                28

<210> SEQ ID NO 11
<211> LENGTH: 1263
<212> TYPE: DNA
<213> ORGANISM: Corynebacterium glutamicus
<220> FEATURE:
<221> NAME/KEY: CDS
<222> LOCATION: (1)..(1263)
<223> OTHER INFORMATION: lysC wilde type gene coding region

<400> SEQUENCE: 11
```

| gtg | gcc | ctg | gtc | gta | cag | aaa | tat | ggc | ggt | tcc | tcg | ctt | gag | agt | gcg | 48 |
|---|---|---|---|---|---|---|---|---|---|---|---|---|---|---|---|---|
| Val | Ala | Leu | Val | Val | Gln | Lys | Tyr | Gly | Gly | Ser | Ser | Leu | Glu | Ser | Ala | |
| 1 | | | | 5 | | | | | 10 | | | | | 15 | | |

| gaa | cgc | att | aga | aac | gtc | gct | gaa | cgg | atc | gtt | gcc | acc | aag | aag | gct | 96 |
|---|---|---|---|---|---|---|---|---|---|---|---|---|---|---|---|---|
| Glu | Arg | Ile | Arg | Asn | Val | Ala | Glu | Arg | Ile | Val | Ala | Thr | Lys | Lys | Ala | |
| | | | 20 | | | | | 25 | | | | | 30 | | | |

| gga | aat | gat | gtc | gtg | gtt | gtc | tgc | tcc | gca | atg | gga | gac | acc | acg | gat | 144 |
|---|---|---|---|---|---|---|---|---|---|---|---|---|---|---|---|---|
| Gly | Asn | Asp | Val | Val | Val | Val | Cys | Ser | Ala | Met | Gly | Asp | Thr | Thr | Asp | |
| | 35 | | | | | 40 | | | | | 45 | | | | | |

| gaa | ctt | cta | gaa | ctt | gca | gcg | gca | gtg | aat | ccc | gtt | ccg | cca | gct | cgt | 192 |
|---|---|---|---|---|---|---|---|---|---|---|---|---|---|---|---|---|
| Glu | Leu | Leu | Glu | Leu | Ala | Ala | Ala | Val | Asn | Pro | Val | Pro | Pro | Ala | Arg | |
| 50 | | | | | 55 | | | | | 60 | | | | | | |

| gaa | atg | gat | atg | ctc | ctg | act | gct | ggt | gag | cgt | att | tct | aac | gct | ctc | 240 |
|---|---|---|---|---|---|---|---|---|---|---|---|---|---|---|---|---|
| Glu | Met | Asp | Met | Leu | Leu | Thr | Ala | Gly | Glu | Arg | Ile | Ser | Asn | Ala | Leu | |
| 65 | | | | 70 | | | | | 75 | | | | | 80 | | |

| gtc | gcc | atg | gct | att | gag | tcc | ctt | ggc | gca | gaa | gcc | caa | tct | ttc | acg | 288 |
|---|---|---|---|---|---|---|---|---|---|---|---|---|---|---|---|---|
| Val | Ala | Met | Ala | Ile | Glu | Ser | Leu | Gly | Ala | Glu | Ala | Gln | Ser | Phe | Thr | |
| | | | | 85 | | | | | 90 | | | | | 95 | | |

| ggc | tct | cag | gct | ggt | gtg | ctc | acc | acc | gag | cgc | cac | gga | aac | gca | cgc | 336 |
|---|---|---|---|---|---|---|---|---|---|---|---|---|---|---|---|---|
| Gly | Ser | Gln | Ala | Gly | Val | Leu | Thr | Thr | Glu | Arg | His | Gly | Asn | Ala | Arg | |
| | | | 100 | | | | | 105 | | | | | 110 | | | |

| att | gtt | gat | gtc | act | cca | ggt | cgt | gtg | cgt | gaa | gca | ctc | gat | gag | ggc | 384 |
|---|---|---|---|---|---|---|---|---|---|---|---|---|---|---|---|---|
| Ile | Val | Asp | Val | Thr | Pro | Gly | Arg | Val | Arg | Glu | Ala | Leu | Asp | Glu | Gly | |

```
                115                 120                 125
aag atc tgc att gtt gct ggt ttc cag ggt gtt aat aaa gaa acc cgc       432
Lys Ile Cys Ile Val Ala Gly Phe Gln Gly Val Asn Lys Glu Thr Arg
    130                 135                 140 gat gtc acc acg ttg ggt cgt ggt ggt tct gac acc act gca gtt gcg       480
Asp Val Thr Thr Leu Gly Arg Gly Gly Ser Asp Thr Thr Ala Val Ala
145                 150                 155                 160 ttg gca gct gct ttg aac gct gat gtg tgt gag att tac tcg gac gtt       528
Leu Ala Ala Ala Leu Asn Ala Asp Val Cys Glu Ile Tyr Ser Asp Val
                165                 170                 175 gac ggt gtg tat acc gct gac ccg cgc atc gtt cct aat gca cag aag       576
Asp Gly Val Tyr Thr Ala Asp Pro Arg Ile Val Pro Asn Ala Gln Lys
            180                 185                 190 ctg gaa aag ctc agc ttc gaa gaa atg ctg gaa ctt gct gct gtt ggc       624
Leu Glu Lys Leu Ser Phe Glu Glu Met Leu Glu Leu Ala Ala Val Gly
        195                 200                 205 tcc aag att ttg gtg ctg cgc agt gtt gaa tac gct cgt gca ttc aat       672
Ser Lys Ile Leu Val Leu Arg Ser Val Glu Tyr Ala Arg Ala Phe Asn
    210                 215                 220 gtg cca ctt cgc gta cgc tcg tct tat agt aat gat ccc ggc act ttg       720
Val Pro Leu Arg Val Arg Ser Ser Tyr Ser Asn Asp Pro Gly Thr Leu
225                 230                 235                 240 att gcc ggc tct atg gag gat att cct gtg gaa gaa gca gtc ctt acc       768
Ile Ala Gly Ser Met Glu Asp Ile Pro Val Glu Glu Ala Val Leu Thr
                245                 250                 255 ggt gtc gca acc gac aag tcc gaa gcc aaa gta acc gtt ctg ggt att       816
Gly Val Ala Thr Asp Lys Ser Glu Ala Lys Val Thr Val Leu Gly Ile
            260                 265                 270 tcc gat aag cca ggc gag gct gcg aag gtt ttc cgt gcg ttg gct gat       864
Ser Asp Lys Pro Gly Glu Ala Ala Lys Val Phe Arg Ala Leu Ala Asp
        275                 280                 285 gca gaa atc aac att gac atg gtt ctg cag aac gtc tct tct gta gaa       912
Ala Glu Ile Asn Ile Asp Met Val Leu Gln Asn Val Ser Ser Val Glu
    290                 295                 300 gac ggc acc acc gac atc acc ttc acc tgc cct cgt tcc gac ggc cgc       960
Asp Gly Thr Thr Asp Ile Thr Phe Thr Cys Pro Arg Ser Asp Gly Arg
305                 310                 315                 320 cgc gcg atg gag atc ttg aag aag ctt cag gtt cag ggc aac tgg acc      1008
Arg Ala Met Glu Ile Leu Lys Lys Leu Gln Val Gln Gly Asn Trp Thr
                325                 330                 335 aat gtg ctt tac gac gac cag gtc ggc aaa gtc tcc ctc gtg ggt gct      1056
Asn Val Leu Tyr Asp Asp Gln Val Gly Lys Val Ser Leu Val Gly Ala
            340                 345                 350 ggc atg aag tct cac cca ggt gtt acc gca gag ttc atg gaa gct ctg      1104
Gly Met Lys Ser His Pro Gly Val Thr Ala Glu Phe Met Glu Ala Leu
        355                 360                 365 cgc gat gtc aac gtg aac atc gaa ttg att tcc acc tct gag att cgt      1152
Arg Asp Val Asn Val Asn Ile Glu Leu Ile Ser Thr Ser Glu Ile Arg
    370                 375                 380 att tcc gtg ctg atc cgt gaa gat gat ctg gat gct gct gca cgt gca      1200
Ile Ser Val Leu Ile Arg Glu Asp Asp Leu Asp Ala Ala Ala Arg Ala
385                 390                 395                 400 ttg cat gag cag ttc cag ctg ggc ggc gaa gac gaa gcc gtc gtt tat      1248
Leu His Glu Gln Phe Gln Leu Gly Gly Glu Asp Glu Ala Val Val Tyr
                405                 410                 415 gca ggc acc gga cgc                                                   1263
Ala Gly Thr Gly Arg
            420

<210> SEQ ID NO 12
```

```
<211> LENGTH: 421
<212> TYPE: PRT
<213> ORGANISM: Corynebacterium glutamicus

<400> SEQUENCE: 12

Val Ala Leu Val Val Gln Lys Tyr Gly Gly Ser Ser Leu Glu Ser Ala
1               5                   10                  15

Glu Arg Ile Arg Asn Val Ala Glu Arg Ile Val Ala Thr Lys Lys Ala
            20                  25                  30

Gly Asn Asp Val Val Val Val Cys Ser Ala Met Gly Asp Thr Thr Asp
        35                  40                  45

Glu Leu Leu Glu Leu Ala Ala Ala Val Asn Pro Val Pro Pro Ala Arg
    50                  55                  60

Glu Met Asp Met Leu Leu Thr Ala Gly Glu Arg Ile Ser Asn Ala Leu
65                  70                  75                  80

Val Ala Met Ala Ile Glu Ser Leu Gly Ala Glu Ala Gln Ser Phe Thr
                85                  90                  95

Gly Ser Gln Ala Gly Val Leu Thr Thr Glu Arg His Gly Asn Ala Arg
            100                 105                 110

Ile Val Asp Val Thr Pro Gly Arg Val Arg Glu Ala Leu Asp Glu Gly
        115                 120                 125

Lys Ile Cys Ile Val Ala Gly Phe Gln Gly Val Asn Lys Glu Thr Arg
    130                 135                 140

Asp Val Thr Thr Leu Gly Arg Gly Gly Ser Asp Thr Thr Ala Val Ala
145                 150                 155                 160

Leu Ala Ala Ala Leu Asn Ala Asp Val Cys Glu Ile Tyr Ser Asp Val
                165                 170                 175

Asp Gly Val Tyr Thr Ala Asp Pro Arg Ile Val Pro Asn Ala Gln Lys
            180                 185                 190

Leu Glu Lys Leu Ser Phe Glu Glu Met Leu Glu Leu Ala Ala Val Gly
        195                 200                 205

Ser Lys Ile Leu Val Leu Arg Ser Val Glu Tyr Ala Arg Ala Phe Asn
    210                 215                 220

Val Pro Leu Arg Val Arg Ser Ser Tyr Ser Asn Asp Pro Gly Thr Leu
225                 230                 235                 240

Ile Ala Gly Ser Met Glu Asp Ile Pro Val Glu Glu Ala Val Leu Thr
                245                 250                 255

Gly Val Ala Thr Asp Lys Ser Glu Ala Lys Val Thr Val Leu Gly Ile
            260                 265                 270

Ser Asp Lys Pro Gly Glu Ala Ala Lys Val Phe Arg Ala Leu Ala Asp
        275                 280                 285

Ala Glu Ile Asn Ile Asp Met Val Leu Gln Asn Val Ser Ser Val Glu
    290                 295                 300

Asp Gly Thr Thr Asp Ile Thr Phe Thr Cys Pro Arg Ser Asp Gly Arg
305                 310                 315                 320

Arg Ala Met Glu Ile Leu Lys Lys Leu Gln Val Gln Gly Asn Trp Thr
                325                 330                 335

Asn Val Leu Tyr Asp Asp Gln Val Gly Lys Val Ser Leu Val Gly Ala
            340                 345                 350

Gly Met Lys Ser His Pro Gly Val Thr Ala Glu Phe Met Glu Ala Leu
        355                 360                 365

Arg Asp Val Asn Val Asn Ile Glu Leu Ile Ser Thr Ser Glu Ile Arg
    370                 375                 380

Ile Ser Val Leu Ile Arg Glu Asp Asp Leu Asp Ala Ala Ala Arg Ala
385                 390                 395                 400
```

Leu His Glu Gln Phe Gln Leu Gly Gly Glu Asp Glu Ala Val Val Tyr
            405                 410                 415

Ala Gly Thr Gly Arg
            420

<210> SEQ ID NO 13
<211> LENGTH: 1633
<212> TYPE: DNA
<213> ORGANISM: Corynebacterium glutamicus
<220> FEATURE:
<221> NAME/KEY: misc_feature
<222> LOCATION: (1)..(2)
<220> FEATURE:
<221> NAME/KEY: misc_feature
<222> LOCATION: (1)..(1633)
<223> OTHER INFORMATION: PCR product
<220> FEATURE:
<221> NAME/KEY: misc_structure
<222> LOCATION: (3)..(8)
<223> OTHER INFORMATION: EcoRI restriction site
<220> FEATURE:
<221> NAME/KEY: misc_feature
<222> LOCATION: (99)..(1592)
<223> OTHER INFORMATION: coding region
<220> FEATURE:
<221> NAME/KEY: mutation
<222> LOCATION: (913)..(913)
<223> OTHER INFORMATION: C to T transition
<220> FEATURE:
<221> NAME/KEY: misc_structure
<222> LOCATION: (1626)..(1631)
<223> OTHER INFORMATION: EcoRI restriction site
<220> FEATURE:
<221> NAME/KEY: misc_feature
<222> LOCATION: (1632)..(1633)

<400> SEQUENCE: 13
gcgaattcta aactgcgtga ggttgtggcc tgtcacacat aatcggccta gggtgggact      60
ttaaggaaac agtgcacaaa taaatctcaa ggagccccat gcgcatccac gatgtttata     120
cccacctttc ggccgataac tttcccaaag cagagcacct tgcgtggaaa ttctccgagc     180
ttgccaccga ccccgtggag gtgacaccgg atgtttcgga gatgatcatc aaccggatca     240
tcgacaacgc ggcggtgtct gccgcgtcgg tgttgcgccg gcctgtgact gtggccaggc     300
aacaagcgca gtcccatccg cgggaaaagg gcggaaaagt ttttggaatt caggcagct     360 actcaccaga gtgggctgcc tttgctaatg gtgtggccgt acgtgaattg gacttccacg     420
atacattttt agcagctgaa tactcccatc ccggcgacaa tattccacca cttcttgcag     480
tagcgcaggc tcagagaagc agcggcaggg atctcattcg gggtatcgcc actgcctatg     540
aggtgcaggt ggaattggtg aggggatct gcttgcatga gcacaaaatt gatcacgtag     600
cccaccttgg tcccagcgct gcagcgggtt tgggcacgtt gttgcatgta gatgaggaaa     660
ccatctacca ggcgatcggc caggcattgc acaccacgac ggctacgagg cagtcgcgaa     720
aaggtgagat ttcagctgg aaggcgttcg cgccagcgtt tgcgggaaag atggccattg     780
aggcgatgga tcgtgcgatg cgtgggagg gttcgcccgc accgatttgg gagggcgaag     840
acggggtcat cgcgtggctg ttatcgggca agatcatgt ttatcatgtg ccattgccgg     900
aacacggcga gctcaagctg ggattctag agacttacac aaaggaacat tcagcggaat     960
atcaatcgca ggcaccgatt gatctggcgc gcaggatgaa gccactggtt gacgcggctg    1020
gcggaacgga acacattgca gagattgtgc tgcgcaccag tcaccacacg cattatgtga    1080
ttggcactgg ggcgaacgat ccgcagaaga tggatccgca ggcctcgcgt gaaaccctgg    1140
atcattccat catgtacatt ttcgccgtcg cgcttcaaga tggcgtgtgg caccacgagt    1200

-continued

```
tttcctacac ccgcaagcgt tccacccgcc cggaaactgt ggagctgtgg cacaagattc    1260
gcaccgtgga ggatcctgaa tggacgcgcc gataccattc tgatgatcct gcaaaaaagg    1320
cctttggtgc gaaagcagtg atcacaatgg ctgatggcac cgtgattgag atgaattgg     1380 ctgtcgcgga tgcccacccg ctgggtgctc ggccgtttgc gcgggagaat tacattgaaa    1440
aattccgcac actcgcgcag gggattgtca ttgattcaga acaggaacgc ttcttgcatg    1500
ccgtgcaaag cctgcctgac ctggatgatc ttgatcagct caacatcgaa gtcgacataa    1560
gcaaccaggc cgcgacgaaa gcggggctgt tatgaatctc ttttcgaatg gtgttgatgt    1620
ggggagaatt cgc                                                       1633
```

<210> SEQ ID NO 14
<211> LENGTH: 498
<212> TYPE: PRT
<213> ORGANISM: Corynebacterium glutamicus

<400> SEQUENCE: 14

```
Met Arg Ile His Asp Val Tyr Thr His Leu Ser Ala Asp Asn Phe Pro
1               5                   10                  15

Lys Ala Glu His Leu Ala Trp Lys Phe Ser Glu Leu Ala Thr Asp Pro
            20                  25                  30

Val Glu Val Thr Pro Asp Val Ser Glu Met Ile Ile Asn Arg Ile Ile
        35                  40                  45

Asp Asn Ala Ala Val Ser Ala Ala Ser Val Leu Arg Arg Pro Val Thr
    50                  55                  60

Val Ala Arg Gln Gln Ala Gln Ser His Pro Arg Glu Lys Gly Gly Lys
65                  70                  75                  80

Val Phe Gly Ile Ser Gly Ser Tyr Ser Pro Glu Trp Ala Ala Phe Ala
                85                  90                  95

Asn Gly Val Ala Val Arg Glu Leu Asp Phe His Asp Thr Phe Leu Ala
            100                 105                 110

Ala Glu Tyr Ser His Pro Gly Asp Asn Ile Pro Pro Leu Leu Ala Val
        115                 120                 125

Ala Gln Ala Gln Arg Ser Ser Gly Arg Asp Leu Ile Arg Gly Ile Ala
    130                 135                 140

Thr Ala Tyr Glu Val Gln Val Glu Leu Val Arg Gly Ile Cys Leu His
145                 150                 155                 160

Glu His Lys Ile Asp His Val Ala His Leu Gly Pro Ser Ala Ala Ala
                165                 170                 175

Gly Leu Gly Thr Leu Leu His Val Asp Glu Glu Thr Ile Tyr Gln Ala
            180                 185                 190

Ile Gly Gln Ala Leu His Thr Thr Thr Ala Thr Arg Gln Ser Arg Lys
        195                 200                 205

Gly Glu Ile Ser Ser Trp Lys Ala Phe Ala Pro Ala Phe Ala Gly Lys
    210                 215                 220

Met Ala Ile Glu Ala Met Asp Arg Ala Met Arg Gly Glu Gly Ser Pro
225                 230                 235                 240

Ala Pro Ile Trp Glu Gly Asp Gly Val Ile Ala Trp Leu Leu Ser
                245                 250                 255

Gly Lys Asp His Val Tyr His Val Pro Leu Pro Glu His Gly Glu Leu
            260                 265                 270

Lys Leu Gly Ile Leu Glu Thr Tyr Thr Lys Glu His Ser Ala Glu Tyr
        275                 280                 285

Gln Ser Gln Ala Pro Ile Asp Leu Ala Arg Arg Met Lys Pro Leu Val
```

```
                290               295                300
Asp Ala Ala Gly Gly Thr Glu His Ile Ala Glu Ile Val Leu Arg Thr
305                 310                 315                 320

Ser His His Thr His Tyr Val Ile Gly Thr Gly Ala Asn Asp Pro Gln
                325                 330                 335

Lys Met Asp Pro Gln Ala Ser Arg Glu Thr Leu Asp His Ser Ile Met
            340                 345                 350

Tyr Ile Phe Ala Val Ala Leu Gln Asp Gly Val Trp His His Glu Phe
        355                 360                 365

Ser Tyr Thr Arg Lys Arg Ser Thr Arg Pro Glu Thr Val Glu Leu Trp
    370                 375                 380

His Lys Ile Arg Thr Val Glu Asp Pro Glu Trp Thr Arg Arg Tyr His
385                 390                 395                 400

Ser Asp Asp Pro Ala Lys Lys Ala Phe Gly Ala Lys Ala Val Ile Thr
                405                 410                 415

Met Ala Asp Gly Thr Val Ile Glu Asp Glu Leu Ala Val Ala Asp Ala
            420                 425                 430

His Pro Leu Gly Ala Arg Pro Phe Ala Arg Glu Asn Tyr Ile Glu Lys
        435                 440                 445

Phe Arg Thr Leu Ala Gln Gly Ile Val Ile Asp Ser Glu Gln Glu Arg
    450                 455                 460

Phe Leu His Ala Val Gln Ser Leu Pro Asp Leu Asp Asp Leu Asp Gln
465                 470                 475                 480

Leu Asn Ile Glu Val Asp Ile Ser Asn Gln Ala Ala Thr Lys Ala Gly
                485                 490                 495

Leu Leu

<210> SEQ ID NO 15
<211> LENGTH: 1311
<212> TYPE: DNA
<213> ORGANISM: Corynebacterium glutamicus
<220> FEATURE:
<221> NAME/KEY: CDS
<222> LOCATION: (1)..(1308)
<223> OTHER INFORMATION: ilvA wild type gene coding region

<400> SEQUENCE: 15 atg agt gaa aca tac gtg tct gag aaa agt cca gga gtg atg gct agc      48
Met Ser Glu Thr Tyr Val Ser Glu Lys Ser Pro Gly Val Met Ala Ser
1               5                   10                  15 gga gcg gag ctg att cgt gcc gcc gac att caa acg gcg cag gca cga      96
Gly Ala Glu Leu Ile Arg Ala Ala Asp Ile Gln Thr Ala Gln Ala Arg
            20                  25                  30 att tcc tcc gtc att gca cca act cca ttg cag tat tgc cct cgt ctt     144
Ile Ser Ser Val Ile Ala Pro Thr Pro Leu Gln Tyr Cys Pro Arg Leu
        35                  40                  45 tct gag gaa acc gga gcg gaa atc tac ctt aag cgt gag gat ctg cag     192
Ser Glu Glu Thr Gly Ala Glu Ile Tyr Leu Lys Arg Glu Asp Leu Gln
    50                  55                  60 gat gtt cgt tcc tac aag atc cgc ggt gcg ctg aac tct gga gcg cag     240
Asp Val Arg Ser Tyr Lys Ile Arg Gly Ala Leu Asn Ser Gly Ala Gln
65                  70                  75                  80 ctc acc caa gag cag cgc gat gca ggt atc gtt gcc gca tct gca ggt     288
Leu Thr Gln Glu Gln Arg Asp Ala Gly Ile Val Ala Ala Ser Ala Gly
                85                  90                  95 aac cat gcc cag ggc gtg gcc tat gtg tgc aag tcc ttg ggc gtt cag     336
Asn His Ala Gln Gly Val Ala Tyr Val Cys Lys Ser Leu Gly Val Gln
            100                 105                 110
```

| | |
|---|---|
| gga cgc atc tat gtt cct gtg cag act cca aag caa aag cgt gac cgc<br>Gly Arg Ile Tyr Val Pro Val Gln Thr Pro Lys Gln Lys Arg Asp Arg<br>    115                    120               125 | 384 |
| atc atg gtt cac ggc gga gag ttt gtc tcc ttg gtg gtc act ggc aat<br>Ile Met Val His Gly Gly Glu Phe Val Ser Leu Val Val Thr Gly Asn<br>130                   135                  140 | 432 |
| aac ttc gac gaa gca tcg gct gca gcg cat gaa gat gca gag cgc acc<br>Asn Phe Asp Glu Ala Ser Ala Ala Ala His Glu Asp Ala Glu Arg Thr<br>145                   150              155              160 | 480 |
| ggc gca acg ctg atc gag cct ttc gat gct cgc aac acc gtc atc ggt<br>Gly Ala Thr Leu Ile Glu Pro Phe Asp Ala Arg Asn Thr Val Ile Gly<br>                  165                  170              175 | 528 |
| cag ggc acc gtg gct gct gag atc ttg tcg cag ctg act tcc atg ggc<br>Gln Gly Thr Val Ala Ala Glu Ile Leu Ser Gln Leu Thr Ser Met Gly<br>             180                  185              190 | 576 |
| aag agt gca gat cac gtg atg gtt cca gtc ggc ggt ggc gga ctt ctt<br>Lys Ser Ala Asp His Val Met Val Pro Val Gly Gly Gly Gly Leu Leu<br>          195                  200              205 | 624 |
| gca ggt gtg gtc agc tac atg gct gat atg gca cct cgc act gcg atc<br>Ala Gly Val Val Ser Tyr Met Ala Asp Met Ala Pro Arg Thr Ala Ile<br>210                   215                  220 | 672 |
| gtt ggt atc gaa cca gcg gga gca gca tcc atg cag gct gca ttg cac<br>Val Gly Ile Glu Pro Ala Gly Ala Ala Ser Met Gln Ala Ala Leu His<br>225                   230              235              240 | 720 |
| aat ggt gga cca atc act ttg gag act gtt gat ccc ttt gtg gac ggc<br>Asn Gly Gly Pro Ile Thr Leu Glu Thr Val Asp Pro Phe Val Asp Gly<br>                  245                  250              255 | 768 |
| gca gca gtc aaa cgt gtc gga gat ctc aac tac acc atc gtg gag aag<br>Ala Ala Val Lys Arg Val Gly Asp Leu Asn Tyr Thr Ile Val Glu Lys<br>             260                  265              270 | 816 |
| aac cag ggt cgc gtg cac atg atg agc gcg acc gag ggc gct gtg tgt<br>Asn Gln Gly Arg Val His Met Met Ser Ala Thr Glu Gly Ala Val Cys<br>          275                  280              285 | 864 |
| act gag atg ctc gat ctt tac caa aac gaa ggc atc atc gcg gag cct<br>Thr Glu Met Leu Asp Leu Tyr Gln Asn Glu Gly Ile Ile Ala Glu Pro<br>290                   295                  300 | 912 |
| gct ggc gcg ctg tct atc gct ggg ttg aag gaa atg tcc ttt gca cct<br>Ala Gly Ala Leu Ser Ile Ala Gly Leu Lys Glu Met Ser Phe Ala Pro<br>305                   310              315              320 | 960 |
| ggt tct gtc gtg gtg tgc atc atc tct ggt ggc aac aac gat gtg ctg<br>Gly Ser Val Val Val Cys Ile Ile Ser Gly Gly Asn Asn Asp Val Leu<br>                  325                  330              335 | 1008 |
| cgt tat gcg gaa atc gct gag cgc tcc ttg gtg cac cgc ggt ttg aag<br>Arg Tyr Ala Glu Ile Ala Glu Arg Ser Leu Val His Arg Gly Leu Lys<br>             340                  345              350 | 1056 |
| cac tac ttc ttg gtg aac ttc ccg caa aag cct ggt cag ttg cgt cac<br>His Tyr Phe Leu Val Asn Phe Pro Gln Lys Pro Gly Gln Leu Arg His<br>          355                  360              365 | 1104 |
| ttc ctg gaa gat atc ctg gga ccg gat gat gac atc acg ctg ttt gag<br>Phe Leu Glu Asp Ile Leu Gly Pro Asp Asp Asp Ile Thr Leu Phe Glu<br>370                   375                  380 | 1152 |
| tac ctc aag cgc aac aac cgt gag acc ggt act gcg ttg gtg ggt att<br>Tyr Leu Lys Arg Asn Asn Arg Glu Thr Gly Thr Ala Leu Val Gly Ile<br>385                   390              395              400 | 1200 |
| cac ttg agt gaa gca tca gga ttg gat tct ttg ctg gaa cgt atg gag<br>His Leu Ser Glu Ala Ser Gly Leu Asp Ser Leu Leu Glu Arg Met Glu<br>             405                  410              415 | 1248 |
| gaa tcg gca att gat tcc cgt cgc ctc gag ccg ggc acc cct gag tac<br>Glu Ser Ala Ile Asp Ser Arg Arg Leu Glu Pro Gly Thr Pro Glu Tyr<br>             420                  425              430 | 1296 |

```
gaa tac ttg acc taa                                                    1311
Glu Tyr Leu Thr
        435
```

<210> SEQ ID NO 16
<211> LENGTH: 436
<212> TYPE: PRT
<213> ORGANISM: Corynebacterium glutamicus

<400> SEQUENCE: 16

Met Ser Glu Thr Tyr Val Ser Glu Lys Ser Pro Gly Val Met Ala Ser
1               5                   10                  15

Gly Ala Glu Leu Ile Arg Ala Ala Asp Ile Gln Thr Ala Gln Ala Arg
            20                  25                  30

Ile Ser Ser Val Ile Ala Pro Thr Pro Leu Gln Tyr Cys Pro Arg Leu
        35                  40                  45

Ser Glu Glu Thr Gly Ala Glu Ile Tyr Leu Lys Arg Glu Asp Leu Gln
    50                  55                  60

Asp Val Arg Ser Tyr Lys Ile Arg Gly Ala Leu Asn Ser Gly Ala Gln
65                  70                  75                  80

Leu Thr Gln Glu Gln Arg Asp Ala Gly Ile Val Ala Ala Ser Ala Gly
                85                  90                  95

Asn His Ala Gln Gly Val Ala Tyr Val Cys Lys Ser Leu Gly Val Gln
            100                 105                 110

Gly Arg Ile Tyr Val Pro Val Gln Thr Pro Lys Gln Lys Arg Asp Arg
        115                 120                 125

Ile Met Val His Gly Gly Glu Phe Val Ser Leu Val Val Thr Gly Asn
    130                 135                 140

Asn Phe Asp Glu Ala Ser Ala Ala His Glu Asp Ala Glu Arg Thr
145                 150                 155                 160

Gly Ala Thr Leu Ile Glu Pro Phe Asp Ala Arg Asn Thr Val Ile Gly
                165                 170                 175

Gln Gly Thr Val Ala Ala Glu Ile Leu Ser Gln Leu Thr Ser Met Gly
            180                 185                 190

Lys Ser Ala Asp His Val Met Val Pro Val Gly Gly Gly Gly Leu Leu
        195                 200                 205

Ala Gly Val Val Ser Tyr Met Ala Asp Met Ala Pro Arg Thr Ala Ile
    210                 215                 220

Val Gly Ile Glu Pro Ala Gly Ala Ala Ser Met Gln Ala Ala Leu His
225                 230                 235                 240

Asn Gly Gly Pro Ile Thr Leu Glu Thr Val Asp Pro Phe Val Asp Gly
                245                 250                 255

Ala Ala Val Lys Arg Val Gly Asp Leu Asn Tyr Thr Ile Val Glu Lys
            260                 265                 270

Asn Gln Gly Arg Val His Met Met Ser Ala Thr Glu Gly Ala Val Cys
        275                 280                 285

Thr Glu Met Leu Asp Leu Tyr Gln Asn Glu Gly Ile Ile Ala Glu Pro
    290                 295                 300

Ala Gly Ala Leu Ser Ile Ala Gly Leu Lys Glu Met Ser Phe Ala Pro
305                 310                 315                 320

Gly Ser Val Val Val Cys Ile Ile Ser Gly Gly Asn Asn Asp Val Leu
                325                 330                 335

Arg Tyr Ala Glu Ile Ala Glu Arg Ser Leu Val His Arg Gly Leu Lys
            340                 345                 350

His Tyr Phe Leu Val Asn Phe Pro Gln Lys Pro Gly Gln Leu Arg His
        355                 360                 365

-continued

```
Phe Leu Glu Asp Ile Leu Gly Pro Asp Asp Ile Thr Leu Phe Glu
    370                 375                 380
Tyr Leu Lys Arg Asn Asn Arg Glu Thr Gly Thr Ala Leu Val Gly Ile
385                 390                 395                 400
His Leu Ser Glu Ala Ser Gly Leu Asp Ser Leu Leu Glu Arg Met Glu
                405                 410                 415
Glu Ser Ala Ile Asp Ser Arg Arg Leu Glu Pro Gly Thr Pro Glu Tyr
            420                 425                 430
Glu Tyr Leu Thr
        435

<210> SEQ ID NO 17
<211> LENGTH: 120
<212> TYPE: DNA
<213> ORGANISM: Corynebacterium glutamicum
<220> FEATURE:
<221> NAME/KEY: CDS
<222> LOCATION: (1)..(120)
<223> OTHER INFORMATION: part of the coding region of prpD1-alleles
<220> FEATURE:
<221> NAME/KEY: misc_feature
<222> LOCATION: (61)..(63)
<223> OTHER INFORMATION: n is a, c, g, or t

<400> SEQUENCE: 17 gcg tgg ctg tta tcg ggc aaa gat cat gtt tat cat gtg cca ttg ccg    48
Ala Trp Leu Leu Ser Gly Lys Asp His Val Tyr His Val Pro Leu Pro
1               5                  10                  15 gaa cac ggc gag nnn aag ctg ggg att cta gag act tac aca aag gaa    96
Glu His Gly Glu Xaa Lys Leu Gly Ile Leu Glu Thr Tyr Thr Lys Glu
                20                  25                  30 cat tca gcg gaa tat caa tcg cag                                    120
His Ser Ala Glu Tyr Gln Ser Gln
        35                  40

<210> SEQ ID NO 18
<211> LENGTH: 40
<212> TYPE: PRT
<213> ORGANISM: Corynebacterium glutamicum
<220> FEATURE:
<221> NAME/KEY: misc_feature
<222> LOCATION: (21)..(21)
<223> OTHER INFORMATION: The 'Xaa' at location 21 stands for Lys, Asn,
      Arg, Ser, Thr, Ile, Met, Glu, Asp, Gly, Ala, Val, Gln, His, Pro,
      Leu, Tyr, Trp, Cys, or Phe.

<400> SEQUENCE: 18

Ala Trp Leu Leu Ser Gly Lys Asp His Val Tyr His Val Pro Leu Pro
1               5                  10                  15

Glu His Gly Glu Xaa Lys Leu Gly Ile Leu Glu Thr Tyr Thr Lys Glu
                20                  25                  30

His Ser Ala Glu Tyr Gln Ser Gln
        35                  40

<210> SEQ ID NO 19
<211> LENGTH: 120
<212> TYPE: DNA
<213> ORGANISM: Corynebacterium glutamicum
<220> FEATURE:
<221> NAME/KEY: CDS
<222> LOCATION: (1)..(120)
<223> OTHER INFORMATION: part of the coding region of prpD1- alleles

<400> SEQUENCE: 19 gcg tgg ctg tta tcg ggc aaa gat cat gtt tat cat gtg cca ttg ccg    48
```

```
Ala Trp Leu Leu Ser Gly Lys Asp His Val Tyr His Val Pro Leu Pro
1               5                   10                  15 gaa cac ggc gag ctc aag ctg ggg att cta gag act tac aca aag gaa    96
Glu His Gly Glu Leu Lys Leu Gly Ile Leu Glu Thr Tyr Thr Lys Glu
            20                  25                  30 cat tca gcg gaa tat caa tcg cag                                    120
His Ser Ala Glu Tyr Gln Ser Gln
        35                  40
```

<210> SEQ ID NO 20
<211> LENGTH: 40
<212> TYPE: PRT
<213> ORGANISM: Corynebacterium glutamicus

<400> SEQUENCE: 20

```
Ala Trp Leu Leu Ser Gly Lys Asp His Val Tyr His Val Pro Leu Pro
1               5                   10                  15

Glu His Gly Glu Leu Lys Leu Gly Ile Leu Glu Thr Tyr Thr Lys Glu
            20                  25                  30

His Ser Ala Glu Tyr Gln Ser Gln
        35                  40
```

<210> SEQ ID NO 21
<211> LENGTH: 17
<212> TYPE: PRT
<213> ORGANISM: Artificial Sequence
<220> FEATURE:
<223> OTHER INFORMATION: Synthetic; motif
<220> FEATURE:
<221> NAME/KEY: MISC_FEATURE
<222> LOCATION: (13)..(13)
<223> OTHER INFORMATION: Xaa is D or E

<400> SEQUENCE: 21

```
Arg Glu Leu Asp Phe His Asp Thr Phe Leu Ala Ala Xaa Tyr Ser His
1               5                   10                  15

Pro
```

<210> SEQ ID NO 22
<211> LENGTH: 17
<212> TYPE: PRT
<213> ORGANISM: Artificial Sequence
<220> FEATURE:
<223> OTHER INFORMATION: Synthetic; motif

<400> SEQUENCE: 22

```
Gly Ile Cys Leu His Glu His Lys Ile Asp His Val Ala His Leu Gly
1               5                   10                  15

Pro
```

<210> SEQ ID NO 23
<211> LENGTH: 16
<212> TYPE: PRT
<213> ORGANISM: Artificial Sequence
<220> FEATURE:
<223> OTHER INFORMATION: Synthetic; motif

<400> SEQUENCE: 23

```
Pro Ala Pro Ile Trp Glu Gly Glu Asp Gly Val Ile Ala Trp Leu Leu
1               5                   10                  15
```

ALLELES OF THE PRPD1 GENE FROM CORYNEFORM BACTERIA

CROSS REFERENCES TO RELATED APPLICATIONS

This application is a divisional of U.S. application Ser. No. 11/923,942, filed Oct. 25, 2007, which claims priority to the German Application 102006050489, filed Oct. 26, 2006.

BACKGROUND OF THE INVENTION

1. Field of the Invention

The invention relates to mutants and alleles of the prpD1 gene of coryneform bacteria coding for variants of 2-methylcitrate dehydratase (EC No. 4.2.1.79) and methods for producing amino acids, preferably L-lysine, L-tryptophan, L-valine, L-isoleucine and L-homoserine using bacteria which comprise these alleles.

2. Description of the Related Art

All publications, patent applications, patents, and other references mentioned herein are incorporated by reference in their entirety. Further, the materials, methods, and examples are illustrative only and are not intended to be limiting, unless otherwise specified.

Amino acids are used in human medicine, in the pharmaceutical industry, in the food product industry and in livestock nutrition.

Amino acids are produced by fermentation of strains of coryneform bacteria, for example, *Corynebacterium glutamicum*. Due to the great importance, work on improving the production methods is continually being done. Improvements in the methods may be fermentation technology measures such as, for example, stirring and supplying oxygen, or relate to the composition of the nutrient media, such as, for example, the sugar concentration during the fermentation, or the working up to the product form by for example ion exchange chromatography or the intrinsic output properties of the microorganism itself.

Methods used for improving the output properties of these microorganisms are ones of mutagenesis, selection and choice of mutants. The strains obtained in this way are resistant to antimetabolites or are auxotrophic for metabolites of regulatory importance, and produce the amino acids. A known antimetabolite is the lysine analogue S-(2-aminoethyl)-L-cysteine (AEC).

Methods of recombinant DNA technology have likewise been used for some years for strain improvement of L-amino acid-producing strains of *Corynebacterium* by amplifying individual amino acid biosynthesis genes and investigating the effect on amino acid production.

The chromosome of *Corynebacterium glutamicum* was completely sequenced some time ago (Kalinowski et al., Journal of Biotechnology 104, 5-25 (2003)). The chromosome of *Corynebacterium efficiens* has likewise been sequenced (Nishio et al., Genome Res. 13 (7), 1572-1579 (2003)).

Corresponding sequence data can be taken from the public databases. Suitable databases are for example the database of the European Molecular Biology Laboratories (EMBL, Heidelberg, Germany and Cambridge, UK), the database of the National Center for Biotechnology Information (NCBI, Bethesda, Md., USA), that of the Swiss Institute of Bioinformatics (Swissprot, Geneva, Switzerland), the Protein Information Resource Database (PIR, Washington, D.C., USA) and the DNA Data Bank of Japan (DDBJ, 1111 Yata, Mishima, 411-8540, Japan).

Summarizing descriptions of the genetics, the metabolism and the industrial importance of *Corynebacterium* are to be found in the articles by Ikeda, by Pfefferle et al. and by Mueller and Huebner in the book "Microbial Production of L-Amino Acids" (Advances in Biochemical Engineering 79, (2003), Springer Verlag, Berlin, Germany, editor: T. Scheper), in the special edition "A New Era in *Corynebacterium glutamicum* Biotechnology" of the Journal of Biotechnology (volume 104 (1-3), 2003, editors: A. Pühler and T. Tauch) and in the "Handbook of *Corynebacterium glutamicum*" (editors: L. Eggeling and M. Bott, CRC Press, Taylor & Francis Group, Boca Raton, Fla., USA, 2005).

The nucleotide sequence of the prpD1 gene coding for the 2-methylcitrate dehydratase of *Corynebacterium glutamicum* is available inter alia in the database of the National Center for Biotechnology Information (NCBI) of the National Library of Medicine (Bethesda, Md., USA) under the access number AF434798. It can furthermore be found in the Patent Application EP 1 108 790 as sequence No. 770.

Claes et al. (Journal of Bacteriology 184(10), 2728-2739 (2002)) report on genetic, microbiological and biochemical investigations on the prpD1, prpB1 and prpC1 genes of *Corynebacterium glutamicum* ATCC 13032.

For improved clarity, the nucleotide sequence of the prpD1 gene coding for the 2-methylcitrate dehydratase from *Corynebacterium glutamicum* ("wild-type gene") according to the data of the NCBI database is depicted in SEQ ID NO:1, and the amino acid sequence of the encoded 2-methylcitrate dehydratase resulting therefrom is depicted in SEQ ID NO:2 and 4. Nucleotide sequences located upstream and downstream are additionally indicated in SEQ ID NO:3.

SUMMARY OF THE INVENTION

It was an object of the present invention to provide novel measures for the improved production of amino acids, preferably L-lysine, L-tryptophan, L-valine, L-isoleucine and L-homoserine.

This and other objects have been achieved by the present invention the first embodiment of which includes an isolated mutant of coryneform bacteria comprising a gene encodes a polypeptide having 2-methylcitrate dehydratase activity, where the polypeptide comprises an amino acid sequence in which one of the proteinogenic amino acids except L-proline is present at position 272 or a corresponding or comparable position.

The invention provides an isolated polynucleotide encoding a polypeptide having 2-methylcitrate dehydratase enzymic activity, which comprises at position 272 of the amino acid sequence or a corresponding or comparable position a proteinogenic amino acid except L-proline.

The invention further provides a method for producing a recombinant coryneform bacterium and L-amino acids.

The invention also provides a recombinant microorganism, L-Lysine-containing feed additive, and L-Tryptophan-containing feed additive.

BRIEF DESCRIPTION OF THE DRAWINGS

The FIGURE represents a map of the plasmid pK18moBSacB_prpD1_P272L.

DESCRIPTION OF THE INVENTION

The invention relates to generated and isolated mutants of coryneform bacteria which preferentially secrete amino acids and which comprise a gene or allele which codes for a polypeptide having 2-methylcitrate dehydratase activity, characterized in that the polypeptide includes an amino acid sequence in which one of the proteinogenic amino acids except L-proline is present at position 272 or at a corresponding or comparable position of the amino acid sequence. Exchange of L-proline for L-leucine is preferred.

Among the coryneform bacteria, the genus *Corynebacterium* is preferred. In the genus *Corynebacterium*, the following species are preferred:

*Corynebacterium efficiens* (type strain DSM44549),
*Corynebacterium glutamicum* (type strain ATCC13032),
*Corynebacterium thermoaminogenes* (for example the strain FERM BP-1539), and
*Corynebacterium ammoniagenes* (type strain ATCC6871), and more preferably the species *Corynebacterium glutamicum*.

Some representatives of the species *Corynebacterium glutamicum* are known in the state of the art also under other species designations. These include for example:

*Corynebacterium acetoacidophilum* ATCC127270,
*Corynebacterium lilium* DSM20137,
*Corynebacterium melassecola* ATCC 17965,
*Brevibacterium flavum* ATCC14067,
*Brevibacterium lactofermentum* ATCC 127269,
*Brevibacterium divaricatum* ATCC14020, and
*Microbacterium ammoniaphilum* ATCC15354.

The term "*Micrococcus glutamicus*" for *Corynebacterium glutamicum* has likewise been in use.

The strains of coryneform bacteria employed for the measures of the invention preferably already have the ability to enrich the desired amino acid in the cell and/or secrete it into the nutrient medium surrounding it and accumulate it. The term "produce" is also used for this hereinafter. In particular, the strains of coryneform bacteria employed have the ability to enrich or to accumulate $\geq$(at least) 0.25 g/l, $\geq$0.5 g/l, $\geq$1.0 g/l, $\geq$1.5 g/l, $\geq$2.0 g/l, $\geq$4 g/l or $\geq$10 g/l of the desired amino acid in $\leq$(at most) 120 hours, $\leq$96 hours, $\leq$48 hours, $\leq$36 hours, $\leq$24 hours or $\leq$12 hours in the cell or in the nutrient medium. In this connection, the strains may have been produced by mutagenesis and selection, by recombinant DNA techniques or by a combination of the two methods.

Known representatives of L-lysine-producing or secreting strains of coryneform bacteria are for example:

*Corynebacterium glutamicum* DM58-1/pDM6 (=DSM4697) described in EP 0 358 940,
*Corynebacterium glutamicum* MH20-22B (=DSM16835) described in Menkel et al. (Applied and Environmental Microbiology 55(3), 684-688 (1989)),
*Corynebacterium glutamicum* AHP-3 (=Ferm BP-7382) described in EP 1 108 790,
*Corynebacterium glutamicum* NRRL B-11474 described in U.S. Pat. No. 4,275,157, and
*Corynebacterium thermoaminogenes* AJ12521 FERM BP-3304) described in U.S. Pat. No. 5,250,423.

Known representatives of L-tryptophan-producing or secreting strains of coryneform bacteria are for example:

*Corynebacterium glutamicum* K76 (=Ferm BP-1847) described in U.S. Pat. No. 5,563,052,
*Corynebacterium glutamicum* BPS13 (=Ferm BP-1777) described in U.S. Pat. No. 5,605,818, and
*Corynebacterium glutamicum* Ferm BP-3055 described in U.S. Pat. No. 5,235,940.

Known representatives of L-valine-producing or secreting strains of coryneform bacteria are for example:

*Brevibacterium lactofermentum* FERM BP-1763 described in U.S. Pat. No. 5,188,948,
*Brevibacterium lactofermentum* FERM BP-3007 described in U.S. Pat. No. 5,521,074,
*Corynebacterium glutamicum* FERM BP-3006 described in U.S. Pat. No. 5,521,074, and
*Corynebacterium glutamicum* FERM BP-1764 described in U.S. Pat. No. 5,188,948.

Known representatives of L-isoleucine-producing or secreting strains of coryneform bacteria are for example:

*Brevibacterium flavum* FERM BP-760 described in U.S. Pat. No. 4,656,135,
*Brevibacterium flavum* FERM BP-2215 described in U.S. Pat. No. 5,294,547, and
*Corynebacterium glutamicum* FERM BP-758 described in U.S. Pat. No. 4,656,135.

Known representatives of L-homoserine-producing or secreting strains of coryneform bacteria are for example:

*Micrococcus glutamicus* ATCC 14296 described in U.S. Pat. No. 3,189,526 and
*Micrococcus glutamicus* ATCC 14297 described in U.S. Pat. No. 3,189,526.

Data on the taxonomic classification of strains of this group of bacteria are to be found inter alia in Seiler (Journal of General Microbiology 129, 1433-1477 (1983)), Kinoshita (1985, Glutamic Acid Bacteria, pp 115-142. In: Demain and Solomon (ed), Biology of Industrial Microorganisms. The Benjamin/Cummins Publishing Co., London, UK), Kämpfer and Kroppenstedt (Canadian Journal of Microbiology 42, 989-1005 (1996)), Liebl et al. (International Journal of Systematic Bacteriology 41, 255-260 (1991)) and in U.S. Pat. No. 5,250,434.

Strains with the designation "ATCC" can be purchased from the American Type Culture Collection (Manassas, Va., USA). Strains with the designation "DSM" can be purchased from the Deutsche Sammlung of Mikroorganismen and Zellkulturen (DSMZ, Brunswick, Germany). Strains with the designation "NRRL" can be purchased from the Agricultural Research Service Patent Culture Collection (ARS, Peoria, Ill., US). Strains with the designation "FERM" can be purchased from National Institute of Advanced Industrial Science and Technology (AIST Tsukuba Central 6, 1-1-1 Higashi, Tsukuba Ibaraki, Japan).

The polypeptide encoded by the prpD1 gene and having 2-methylcitrate dehydratase activity (PrpD1) is allocated the EC number 4.2.1.79 in accordance with the nomenclature of the IUPAC (International Union of Pure and Applied Chemistry).

Chemically, a gene is a polynucleotide. Another term for this is nucleic acid.

"Proteinogenic amino acids" mean the amino acids which occur in natural proteins, that is to say in proteins of microorganisms, plants, animals and humans. In connection with the present invention, proteinogenic amino acids means the group of L-amino acids consisting of L-aspartic acid, L-asparagine, L-threonine, L-serine, L-glutamic acid, L-glutamine, glycine, L-alanine, L-cysteine, L-valine, L-methionine, L-isoleucine, L-leucine, L-tyrosine, L-phenylalanine, L-histidine, L-lysine, L-tryptophan, L-proline and L-arginine and, where appropriate, L-selenocysteine. The L-amino acids likewise include L-homoserine.

The mutants according to the invention preferably secrete the stated proteinogenic amino acids, preferably L-lysine, L-tryptophan, L-valine, L-isoleucine or L-homoserine. The term "amino acid" also includes salts thereof such as, for example, lysine monohydrochloride or lysine sulphate in the case of the amino acid L-lysine.

In one embodiment, mutants of coryneform bacteria comprise a prpD1 allele which codes for a polypeptide having 2-methylcitrate dehydratase enzymic activity which comprises the amino acid sequence of SEQ ID NO: 2, with one of the proteinogenic amino acids except L-proline being present at position 272. The exchange of L-proline for L-leucine is preferred.

In another embodiment, mutants of coryneform bacteria comprise a prpD1 allele which codes for a polypeptide having 2-methylcitrate dehydratase enzymic activity, which comprises a proteinogenic amino acid except L-proline, preferably L-leucine, at the position corresponding to position 272 of the amino acid sequence of SEQ ID NO:2, where the gene comprises a nucleotide sequence which is identical to the nucleotide sequence of a polynucleotide which is obtainable by a polymerase chain reaction (PCR) using a primer pair whose nucleotide sequences in each case include at least 15 consecutive nucleotides which are selected from the nucleotide sequence between position 1 and 750 of SEQ ID NO:3 or SEQ ID NO:7 and from the complementary nucleotide sequence between position 2245 and 3000 of SEQ ID NO:3 or SEQ ID NO:7. An example of such a suitable primer pair is depicted in SEQ ID NO:9 and SEQ ID NO:10. Preferred starting material ("template" DNA) is chromosomal DNA of coryneform bacteria which have been treated with a mutagen. The chromosomal DNA is more preferably of the genus *Corynebacterium* and more preferably that of the species *Corynebacterium glutamicum*.

In another embodiment, mutants of coryneform bacteria comprise a prpD1 allele which codes for a polypeptide having 2-methylcitrate dehydratase enzymic activity, which comprises an amino acid sequence with a length corresponding to 498 L-amino acids, with one of the proteinogenic amino acids except L-proline, preferably L-leucine, being present at position 272.

In another embodiment, mutants of coryneform bacteria comprise a prpD1 allele which codes for a polypeptide having 2-methylcitrate dehydratase enzymic activity, which comprises at position 252 to 291 of the amino acid sequence the amino acid sequence corresponding to position 252 to 291 of SEQ ID NO:6 or 8. The amino acid sequence of the encoded polypeptide preferably comprises an amino acid sequence corresponding to position 202 to 341 of SEQ ID NO:6 or 8 or position 152 to 391 of SEQ ID NO:6 or 8 or position 102 to 441 of SEQ ID NO:6 or 8 or position 52 to 491 of SEQ ID NO:6 or 8 or position 2 to 495 of SEQ ID NO:6 or 8 or position 2 to 496 of SEQ ID NO:6 or 8 or position 2 to 497 of SEQ ID NO:6 or 8. The length of the encoded polypeptide is preferably 498 amino acids.

In another embodiment, mutants of coryneform bacteria comprise a prpD1 allele which codes for a polypeptide having 2-methylcitrate dehydratase enzymic activity, which comprises at position 272 or at the corresponding position of the amino acid sequence a proteinogenic amino acid except L-proline, preferably exchange for L-leucine, and whose amino acid sequence is additionally at least 90%, preferably at least 92% or at least 94% or at least 96%, and more preferably at least 97% or at least 98% or at least 99% identical to the amino acid sequence of SEQ ID NO:6 or SEQ ID NO:8.

In a different embodiment, mutants of coryneform bacteria comprise a prpD1 allele which codes for a polypeptide having 2-methylcitrate dehydratase enzymic activity, which comprises at position 272 or at the corresponding position of the amino acid sequence a proteinogenic amino acid except L-proline, preferably exchange for L-leucine, and whose nucleotide sequence is additionally at least 90%, preferably at least 92% or at least 94% or at least 96%, and more preferably at least 97% or at least 98% or at least 99% identical to the nucleotide sequence of SEQ ID NO:5.

It is known that conservative amino acid exchanges alter the enzymic activity only insubstantially. The prpD1 allele which is present in the mutants according to the invention and which codes for a polypeptide having 2-methylcitrate dehydratase enzymic activity may, in addition to the amino acid sequence shown in SEQ ID NO:6 or SEQ ID NO:8, comprise one (1) or more conservative amino acid exchange(s). The polypeptide preferably comprises not more than two (2), not more than three (3), not more than four (4) or not more than five (5) conservative amino acid exchanges. The enzymatic activity is substantially unaffected by such conservative amino acid exchanges.

In the case of aromatic amino acids, mutual exchanges of phenylalanine, tryptophan and tyrosine are referred to as conservative exchanges. In the case of hydrophobic amino acids, mutual exchanges of leucine, isoleucine and valine are referred to as conservative exchanges. In the case of polar amino acids, mutual exchanges of glutamine and asparagine are referred to as conservative exchanges. In the case of basic amino acids, mutual exchanges of arginine, lysine and histidine are referred to as conservative exchanges. In the case of acidic amino acids, mutual exchanges of aspartic acid and glutamic acid are referred to as conservative exchanges. In the case of amino acids comprising hydroxyl groups, mutual exchanges of serine and threonine are referred to as conservative exchanges.

When working on the present invention, it was found by comparing the amino acid sequence using the Clustal program (Thompson et al., Nucleic Acids Research 22, 4637-4680 (1994)) that the amino acid sequences of the 2-methylcitrate dehydratase of different bacteria such as, for example, *Mycobacterium tuberculosis, Mycobacterium bovis, Corynebacterium efficiens* and *Corynebacterium glutamicum* comprise a sequence motif consisting of the sequence Arg-Glu-Leu-Asp-Phe-His-Asp-Thr-Phe-Leu-Ala-Ala-Asp/Glu-Tyr-Ser-His-Pro (SEQ ID NO:21), a sequence motif consisting of the sequence Gly-Ile-Cys-Leu-His-Glu-His-Lys-Ile-Asp-His-Val-Ala-His-Leu-Gly-Pro (SEQ ID NO:22) and also a sequence motif consisting of the sequence Pro-Ala-Pro-Ile-Trp-Glu-Gly-Glu-Asp-Gly-Val-Ile-Ala-Trp-Leu-Leu (SEQ ID NO:23). The designation "Asp/Glu" means that "Asp or Glu" may be present at the corresponding position.

Accordingly, preferred mutants of coryneform bacteria are those comprising a prpD1 allele which codes for a polypeptide having 2-methylcitrate dehydratase enzymic activity, which comprises at least one amino acid sequence selected from the group of Arg-Glu-Leu-Asp-Phe-His-Asp-Thr-Phe-Leu-Ala-Ala-Asp/Glu-Tyr-Ser-His-Pro (SEQ ID NO:21), Gly-Ile-Cys-Leu-His-Glu-His-Lys-Ile-Asp-His-Val-Ala-His-Leu-Gly-Pro (SEQ ID NO:22) and Pro-Ala-Pro-Ile-Trp-Glu-Gly-Glu-Asp-Gly-Val-Ile-Ala-Trp-Leu-Leu (SEQ ID NO:23), and comprises at position 272 or at the corresponding or comparable position of the amino acid sequence one of the proteinogenic amino acids except L-proline, preferably L-leucine.

The amino acid sequence motif Arg-Glu-Leu-Asp-Phe-His-Asp-Thr-Phe-Leu-Ala-Ala-Asp/Glu-Tyr-Ser-His-Pro (SEQ ID NO:21) is present for example in SEQ ID NO:2 and 4 or 6 and 8 from position 102 to 118. The amino acid sequence motif Gly-Ile-Cys-Leu-His-Glu-His-Lys-Ile-Asp-His-Val-Ala-His-Leu-Gly-Pro (SEQ ID NO:22) is present for example in SEQ ID NO:2 and 4 or 6 and 8 from position 156 to 172. The amino acid sequence motif Pro-Ala-Pro-Ile-Trp-Glu-Gly-Glu-Asp-Gly-Val-Ile-Ala-Trp-Leu-Leu (SEQ ID NO:23) is present for example in SEQ ID NO:2 and 4 or 6 and 8 from position 240 to 255.

In another embodiment, the invention mutants of coryneform bacteria comprise a prpD1 allele which codes for a polypeptide having 2-methylcitrate dehydratase enzymic activity, which comprises the amino acid sequence of SEQ ID NO:6 or SEQ ID NO:8.

In another embodiment, mutants of coryneform bacteria comprise a prpD1 allele corresponding to SEQ ID NO:5 or SEQ ID NO:7.

It is known that the host's own enzymes called aminopeptidases delete the terminal methionine during the protein synthesis.

The expression "a position corresponding to position 272 of the amino acid sequence" or "a position comparable to position 272 of the amino acid sequence" means that through insertion or deletion of a codon coding for an amino acid in the N-terminal region (relative to position 272 of SEQ ID NO:6 or 8) of the encoded polypeptide the stated position and stated length is formally increased by one unit in the case of an insertion or is reduced by one unit in the case of a deletion. For example, deletion of the GAG codon coding for the amino acid L-glutamic acid at position 19 of SEQ ID NO:6 or 8 shifts the L-leucine from position 272 to position 271. The stated length would then be: 497 amino acids. In the same way, insertion or deletion of a codon coding for an amino acid in the C-terminal region (relative to position 272) of the encoded polypeptide formally increases the stated length by one unit in the case of an insertion or reduces it by one unit in the case of a deletion. Such comparable positions can easily be identified by comparing the amino acid sequences in the form of an alignment for example with the aid of the Clustal programme or of the MAFFT programme.

The enzymatic activity is substantially unaffected by such insertions and deletions. "Substantially unaffected" means that the enzymatic activity of said variants differs by not more than 10%, not more than 7.5%, not more than 5%, not more than 2.5% or not more than 1% from the activity of the polypeptide having the amino acid sequence of SEQ ID NO:6 or 8.

One method for determining the enzymatic activity of 2-methylcitrate dehydratase is described in Horswill and Escalante-Semerena (Biochemistry 40(15), 4703-4713 (2001)).

In another embodiment, prpD1 alleles code for polypeptide variants of SEQ ID NO:6 or 8 which comprise one or more insertion(s) or deletion(s). The polypeptide preferably comprises not more than 5, not more than 4, not more than 3 or not more than 2 insertions or deletions of amino acids.

The sequence motifs Arg-Glu-Leu-Asp-Phe-His-Asp-Thr-Phe-Leu-Ala-Ala-Asp/Glu-Tyr-Ser-His-Pro (SEQ ID NO:21), Gly-Ile-Cys-Leu-His-Glu-His-Lys-Ile-Asp-His-Val-Ala-His-Leu-Gly-Pro (SEQ ID NO:22) and Pro-Ala-Pro-Ile-Trp-Glu-Gly-Glu-Asp-Gly-Val-Ile-Ala-Trp-Leu-Leu (SEQ ID NO:23) are preferably not disrupted by such insertions/deletions.

Mutants can be produced by using conventional in-vivo mutagenesis methods with cell populations of coryneform bacteria using mutagenic substances such as, for example, N-methyl-N'-nitro-N-nitrosoguanidine (MNNG), ethyl methanesulphonate (EMS), 5-bromouracil or ultraviolet light. Mutagenesis methods are described for example in the Manual of Methods for General Bacteriology (Gerhard et al. (Eds.), American Society for Microbiology, Washington, D.C., USA, 1981) or in Tosaka et al. (Agricultural and Biological Chemistry 42(4), 745-752 (1978)) or in Konicek et al. (Folia Microbiologica 33, 337-343 (1988)). Mutageneses using MNNG include concentrations of from 50 to 500 mg/l or even higher concentrations up to a maximum of 1 g/l, an incubation time of from 1 to 30 minutes at a pH of from 5.5 to 7.5. Under these conditions, the number of viable cells is reduced by a proportion of approximately 50% to 90% or approximately 50% to 99% or approximately 50% to 99.9% or more.

Mutants or cells are removed from the mutagenized cell population and are propagated. In a further step, their ability to secrete amino acids, preferably L-lysine, L-tryptophan, L-valine, L-isoleucine or L-homoserine, in a batch culture using a suitable nutrient medium is preferably investigated. Suitable nutrient media and test conditions are described inter alia in U.S. Pat. No. 6,221,636, in U.S. Pat. No. 5,840,551, in U.S. Pat. No. 5,770,409, in U.S. Pat. No. 5,605,818, in U.S. Pat. No. 5,275,940 and in U.S. Pat. No. 4,224,409. In the case of uses of suitable robotic systems as described for example in Zimmermann et al. (VDI Berichte No. 1841, VDI-Verlag, Düsseldorf, Germany 2004, 439-443) or Zimmermann (Chemie Ingenenieur Technik 77 (4), 426-428 (2005)), numerous mutants can be investigated in a short time. A maximum of 3000, a maximum of 10 000, a maximum of 30 000 or also a maximum of 60 000 mutants, where appropriate also more, are investigated. Mutants which, compared with the parent strain or unmutagenized starting strain, secrete increased amino acids into the nutrient medium or into the interior of the cell are identified in this way. These include for example mutants whose amino acid secretion is increased by at least 0.5%.

DNA is then prepared or isolated from the mutants, and the corresponding polynucleotide is synthesized with the aid of the polymerase chain reaction using primer pairs which permit amplification of the prpD1 gene or of the prpD1 allele according to the invention or of the mutation according to the invention at position 272. The DNA is preferably isolated from mutants which secrete amino acids to an increased extent.

It is possible to select for this purpose any primer pairs from the nucleotide sequence located upstream and downstream of the mutation according to the invention, and the nucleotide sequence complementary thereto. One primer of a primer pair in this case preferably comprises at least 15, at least 18, at least 20, at least 21 or at least 24 consecutive nucleotides selected from the nucleotide sequence between position 1 and 1563 of SEQ ID NO:3 or SEQ ID NO:7. The second primer belonging to a primer pair includes at least 15, at least 18, at least 20, at least 21 or at least 24 consecutive nucleotides selected from the complementary nucleotide sequence between position 3000 and 1567 of SEQ ID NO:3 or SEQ ID NO:7. If amplification of the coding region is desired, the primer pair is preferably selected from the nucleotide sequence between position 1 and 750 of SEQ ID NO:3 or SEQ ID NO:7 and from the complementary nucleotide sequence between position 3000 and 2245 of SEQ ID NO:3 or SEQ ID NO:7. A suitable primer pair is for example the primer pair prpD1_XL_A1 and prpD1_XL_E1 represented by SEQ ID NO:9 and SEQ ID NO:10. A PCR product prepared using this primer pair is depicted in SEQ ID NO:13.

If amplification of part of the coding region, as depicted for example in SEQ ID NO:17 and 19, is desired, the primer pair is preferably selected from the nucleotide sequence between position 751 and 1563 of SEQ ID NO:3 or SEQ ID NO:7 and from the complementary nucleotide sequence between position 2244 and 1567 of SEQ ID NO:3 or SEQ ID NO:7.

The primer can moreover be equipped with recognition sites for restriction enzymes, with a biotin group or further accessories. The total length of the primer preferably does not exceed 30, 40, 50 or 60 nucleotides.

Polynucleotides are prepared by amplification of selected sequences, such as the prpD1 allele, from provided, for example chromosomal, DNA ("template DNA") by PCR amplification employing thermostable DNA polymerases. Examples of such DNA polymerases are the Taq polymerase from *Thermus aquaticus*, which is marketed inter alia by Qiagen (Hilden, Germany), the Vent polymerase from *Thermococcus litoralis*, which is marketed inter alia by New England Biolabs (Frankfurt, Germany) or the Pfu polymerase from *Pyrococcus furiosus*, which is marketed inter alia by Stratagene (La Jolla, USA). Polymerases having proof-reading activity are preferred. Proof-reading activity means that these polymerases are able to recognize incorrectly incorporated nucleotides and to eliminate the error by renewed polymerization (Lottspeich and Zorbas, Bioanalytik, Spektrum Akademischer Verlag, Heidelberg, Germany (1998)). Examples of polymerases having proof-reading activity are the Vent polymerase and the Pfu polymerase.

The conditions in the reaction mixture are set according to the manufacturer's information. The polymerases are supplied by the manufacturer together with the usual buffer which normally has concentrations of 10-100 mM Tris/HCl and 6-55 mM KCl at pH 7.5-9.3. Magnesium chloride is added in a concentration of 0.5-10 mM unless it is present in the buffer supplied by the manufacturer. In addition, deoxynucleoside triphosphates are added in a concentration of 0.1-16.6 mM to the reaction mixture. The primers are introduced into the reaction mixture in a final concentration of 0.1-3 μM, and the template DNA in the optimal case with $10^2$ to $10^5$ copies. It is also possible to employ $10^6$ to $10^7$ copies. The appropriate polymerase is added to the reaction mixture in an amount of 2-5 units. A reaction mixture has a volume of 20-100 μl.

Further additions which can be included in the reaction are bovine serum albumin, Tween 20, gelatin, glycerol, formamide or DMSO (Dieffenbach and Dveksler, PCR Primer—A Laboratory Manual, Cold Spring Harbor Laboratory Press, USA 1995).

A PCR run consists of three different, consecutively repeating temperature steps. At the outset, the reaction is started by raising the temperature to 92° C.-98° C. for 4 to 10 minutes in order to denature the introduced DNA. This is followed by repetitions firstly of a step for denaturation of the introduced DNA at approximately 92-98° C. for 10-60 seconds, then a step to bind the primers to the introduced DNA at a particular temperature which depends on the primers ("annealing temperature") and which, from experience, is 50° C. to 60° C. and can be calculated individually for each primer pair, for 10-60 seconds. Detailed information concerning this is to be found by the skilled person in Rychlik et al. (Nucleic Acids Research 18 (21): 6409-6412). This is subsequently followed by a synthesis step to extend the introduced primers ("extension") at the activity optimum indicated in each case for the polymerase, normally in the range from 73° C. to 67° C., preferably 72° C. to 68° C., depending on the polymerase. The duration of this extension step depends on the efficiency of the polymerase and length of the PCR product to be amplified. In a typical PCR, this step takes 0.5-8 minutes, preferably 2-4 minutes. These three steps are repeated 30 to 35 times, where appropriate up to 50 times. A final "extension" step of 4-10 minutes terminates the reaction. The polynucleotides prepared in this way are also referred to as amplicons; the term nucleic acid fragment is likewise in use.

A PCR product prepared using the primer pair prpD1_XL_A1/prpD1_XL_E1 (see SEQ ID NO:9 and SEQ ID NO:10) is depicted in SEQ ID NO:13.

Further instructions and information on PCR are to be found by the skilled person for example in the handbook "PCR-Strategies" (Innis, Felfand and Sninsky, Academic Press, Inc., 1995), in the handbook by Diefenbach and Dveksler "PCR Primer—a laboratory manual" (Cold Spring Harbor Laboratory Press, 1995), in the handbook by Gait "Oligonucleotide synthesis: A Practical Approach" (IRL Press, Oxford, UK, 1984) and in Newton and Graham "PCR" (Spektrum Akademischer Verlag, Heidelberg, Germany, 1994).

The nucleotide sequence is subsequently determined for example by the chain termination method of Sanger et al. (Proceedings of the National Academies of Sciences, U.S.A., 74, 5463-5467 (1977)) with the modifications indicated by Zimmermann et al. (Nucleic Acids Research 18, 1067 (1990)), and the polypeptide encoded by this nucleotide sequence is analysed in particular in relation to the amino acid sequence. For this purpose, the nucleotide sequence is entered into a program for translating DNA sequence into an amino acid sequence. Suitable programs are for example the "Patentin" program which is obtainable from patent offices, for example the US Patent Office (USPTO), or the "Translate Tool" which is available on the ExPASy Proteomics Server in the World Wide Web (Gasteiger et al., Nucleic Acids Research 31, 3784-3788 (2003)).

Mutants whose prpD1 alleles code for polypeptides having 2-methylcitrate dehydratase enzymic activity, which comprise at position 272 of the amino acid sequence, or the corresponding or comparable position, one of the proteinogenic amino acids except L-proline, are identified in this way. Exchange for L-leucine is preferred.

The complete chromosome of the mutant is determined where appropriate. It is possible in this connection to employ the method described by Margulies et al. (Nature, 437(7057): 376-2720 (2005)) and Velicer et al. (Proceedings of the National Academy of Sciences, U.S.A., 103(21), 8107-8112 (2006)) which is known to those skilled in the art by the phrase "pyro-sequencing" and enables complete genomes to be sequenced rapidly.

In one aspect of the invention, a mutant of a coryneform bacterium is obtainable by:

a) treatment of a coryneform bacterium which has the ability to secrete amino acids with a mutagenic agent, b) isolation and propagation of the mutant generated in a), c) preferably determination of the ability of the mutant to secrete in a medium, or enrich in the interior of the cell, at least 0.5% more amino acid than the coryneform bacterium employed in a), d) preparation of nucleic acid from the mutant obtained in b), e) preparation of a nucleic acid molecule (or amplicon or nucleic acid fragment) using the polymerase chain reaction, of the nucleic acid from d), and of a primer pair consisting of a first primer including at least 15 consecutive nucleotides selected from the nucleotide sequence between position 1 and 1563, preferably 1 to 750 of SEQ ID NO:3 or SEQ ID NO:7 and a second primer including at least 15 consecutive nucleotides selected from the complementary nucleotide sequence between position 3000 and 1567, preferably 3000 and 2245 of SEQ ID NO:3 or 7, f) determination of the nucleotide sequence of the nucleic acid molecule obtained in e), and determination of the encoded amino acid sequence, g) where appropriate comparison of the amino acid sequence determined in f) with SEQ ID NO:6 or 8, and h) identification of a mutant which comprises a polynucleotide which codes for a polypeptide which comprises at position 272 or at comparable position one of the proteinogenic amino acids except L-proline, preferably L-leucine.

Generated mutants may comprise one (1) copy of the described prpD1 allele.

SEQ ID NO:5 represents by way of example the coding region of the prpD1 allele of a mutant. The coding region of the wild-type gene is represented as SEQ ID NO:1. SEQ ID NO:1 comprises at position 814 the nucleobase cytosine, at position 815 the nucleobase cytosine and at position 816 the nucleobase cytosine. SEQ ID NO:1 thus comprises from position 814 to 816 the CCC codon coding for the amino acid L-proline. SEQ ID NO:5 comprises at position 815 the nucleobase thymine. This cytosine-thymine transition results at position 814 to 816 in the CTC codon coding for the amino acid L-leucine.

In addition, the nucleotide sequences depicted in SEQ ID NO: 5 and 7 may comprise further base exchanges which have resulted from the mutagenesis treatment but are not expressed by an altered amino acid sequence. Mutations of this type are also referred to by those skilled in the art as silent or neutral mutations. These silent mutations may likewise already be present in the coryneform bacterium employed for the metagenesis treatment.

The coryneform bacteria used for the mutagenesis preferably already have the ability to secrete the desired amino acid into the nutrient medium or fermentation broth surrounding them, and/or enrich it in the interior of the cells.

L-Lysine-producing coryneform bacteria may have a feedback-resistant or desensitized aspartate kinase. Feedback-resistant aspartate kinases mean aspartate kinases (LysC) which by comparison with the wild form exhibit less sensitivity to inhibition by mixtures of lysine and threonine or mixtures of AEC (aminoethylcysteine) and threonine or lysine alone or AEC alone. The genes or alleles coding for these desensitized aspartate kinases are also referred to as lysC$^{FBR}$ alleles. Numerous lysC$^{FBR}$ alleles are described in the state of the art and code for aspartate kinase variants which have amino acid exchanges by comparison with the wild-type protein. The coding region of the wild-type lysC gene of *Corynebacterium glutamicum* corresponding to the access number AX756575 of the NCBI database is depicted in SEQ ID NO:11, and the polypeptide encoded by this gene is depicted in SEQ ID NO:12.

The L-lysine-producing coryneform bacteria employed for the measures of the invention preferably have a lysC allele which codes for an aspartate kinase variant which has the amino acid sequence of SEQ ID NO:12, the latter including one or more of the amino acid exchanges selected from the group:

LysC A279T (L-alanine at position 279 of the encoded aspartate kinase protein according to SEQ ID NO: 12 exchanged for L-threonine; see U.S. Pat. No. 5,688,671 and access numbers E06825, E06826, E08178 and I74588 to I74597), LysC A279V (L-alanine at position 279 of the encoded aspartate kinase protein according to SEQ ID NO: 12 exchanged for L-valine, see JP 6-261766 and access number E08179), LysC L297Q (L-leucine at position 297 of the encoded aspartate kinase protein according to SEQ ID NO: 12 exchanged for L-glutamine; see DE 102006026328, LysC S301F (L-serine at position 301 of the encoded aspartate kinase protein according to SEQ ID NO: 12 exchanged for L-phenylalanine; see U.S. Pat. No. 6,844,176 and access number E08180), LysC S301Y (L-serine at position 301 of the encoded aspartate kinase protein according to SEQ ID NO: 12 exchanged for L-tyrosine, see Kalinowski et al. (Molecular and General Genetics 224, 317-324 (1990)) and access number X57226), LysC T308I (L-threonine at position 308 of the encoded aspartate kinase protein according to SEQ ID NO: 12 exchanged for L-isoleucine; see JP 6-261766 and access number E08181)

LysC T311I (L-threonine at position 311 of the encoded aspartate kinase protein according to SEQ ID NO: 12 exchanged for L-isoleucine; see WO 00/632728 and U.S. Pat. No. 6,893,848), LysC S317A (L-serine at position 317 of the encoded aspartate kinase protein according to SEQ ID NO: 12 exchanged for L-alanine; see U.S. Pat. No. 5,688,671 and access number I74589), LysC R320G (L-arginine at position 320 of the encoded aspartate kinase protein according to SEQ ID NO: 12 exchanged for glycine; see Jetten et al. (Applied Microbiology and Biotechnology 43, 76-82 (995)) and access number L27125), LysC G345D (glycine at position 345 of the encoded aspartate kinase protein according to SEQ ID NO: 12 exchanged for L-aspartic acid; see Jetten et al. (Applied Microbiology and Biotechnology 43, 76-82 (995)) and access number L16848), LysC T380I (L-threonine at position 380 of the encoded aspartate kinase protein according to SEQ ID NO: 12 exchanged for L-isoleucine; see WO 01/49854 and access number AX192358), and LysC S381F (L-serine at position 381 of the encoded aspartate kinase protein according to SEQ ID NO: 12 exchanged for L-phenylalanine; see EP 0435132).

The lysC$^{FBR}$ allele lysC T311I (threonine at position 311 of the encoded aspartate kinase protein according to SEQ ID NO: 12 exchanged for isoleucine) and a lysC$^{FBR}$ allele comprising at least one exchange selected from the group of a A279T (alanine at position 279 of the encoded aspartate kinase protein according to SEQ ID NO: 12 exchanged for threonine), S381F (serine at position 381 of the encoded aspartate kinase protein according to SEQ ID NO: 12 exchanged for phenylalanine) and S317A (serine at position 317 of the encoded aspartate kinase protein according to SEQ ID NO: 12 exchanged for alanine) are prepared.

The lysC$^{FBR}$ allele lysC T311I (threonine at position 311 of the encoded aspartate kinase protein according to SEQ ID NO: 12 exchanged for isoleucine) is more preferred.

The strain DSM 16833 (WO 06/063660) has, just like the strain ATCC 21543 (U.S. Pat. No. 3,708,395), a lysC$^{FBR}$ allele which codes for an aspartate kinase protein which comprises the amino acid exchange T311I.

The strain NRRL B-11474 (U.S. Pat. No. 4,275,157) has a lysC$^{FBR}$ allele which codes for an aspartate kinase protein which comprises the amino acid exchanges A279T and S381F.

Starting from the strain ATCC 21543, a mutant designated DM1916 which comprises a prpD1 allele which codes for a polypeptide in which L-leucine is present at position 272 of the amino acid sequence was isolated. The nucleotide sequence of the coding region of the prpD1 allele of the mutant DM1916 is depicted as SEQ ID NO:5 and the amino acid sequence of the encoded polypeptide is depicted as SEQ ID NO:6 or 8.

It is additionally possible to use L-lysine-secreting coryneform bacteria which have known properties.

L-Tryptophan-producing coryneform bacteria may have a feedback-resistant or desensitized anthranilate synthase. Feedback-resistant anthranilate synthase (TrpE) means anthranilate synthases which, by comparison with the wild form, have a sensitivity to inhibition by tryptophan or 5-fluorotryptophan (Matsui et al., Journal of Bacteriology 169 (11): 5330-5332 (1987)) or similar analogues which is less by at least 5 to 10%, or at least 10% to 15% or at least 10% to 20%. The genes or alleles coding for these desensitized anthranilate synthases are also referred to as trpE$^{FBR}$ alleles. Examples of such mutants and alleles are for example described in U.S. Pat. No. 6,180,373 and EP338474.

L-Valine-producing coryneform bacteria may have a feedback-resistant or desensitized acetolactate synthase (acetohydroxyacid synthase) [EC No. 2.2.1.6].

Feedback-resistant acetolactate synthase means an acetolactate synthase which, by comparison with the wild form, shows a lower sensitivity to inhibition by one or more of the amino acids selected from the group of L-valine, L-isoleucine and L-leucine, preferably L-valine.

The acetolactate synthase (IlvB, IlvN) of *Corynebacterium* consists of a so-called large subunit encoded by the ilvB gene and of a so-called small subunit encoded by the ilvN gene (Keilhauer et al., Journal of Bacteriology 175(17), 5595-5603 (1993)). WO 05/003357 and Elisakova et al. (Applied and Environmental Microbiology 71(1):207-13 (2005)) report on variants of the IlvN subunit which confer resistance to L-valine, L-isoleucine and L-leucine on the acetolactate synthase. One variant comprises at position 21 of the amino acid sequence L-aspartic acid instead of L-isoleucine (IlvN I21D) and at position 22 L-phenylalanine instead of L-isoleucine (IlvN I22F). The second variant comprises at position 20 of the amino acid sequence L-aspartic acid instead of glycine (IlvN G20D), at position 21 of the amino acid sequence L-aspartic acid instead of L-isoleucine (IlvN I21D) and at position 22 L-phenylalanine instead of L-isoleucine (IlvN I22F).

L-Isoleucine-producing coryneform bacteria may have a feedback-resistant or desensitized threonine dehydratase (=threonine deaminase).

Feedback-resistant threonine dehydratase means a threonine dehydratase (EC No. 4.3.1.19) which, by comparison with the wild form, shows a lower sensitivity to inhibition by L-isoleucine. The genes or alleles coding for this desensitized threonine dehydratase are also referred to as ilvA$^{FBR}$ alleles.

The coding region of the wild-type ilvA gene of *Corynebacterium glutamicum* corresponding to access number L01508 of the NCBI database is depicted in SEQ ID NO:17 and the polypeptide encoded by this gene is depicted in SEQ ID NO:18.

The threonine dehydratase variants described in U.S. Pat. No. 6,107,063 and in Morbach et al. (Applied and Environmental Microbiology 61 (12), 4315-4320 (1995)) comprise one or more of the amino acid exchanges selected from the group:

IlvA M199V (L-methionine at position 199 of the encoded threonine dehydratase protein according to SEQ ID NO: 18 exchanged for L-valine; see U.S. Pat. No. 6,107,063), IlvA A257G (L-alanine at position 257 of the encoded threonine dehydratase protein according to SEQ ID NO: 18 exchanged for L-arginine; see U.S. Pat. No. 6,107,063), IlvA H278R (L-histidine at position 278 of the encoded threonine dehydratase protein according to SEQ ID NO: 18 exchanged for L-arginine; see U.S. Pat. No. 6,107,063), IlvA V323A (L-valine at position 323 of the encoded threonine dehydratase protein according to SEQ ID NO: 18 exchanged for L-alanine; see Morbach et al.), IlvA L351S (L-leucine at position 351 of the encoded threonine dehydratase protein according to SEQ ID NO: 18 exchanged for L-serine; see U.S. Pat. No. 6,107,063)

IlvA D378G (L-aspartic acid at position 378 of the encoded threonine dehydratase protein according to SEQ ID NO: 18 exchanged for glycine; see Morbach et al.)

The resulting mutants show, by comparison with the starting strain or parent strain employed, increased excretion or production of the desired amino acid in a fermentation process.

In one embodiment, an isolated polynucleotide codes for a polypeptide having 2-methylcitrate dehydratase enzymic activity, which comprises at position 272 or at a corresponding or comparable position of the amino acid sequence a proteinogenic amino acid except L-proline, with exchange for L-leucine being preferred.

The polynucleotide according to the invention can be isolated from a mutant according to the invention.

It is additionally possible to employ in vitro methods for the mutagenesis of the prpD1 gene. On use of in vitro methods, isolated polynucleotides which comprise a prpD1 gene of a coryneform bacterium, preferably the wild-type gene of *Corynebacterium glutamicum* described in the prior art, are subjected to a mutagenic treatment.

An isolated polynucleotides may be for example isolated total DNA or chromosomal DNA or else amplicons of the prpD1 gene which have been prepared with the aid of the polymerase chain reaction (PCR). Amplicons of this type are also referred to as PCR products. Instructions for amplifying DNA sequences with the aid of the polymerase chain reaction are to be found by the skilled person inter alia in the handbook by Gait: Oligonucleotide Synthesis: A Practical Approach (IRL Press, Oxford, UK, 1984) and in Newton and Graham: PCR (Spektrum Akademischer Verlag, Heidelberg, Germany, 1994). It is likewise possible for the prpD1 gene which is to be mutagenized firstly to be incorporated into a vector, for example into a bacteriophage or into a plasmid.

Suitable methods for in vitro mutagenesis are inter alia treatment with hydroxylamine according to Miller (Miller, J. H.: A Short Course in Bacterial Genetics. A Laboratory Manual and Handbook for *Escherichia coli* and Related Bacteria, Cold Spring Harbor Laboratory Press, Cold Spring Harbor, 1992), the use of mutagenic oligonucleotides (T. A. Brown: Gentechnologie für Einsteiger, Spektrum Akademischer Verlag, Heidelberg, 1993 and R. M. Horton: PCR-Mediated Recombination and Mutagenesis, Molecular Biotechnology 3, 93-99 (1995)) and the use of a polymerase chain reaction utilizing a DNA polymerase which shows a high error rate. A DNA polymerase of this type is for example the Mutazyme DNA polymerase (GeneMorph PCR Mutagenesis Kit, No. 600550) from Stratagene (LaJolla, Calif., USA).

Further instructions and reviews on the generation of mutations in vivo or in vitro can be found in the prior art and known textbooks of genetics and molecular biology such as, for example, the textbook of Knippers ("Molekulare Genetik", 6th edition, Georg Thieme Verlag, Stuttgart, Germany, 1995), that of Winnacker ("Gene and Klone", VCH Verlagsgesellschaft, Weinheim, Germany, 1990) or that of Hagemann ("Allgemeine Genetik", Gustav Fischer Verlag, Stuttgart, 1986).

In another embodiment, an isolated polynucleotide codes for a polypeptide having 2-methylcitrate dehydratase enzymic activity, which comprises the amino acid sequence of SEQ ID NO:2, with one of the proteinogenic amino acids except L-proline being present at position 272 of the amino acid sequence. Exchange for L-leucine is preferred.

In another embodiment, an isolated polynucleotide codes for a polypeptide having 2-methylcitrate dehydratase enzymic activity, which comprises an amino acid sequence with a length of 498 amino acids, and where a proteinogenic L-amino acids except L-proline, preferably L-leucine, is present at position 272.

In another embodiment, an isolated polynucleotide codes for a polypeptide having 2-methylcitrate dehydratase enzymic activity, which comprises at position 252 to 291 of the amino acid sequence the amino acid sequence corresponding to position 252 to 291 of SEQ ID NO:6 or 8. The amino acid sequence of the encoded polypeptide preferably comprises an amino acid sequence corresponding to position 202 to 341 of SEQ ID NO:6 or 8 or position 152 to 391 of SEQ ID NO:6 or 8 or position 102 to 441 of SEQ ID NO:6 or 8 or position 52 to 491 of SEQ ID NO:6 or 8 or position 2 to 495 of SEQ ID NO:6 or 8 or position 2 to 496 of SEQ ID NO:6 or 8 or position 2 to 497 of SEQ ID NO:6 or 8. The length of the encoded polypeptide preferably is 498 amino acids.

In another embodiment, an isolated polynucleotide codes for a polypeptide having 2-methylcitrate dehydratase enzymic activity, which comprises at position 272 of the amino acid sequence or a corresponding or comparable position a proteinogenic amino acid except L-proline, preferably L-leucine, and which comprises a nucleotide sequence which is identical to the nucleotide sequence of a polynucleotide which is obtainable by polymerase chain reaction (PCR) using the primer pair whose nucleotide sequences in each case include at least 15 consecutive nucleotides which are selected from the nucleotide sequence between position 1 and 750 of SEQ ID NO:3 or SEQ ID NO:7 and from the complementary nucleotide sequence between position 3000 and 2245 of SEQ ID NO:3 or SEQ ID NO:7. One example of such a primer pair is depicted in SEQ ID NO:9 and SEQ ID NO:10. Preferred starting material ("template") DNA) is chromosomal DNA of coryneform bacteria which have been treated with a mutagen. The chromosomal DNA is preferably of the genus *Corynebacterium* and more preferably that of the species *Corynebacterium glutamicum*.

The invention further relates to an isolated polynucleotide which hybridizes with the nucleotide sequence complementary to SEQ ID NO:5 under stringent conditions and codes for a polypeptide having 2-methylcitrate dehydratase enzymic activity, which comprises at position 272 of the amino acid sequence or a corresponding or comparable position a proteinogenic amino acid except L-proline, preferably L-leucine.

Instructions for hybridizing nucleic acids or polynucleotides are to be found by the skilled person inter alia in the handbook "The DIG System Users Guide for Filter Hybridization" from Boehringer Mannheim GmbH (Mannheim, Germany, 1993) and in Liebl et al. (International Journal of Systematic Bacteriology 41: 255-260 (1991)). The hybridization takes place under stringent conditions, meaning that the only hybrids formed are those in which the probe, i.e. a polynucleotide including the nucleotide sequence complementary to SEQ ID NO:5, and the target sequence, i.e. the polynucleotides treated or identified with the probe, are at least 90% identical. It is known that the stringency of hybridization including the washing steps is influenced or determined by varying the buffer composition, the temperature and the salt concentration. The hybridization reaction is carried out at relatively low stringency compared with the washing steps (Hybaid Hybridisation Guide, Hybaid Limited, Teddington, UK, 1996).

It is possible to employ for the hybridization reaction for example a buffer corresponding to 5×SSC buffer at a temperature of approx. 50° C.-68° C. In this case, probes may also hybridize with polynucleotides which show less than 90% identity to the nucleotide sequence of the probe employed. Such hybrids are less stable and are removed by washing under stringent conditions. This can be achieved for example by reducing the salt concentration to 2×SSC and, where appropriate, subsequently 0.5×SSC (The DIG System User's Guide for Filter Hybridisation, Boehringer Mannheim, Mannheim, Germany, 1995), setting a temperature of approx. 50° C.-68° C., approx. 52° C.-68° C., approx. 54° C.-68° C., approx. 56° C.-68° C., approx. 58° C.-68° C., approx. 60° C.-68° C., approx. 62° C.-68° C., approx. 64° C.-68° C., approx. 66° C.-68° C. Temperature ranges of approx. 64° C.-68° C. or approx. 66° C.-68° C. are preferred. It is possible where appropriate to reduce the salt concentration to a concentration corresponding to 0.2×SSC or 0.1×SSC. The SSC buffer comprises where appropriate sodium dodecyl sulphate (SDS) in a concentration of 0.1%. It is possible by increasing the hybridization temperature stepwise in steps of approx. 1-2° C. from 50° C. to 68° C. to isolate polynucleotide fragments which have at least 90% or at least 91%, preferably at least 92% or at least 93% or at least 94% or at least 95% or at least 96% and more preferably at least 97% or at least 98% or at least 99% identity to the sequence or complementary sequence of the probe employed, and code for a polypeptide having 2-methylcitrate dehydratase enzymic activity, which comprises the amino acid exchange according to the invention. The nucleotide sequence of the polynucleotide obtained in this way is determined by known methods. Further instructions for hybridization are obtainable in the form of so-called kits on the market (e.g. DIG Easy Hyb from Roche Diagnostics GmbH, Mannheim, Germany, catalogue No. 1603558). The nucleotide sequences obtained in this way code for polypeptides having 2-methylcitrate dehydratase enzymic activity, which are at least 90%, preferably at least 92% or at least 94% or at least 96%, and very particularly preferably at least 97% or at least 98% or at least 99% identical to the amino acid sequence of SEQ ID NO:6 or SEQ ID NO:8 and comprise the amino acid exchange according to the invention.

In another embodiment, an isolated polynucleotide codes for a polypeptide having 2-methylcitrate dehydratase enzymic activity, which comprises at position 272 or a corresponding or comparable position of the amino acid sequence any amino acid except L-proline, with preference for exchange for L-leucine, and which includes an amino acid sequence which is additionally at least 90%, preferably at least 92% or at least 94% or at least 96%, and more preferably at least 97% or at least 98% or at least 99% identical to the amino acid sequence of SEQ ID NO:6 or SEQ ID NO:8.

In another embodiment, an isolated polynucleotide codes for a polypeptide having 2-methylcitrate dehydratase enzymic activity, which comprises at position 272 or a corresponding or comparable position of the amino acid sequence one of the proteinogenic amino acids except L-proline, with preference for exchange for L-leucine and which includes a nucleotide sequence which is additionally at least 90%, preferably at least 92% or at least 94% or at least 96%, and more preferably at least 97% or at least 98% or at least 99% identical to the nucleotide sequence of SEQ ID NO:5.

In addition, preferred isolated polynucleotides code for a polypeptide having 2-methylcitrate dehydratase enzymic activity, which comprises at position 272 of the amino acid sequence or a corresponding or comparable position a proteinogenic amino acid except L-proline, preferably L-leucine, and which comprise at least one sequence motif or an amino acid sequence selected from the group of Arg-Glu-Leu-Asp-Phe-His-Asp-Thr-Phe-Leu-Ala-Ala-Asp/Glu-Tyr-Ser-His-Pro (SEQ ID NO:21), Gly-Ile-Cys-Leu-His-Glu-His-Lys-Ile-Asp-His-Val-Ala-His-Leu-Gly-Pro (SEQ ID NO:22) and Pro-Ala-Pro-Ile-Trp-Glu-Gly-Glu-Asp-Gly-Val-Ile-Ala-Trp-Leu-Leu (SEQ ID NO:23).

The designations "Asp/Glu" mean that "Asp or Glu" may be present at the corresponding position.

In another embodiment, an isolated polynucleotide codes for a polypeptide having 2-methylcitrate dehydratase enzymic activity, which comprises the amino acid sequence of SEQ ID NO:6 or 8. The encoded polypeptide comprises where appropriate one (1) or more conservative amino acid exchange(s). The polypeptide preferably comprises not more than two (2), not more than three (3), not more than four (4) or not more than five (5) conservative amino acid exchanges.

In another embodiment, an isolated polynucleotide codes for a polypeptide having 2-methylcitrate dehydratase enzymic activity, which comprises the amino acid sequence of SEQ ID NO:6 or 8 comprising an extension at the N or C terminus by at least one (1) amino acid. This extension comprises not more than 50, 40, 30, 20, 10, 5, 3 or 2 amino acids or amino acid residues.

In another embodiment, prpD1 alleles code for polypeptide variants of SEQ ID NO:6 or 8, which comprise one or more insertions or deletions. These preferably comprise a maximum of 5, a maximum of 4, a maximum of 3 or a maximum of 2 insertions or deletions of amino acids. The sequence motif Arg-Glu-Leu-Asp-Phe-His-Asp-Thr-Phe-Leu-Ala-Ala-Asp/Glu-Tyr-Ser-His-Pro (SEQ ID NO:21) and/or Gly-Ile-Cys-Leu-His-Glu-His-Lys-Ile-Asp-His-Val-Ala-His-Leu-Gly-Pro (SEQ ID NO:22) and/or Pro-Ala-Pro-Ile-Trp-Glu-Gly-Glu-Asp-Gly-Val-Ile-Ala-Trp-Leu-Leu (SEQ ID NO:23) is/are preferably not disrupted by such insertions/deletions.

In another embodiment, an isolated polynucleotide includes the nucleotide sequence shown in SEQ ID NO:5 or 7.

In another embodiment, an isolated polynucleotide comprises the prpD1 allele of the mutant DM1916.

In another embodiment, an isolated polynucleotide comprises a part of the coding region of a prpD1 allele according to the invention, where the isolated polynucleotide comprises in every case the part of the coding region which comprises the amino acid exchange at position 272 of the amino acid sequence of the encoded polypeptide.

Included preferably is a nucleic acid molecule or DNA fragment which codes for at least one amino acid sequence corresponding to position 252 to 291 of SEQ ID NO:2, or which codes for at least one amino acid sequence corresponding to position 202 to 341 of SEQ ID NO:2, or which codes for at least one amino acid sequence corresponding to position 152 to 391 of SEQ ID NO:2, or which codes for at least one amino acid sequence corresponding to position 102 to 441 of SEQ ID NO:2, or which codes for at least one amino acid sequence corresponding to position 52 to 491 of SEQ ID NO:2, or which codes for at least one amino acid sequence corresponding to position 2 to 495 of SEQ ID NO:2, or which codes for at least one amino acid sequence corresponding to position 2 to 496 of SEQ ID NO:2, or which codes for at least one amino acid sequence corresponding to position 2 to 497 of SEQ ID NO:2, where one of the proteinogenic amino acids except L-proline, preferably L-leucine, is present at the position corresponding to 272 of SEQ ID NO:2.

One example of a reading frame includes a polynucleotide which codes for at least the amino acid sequence from position 252 to 291 corresponding to SEQ ID NO:2, where one of the proteinogenic amino acids (Xaa) except L-proline is present at the position corresponding to 272 of the amino acid sequence, is detailed below:

```
gcg tgg ctg tta tcg ggc aaa gat cat gtt tat cat
Ala Trp Leu Leu Ser Gly Lys Asp His Val Tyr His
            255                 260 gtg cca ttg ccg gaa cac ggc gag nnn aag ctg ggg
Val Pro Leu Pro Glu His Gly Glu Xaa Lys Leu Gly
        265             270                 275 att cta gag act tac aca aag gaa cat tca gcg gaa
Ile Leu Glu Thr Tyr Thr Lys Glu His Ser Ala Glu
                    280                 285 tat caa tcg cag
Tyr Gln Ser Gln
        290
```

It is depicted as SEQ ID NO:17. The amino acid sequence encoded by this reading frame is depicted as SEQ ID NO:18. Position 21 in SEQ ID NO:18 corresponds to position 272 of SEQ ID NO:2, 4, 6 or 8.

Preferred nucleic acid molecules code for at least one amino acid sequence corresponding to position 252 to 291 of SEQ ID NO:6 or 8, or at least corresponding to position 202 to 341 of SEQ ID NO: 6 or 8, or at least corresponding to position 152 to 391 of SEQ ID NO: 6 or 8, or at least corresponding to position 102 to 441 of SEQ ID NO: 6 or 8, or at least corresponding to position 52 to 491 of SEQ ID NO: 6 or 8, or at least corresponding to position 2 to 495 of SEQ ID NO: 6 or 8, or at least corresponding to position 2 to 496 of SEQ ID NO: 6 or 8, or at least corresponding to position 2 to 497 of SEQ ID NO: 6 or 8.

One example of a reading frame includes a polynucleotide which codes for at least the amino acid sequence corresponding to position 252 to 291 of SEQ ID NO:6 or 8, is detailed below:

```
gcg tgg ctg tta tcg ggc aaa gat cat gtt tat cat
Ala Trp Leu Leu Ser Gly Lys Asp His Val Tyr His
            255                 260 gtg cca ttg ccg gaa cac ggc gag ctc aag ctg ggg
Val Pro Leu Pro Glu His Gly Glu Leu Lys Leu Gly
        265             270                 275 att cta gag act tac aca aag gaa cat tca gcg gaa
Ile Leu Glu Thr Tyr Thr Lys Glu His Ser Ala Glu
                    280                 285 tat caa tcg cag
Tyr Gln Ser Gln
        290
```

The reading frame is likewise depicted as SEQ ID NO:19. SEQ ID NO:20 shows the amino acid sequence encoded by this reading frame. Position 21 in SEQ ID NO:20 corresponds to position 272 of SEQ ID NO:2, 4, 6 or 8.

More preferred nucleic acid molecules comprise at least a nucleotide sequence corresponding to position 1504 to 1623 of SEQ ID NO:7, or at least a nucleotide sequence corresponding to position 1354 to 1773 of SEQ ID NO: 7, or at least a nucleotide sequence corresponding to position 1204 to 1923 of SEQ ID NO:7, or at least a nucleotide sequence corresponding to position 1054 to 2073 of SEQ ID NO:7, or at least a nucleotide sequence corresponding to position 904 to 2223 of SEQ ID NO:7, or at least a nucleotide sequence corresponding to position 754 to 2235 of SEQ ID NO:7, or at least a nucleotide sequence corresponding to position 754 to 2238 of SEQ ID NO:7, or at least a nucleotide sequence corresponding to position 754 to 2241 of SEQ ID NO:7.

The reading frames, as shown by way of example in SEQ ID NO:17 and 19 as nucleotide sequence and in SEQ ID NO:18 and SEQ ID NO:20 in the form of the encoded amino acid sequence, may additionally comprise one or more mutations which lead to one or more conservative amino acid exchanges. The mutations preferably lead to a maximum of 4%, to a maximum of 2% or to a maximum of 1% conservative amino acid exchanges. The reading frames may further comprise one or more silent mutations. The reading frames preferably comprise not more than 4% and more preferably not more than 2% to not more than 1% silent mutations.

The isolated polynucleotides can be used to produce recombinant strains of microorganisms which, in an improved manner compared with the initial or parent strain, release amino acids into the medium surrounding them or accumulate them in the interior of cells.

A widespread method for incorporating mutations into genes of coryneform bacteria is that of allele exchange, which is also known under the name "gene replacement". In this method, a DNA fragment which comprises the mutation of interest is transferred into the desired strain of a coryneform bacterium, and the mutation is incorporated by at least two recombination events or crossover events into the chromosome of the desired strain, or the sequence of a gene present in the relevant strain is exchanged for the mutated sequence.

Schwarzer and Pühler (Bio/Technology 9, 84-87 (1991)) used this method in order to incorporate a lysA allele which harboured a deletion, and in order to incorporate a lysA allele which harboured an insertion, into the chromosome of *C. glutamicum* instead of the wild-type gene. Schäfer et al. (Gene 145, 69-73 (1994)) employed this method to incorporate a deletion into the hom-thrB operon of *C. glutamicum*. Nakagawa et al. (EP 1108790) and Ohnishi et al. (Applied Microbiology and Biotechnology 58(2), 217-223 (2002)) employed this method to incorporate various mutations starting from the isolated alleles into the chromosome of *C. glutamicum*. Nakagawa et al. were able in this way to incorporate a mutation referred to as Val59Ala into the homoserine dehydrogenase gene (hom), a mutation referred to as Thr311Ile into the aspartate kinase gene (lysC or ask), a mutation referred to as Pro458Ser into the pyruvate carboxylase gene (pyc) and a mutation referred to as Ala213Thr into the glucose-6-phosphate dehydrogenase gene (zwf) of *C. glutamicum* strains.

A polynucleotide which can be used for a method according to the invention comprises the complete region as shown for example in SEQ ID NO:5, or comprises part of the coding region such as, for example, the nucleotide sequence which codes for at least the amino acid sequence corresponding to position 252 to 291 of SEQ ID NO:6 or 8 and which is depicted as SEQ ID NO:17 and 19. The part of the coding region corresponding to SEQ ID NO:17 and 19 has a length of $\geq 120$ nucleobases. The parts of SEQ ID NO:7 which are preferred are those comprising at least the sequence between position 1354 and 1773, or at least between position 1204 and 1923, or at least between position 1054 and 2073, and correspondingly have a length of $\geq 420$, $\geq 720$ or $\geq 1020$ nucleobases.

The DNA fragment comprising the mutation of interest may be present in a vector, in particular a plasmid, which preferably undergoes only limited or no replication by the strain to be provided with the mutation. A bacterium of the genus *Escherichia*, preferably of the species *Escherichia coli*, is used as auxiliary or intermediate host in which the vector can be replicated.

Examples of such plasmid vectors are the pK*mob and pK*mobsacB vectors described by Schäfer et al. (Gene 145, 69-73 (1994)), such as, for example, pK18mobsacB, and the vectors described in WO 02/070685 and WO 03/014362.

These are replicative in *Escherichia coli*, but not in coryneform bacteria. Suitable vectors are those comprising a gene with a conditionally negatively dominant effect such as, for example, the sacB gene (laevan sucrase gene) of for example, *Bacillus* or the galK gene (galactose kinase gene) of, for example, *Escherichia coli*. (A gene with a conditionally negatively dominant effect means a gene which under certain conditions is disadvantageous, for example toxic, for the host but, under other conditions, has no negative effects on the host harbouring the gene.) These make it possible to select for recombination events in which the vector is eliminated from the chromosome. In addition, Nakamura et al. (U.S. Pat. No. 6,303,2723) described a temperature-sensitive plasmid for coryneform bacteria which is able to replicate only at temperatures below 31° C.

The vector is then transferred into the coryneform bacterium by conjugation, for example by the method of Schäfer (Journal of Bacteriology 172, 1663-1666 (1990)) or transformation for example by the method of Dunican and Shivnan (Bio/Technology 7, 1067-1070 (1989)) or the method of Thierbach et al. (Applied Microbiology and Biotechnology 29, 356-362 (1988)). The transfer of the DNA can where appropriate also be achieved by particle bombardment.

Homologous recombination by means of a first crossover event which brings about integration, and of a suitable second crossover event which brings about an excision in the target gene or in the target sequence achieves incorporation of the mutation and results in a recombinant bacterium.

Methods which can be employed for identifying and characterizing the resulting strains are inter alia those of Southern blotting hybridization, of the polymerase chain reaction, of sequence determination, the method of fluorescence resonance energy transfer (FRET) (Lay et al. Clinical Chemistry 43, 2262-2267 (1997)) or methods of enzymology.

The invention accordingly further relates to a method for producing a coryneform bacterium, in which a) a polynucleotide according to the invention is transferred into a coryneform bacterium, b) the 2-methylcitrate dehydratase gene which is present in the chromosome of the coryneform bacterium and which codes for an amino acid sequence with L-proline at position 272 or at a comparable position of the amino acid sequence is exchanged for the polynucleotide from a) which codes for an amino acid sequence which has at position 272 or at a comparable position of the amino acid sequence another proteinogenic L-amino acid, preferably L-leucine, and c) the coryneform bacterium obtained as in step a) and b) is propagated.

A recombinant coryneform bacterium which comprises instead of the wild-type prpD1 gene one (1) prpD1 allele according to the invention is obtained in this way.

A further method according to another embodiment for producing a microorganism comprises a) transferring a polynucleotide according to the invention which codes a polypeptide having 2-methylcitrate dehydratase enzymic activity into a microorganism, b) replicating the polynucleotide in the microorganism, and c) propagating the microorganism obtained as in step a) and b).

A recombinant microorganism which comprises at least one (1) copy or a plurality of copies of a polynucleotide which codes for a 2-methylcitrate dehydratase which comprises at position 272 or a comparable position of the amino acid sequence of the encoded polypeptide, one of the proteinogenic amino acids except L-proline, with preference for exchange for L-leucine, is obtained in this way.

In another aspect of the invention, hosts or host cells, preferably microorganisms, more preferably coryneform bacteria and bacteria of the genus *Escherichia*, comprise the polynucleotides according to the invention.

In another embodiment, microorganisms have been produced using the isolated polynucleotides. Microorganisms or bacteria of this type are also referred to as recombinant microorganisms or recombinant bacteria.

In another aspect of the invention, vectors comprise the polynucleotides according to the invention.

In another aspect of the invention, hosts comprise these vectors.

For improved production of L-amino acids, in particular L-lysine, L-tryptophan, L-valine, L-isoleucine and L-homoserine, overexpression of various genes in the mutants or recombinant strains may be obtained. The use of endogenous genes is preferred.

"Endogenous genes" or "endogenous nucleotide sequences" mean the genes or nucleotide sequences, or alleles, present in the population of a species.

Thus, to produce L-lysine, it is possible to overexpress one or more of the genes selected from the group of a dapA gene coding for a dihydrodipicolinate synthase (DapA, EC No. 4.2.1.52), such as, for example, the dapA gene described in EP 0 197 335 of the wild type of *Corynebacterium glutamicum*, a lysA gene coding for a diaminopimelate decarboxylase (LysA, EC No. 4.1.1.20), such as, for example, the lysA gene described in U.S. Pat. No. 6,090,597 of *Corynebacterium glutamicum* ATCC13869, a zwf gene coding for a glucose-6-phosphate dehydrogenase (Zwf, EC No. 1.1.1.49), such as, for example, the zwf gene described in JP-A-09224661 and EP-A-1108790 of the wild type of *Corynebacterium glutamicum*, the zwf alleles of *Corynebacterium glutamicum* which are described in US-2003-0175911-A1 and which code for a protein having glucose-6-phosphate dehydrogenase activity, in which for example the L-alanine at position 243 of the amino acid sequence is replaced by L-threonine, or in which the L-aspartic acid at position 245 is replaced by L-serine, a pyc gene coding for a pyruvate carboxylase (Pyc, EC No. 6.4.1.1), such as, for example, the pyc gene described in DE-A-198 31 609 and EP 1108790 of the wild type of *Corynebacterium glutamicum*, the pyc allele of *Corynebacterium glutamicum* which is described in EP 1 108 790 and which codes for a protein having pyruvate carboxylase activity in which L-proline at position 458 of the amino acid sequence is replaced by L-serine, the pyc alleles of *Corynebacterium glutamicum* which are described in WO 02/31158 and in particular EP1325135B1 and which code for proteins having pyruvate carboxylase activity which harbour one or more of the amino acid exchanges selected from the group of L-valine at position 1 replaced by L-methionine, L-glutamic acid at position 153 replaced by L-aspartic acid, L-alanine at position 182 replaced by L-serine, L-alanine at position 206 replaced by L-serine, L-histidine at position 227 replaced by L-arginine, L-alanine at position 455 replaced by glycine and L-aspartic acid at position 1120 replaced by L-glutamic acid, a lysC gene coding for an aspartate kinase (LysC, EC No. 2.7.2.4), such as, for example, the lysC gene described as SEQ ID NO:281 in EP-A-1108790 (see also access number AX120085 and 120365) and the lysC gene described as SEQ ID NO:25 in WO 01/00843 (see access number AX063743) of the wild type of *Corynebacterium glutamicum*, a lysC$^{FBR}$ allele coding for a feedback-resistant aspartate kinase variant, in particular corresponding to Table 1, a lysE gene coding for a lysine export protein (LysE), such as, for example, the lysE gene described in DE-A-195 48 222 of the wild-type *Corynebacterium glutamicum*, the aat gene coding for an aspartate aminotransferase (Aat, EC No. 2.6.1.1) (the aat gene of *Corynebacterium glutamicum* ATCC13032 is described for example in Kalinowski et al. (Journal of Biotechnology 104 (1-3), 5-25 (2003); see also access number NC_006958). It is referred to therein as aspB gene. In U.S. Pat. No. 6,004, 773, a gene coding for an aspartate aminotransferase is referred to as aspC. Marienhagen et al. (Journal of Bacteriology 187 (22), 7693-7646 (2005)) referred to the aat gene as aspT gene, and the zwa1 gene coding for the Zwa1 protein of the wild type of *Corynebacterium glutamicum* (U.S. Pat. No. 6,632, 644).

Overexpression means an increase in the intracellular concentration or activity of a ribonucleic acid, of a protein or of an enzyme. In one aspect of the invention, prpD1 alleles or polynucleotides code for 2-methylcitrate dehydratases which comprise at position 272 of the amino acid sequence of the encoded polypeptide a proteinogenic amino acid except L-proline, with preference for exchange for L-leucine, are overexpressed. It is known that N-terminal amino acids, preferably the N-terminal methionine, can be eliminated from the polypeptide formed, by the host's own enzymes—called aminopeptidases. The increase in the concentration or activity of a gene product can be achieved for example by increasing the copy number of the appropriate polynucleotides by at least one copy.

A widely used method for increasing the copy number comprises incorporating a gene or allele into a vector, preferably a plasmid, which is replicated by a coryneform bacterium. Plasmid vectors are for example pZ1 (Menkel et al., Applied and Environmental Microbiology (1989) 64: 549-554) or the pSELF vectors described by Tauch et al. (Journal of Biotechnology 99, 79-91 (2002)). A review article on the topic of plasmids in *Corynebacterium glutamicum* is to be found in Tauch et al. (Journal of Biotechnology 104, 27-40 (2003)).

Another method for achieving overexpression is the method of chromosomal gene amplification. In this method, at least one additional copy of the gene or allele of interest is introduced into the chromosome of a coryneform bacterium.

As described for example in Reinscheid et al. (Applied and Environmental Microbiology 60, 126-132 (1994)) for the hom-thrB operon, a plasmid which is non-replicative in *C. glutamicum* and which comprises the gene of interest is transferred into a coryneform bacterium. The strain resulting after homologous recombination by means of a crossover event comprises at least two copies of the relevant gene or allele.

As described in WO 03/040373 and US-2003-0219881-A1, one or more copy(ies) of the gene of interest is introduced by means of at least two recombination events into a desired site in the chromosome of *C. glutamicum*. In this way, for example, a copy of a lysC allele which codes for an L-lysine-insensitive aspartate kinase was incorporated into the gluB gene of *C. glutamicum*.

As described in WO 03/014330 and US-2004-0043458-A1, at least one further copy of the gene of interest is incorporated, preferably in tandem arrangement to the previously present gene or allele, at the natural site by means of at least two recombination events. In this way, for example, a tandem duplication of a lysC$^{FBR}$ allele was achieved at the natural lysC gene site.

It is possible to increase the copy number with the aid of transposons and IS elements (see: U.S. Pat. No. 5,804,414, U.S. Pat. No. 5,591,577).

A further method for achieving overexpression consists of linking a gene or allele in a functional manner (operably linked) to a promoter or to an expression cassette. Suitable promoters for *Corynebacterium glutamicum* are described for example in the review article by Patek et al. (Journal of Biotechnology 104(1-3), 311-323 (2003). It is possible to use the variants of the dapA promoter described by Vasicova et al. (Journal of Bacteriology 181, 6188-6191 (1999)), for example the promoter A25. A further possibility is to use the gap promoter of *Corynebacterium glutamicum* (EP 06007373). Also, the well-known promoters T3, T7, SP6, M13, lac, tac and trc described by Amann et al. (Gene 69(2), 301-315 (1988)) and Amann and Brosius (Gene 40(2-3), 183-190 (1985)) can be used.

It is possible to mutate the promoter region and regulatory region or the ribosome binding site which is located upstream of the structural gene. Expression is likewise improved by measures to prolong the lifespan of the mRNA. The enzymic activity is enhanced in addition by preventing breakdown of the enzyme protein. A further possible alternative is overexpression of the relevant gene or allele through alteration of the composition of the media and management of the culture.

The activity or concentration of a protein may be increased by the overexpression measures by at least 10%, 25%, 50%, 75%, 100%, 150%, 200%, 300%, 400% or 500%, maximally up to 1000% or 2000%, relative to the activity or concentration of the protein in the starting microorganism or parent strain. A starting microorganism or parent strain means a microorganism on which the measures of the invention are carried out.

The concentration of the protein can be determined by 1- and 2-dimensional protein gel fractionation and subsequent optical identification of the protein concentration using appropriate evaluation software in the gel. A method for preparing the protein gel in the case of coryneform bacteria and for identifying the proteins is the procedure described by Hermann et al. (Electrophoresis, 22:1712-23 (2001)). The protein concentration can likewise be determined by Western blot hybridization with an antibody specific for the protein to be detected (Sambrook et al., Molecular cloning: a laboratory manual. 2nd Ed. Cold Spring Harbor Laboratory Press, Cold Spring Harbor, N.Y., 1989) and subsequent optical evaluation with appropriate software to determine the concentration (Lohaus and Meyer (1998) Biospektrum 5:32-39; Lottspeich, Angewandte Chemie 272: 2630-2647 (1999)).

It may be possible for the production of L-lysine, besides the use of the alleles the prpD1 gene, where appropriate, with simultaneous overexpression of at least one of the genes selected from the aforementioned group of genes, simultaneously to attenuate or switch off one or more of the endogenous genes selected from the group consisting of a pgi gene coding for glucose-6-phosphate isomerase (Pgi, EC No. 5.3.1.9), such as, for example, the pgi gene described in U.S. Pat. No. 6,586,214 and U.S. Pat. No. 6,465,238 of *Corynebacterium glutamicum*, a hom gene coding for homoserine dehydrogenase (Hom, EC No. 1.1.1.3), such as, for example, the hom gene described in EP-A-0131171 of *Corynebacterium glutamicum*, a thrB gene coding for homoserine kinase (ThrB, EC No. 2.7.1.39), such as, for example, the thrB gene described by Peoples et al. (Molecular Microbiology 2 (1988): 63-72)) of *Corynebacterium glutamicum* and a pfkB gene coding for phosphofructokinase (PfkB, EC No. 2.7.1.56), such as, for example, the pfkB gene described in WO 01/00844 (sequence No. 57) of *Corynebacterium glutamicum*, an mdh gene coding for malate dehydrogenase (Mdh, EC No. 1.1.1.37) as described for example in WO 02/02778, an mqo gene coding for malate-quinone oxidoreductase (Mqo, EC No. 1.1.99.16), as described for example in U.S. Pat. No. 7,094,106 and PCT/EP2005/057216.

The term "attenuation" describes in this connection the reduction or switching off of the intracellular activity of one or more enzymes (proteins) in a microorganism which are encoded by the appropriate DNA, by for example using a weak promoter or using a gene or allele which codes for a corresponding enzyme with a low activity, or inactivates the corresponding gene or enzyme (protein) and, where appropriate, combining these measures.

The attenuation measures preferably reduce the activity or concentration of the corresponding protein to 0 to 75%, 0 to 50%, 0 to 25%, 0 to 10% or 0 to 5% of the activity or concentration of the wild-type protein, or of the activity or concentration of the protein in the starting microorganism.

Mutations for generating an attenuation may be transitions, transversions, insertions and deletions of at least one (1) base pair or nucleotide. Depending on the effect of the amino acid exchange caused by the mutation on the enzymic activity, reference is made to missense mutations or nonsense mutations. The missense mutation leads to exchange of a given amino acid in a protein for another one, the amino acid exchange being in particular a non-conservative one. This impairs the ability to function or activity of the protein and reduces it to a value of from 0 to 75%, 0 to 50%, 0 to 25%, 0 to 10% or 0 to 5%. The nonsense mutation leads to a stop codon in the coding region of the gene and thus to premature termination of translation. Insertions or deletions of at least one base pair in a gene lead to frame shift mutations which lead to incorrect amino acids being incorporated or the translation being terminated prematurely. If the mutation results in a stop codon in the coding region, this leads to premature termination of transation. The said measures are preferably carried out in the 5'-terminal part of the coding region which codes for the N terminus of the polypeptide. If the total length of a polypeptide (measured as number of chemically linked L-amino acids) is referred to as 100%, the part of the amino acid sequence belonging to the N terminus of the polypeptide—in the context of the present invention—comprises 80% of the L-amino acids following the start amino acid L-formylmethionine.

Further instructions for generating such mutations can be found in known textbooks of genetics and molecular biology such as, for example, the textbook by Knippers ("Molekulare Genetik", 6th edition, Georg Thieme Verlag, Stuttgart, Germany, 1995), that of Winnacker ("Gene and Klone", VCH Verlagsgesellschaft, Weinheim, Germany, 1990) or that of Hagemann ("Allgemeine Genetik", Gustav Fischer Verlag, Stuttgart, 1986). Further measures are described in the prior art.

One method for targeted reduction of gene expression consists of placing the gene to be attenuated under the control of a promoter which can be induced by addition of metered amounts of IPTG (isopropyl β-D-thiogalactopyranoside), such as, for example, the trc promoter or the tac promoter. Suitable for this purpose are vectors such as, for example, the *Escherichia coli* expressions vector pXK99E (WO0226787; deposited in accordance with the Budapest Treaty on 31 Jul.

2001 in DH5alpha/pXK99E as DSM14440 at the Deutsche Sammlung für Mikroorganismen and Zellkulturen (DSMZ, Brunswick, Germany)) or pVWEx2 (Wendisch, Ph. D. thesis, Berichte des Forschungszentrums Jülich, Jül-3397, ISSN 0994-2952, Jülich, Germany (1997)), which make IPTG-dependent expression of the cloned gene possible in *Corynebacterium glutamicum*.

This method has been employed for example in the Patent WO0226787 for the regulated expression of the deaD gene by integration of the vector pXK99EdeaD into the genome of *Corynebacterium glutamicum* and by Simic et al. (Applied and Environmental Microbiology 68: 3321-3327 (2002)) for the regulated expression of the glyA gene by integration of the vector pK18mobglyA' into *Corynebacterium glutamicum*.

A further method for reducing gene expression is the antisense technique, where short oligodeoxynucleotides or vectors are brought into the target cells to synthesize longer antisense RNA. The antisense RNA is able to bind there to complementary segments of specific mRNAs and reduce their stability, or block translatability. One example thereof is to be found in Srivastava et al. (Applied Environmental Microbiology 2000 October; 66 (10): 4366-4371).

The isolated coryneform bacteria obtained by the measures of the invention show a secretion or production of the desired amino acid in a fermentation process which is increased by comparison with the starting strain or parent strain employed.

Isolated bacteria mean the isolated and generated mutants and recombinant bacteria, preferably coryneform bacteria, which comprise a prpD1 allele which codes for a 2-methylcitrate dehydratase which comprises the described amino acid exchange at position 272 of the amino acid sequence.

The output of the isolated bacteria or of the fermentation process using bacteria in relation to one or more of parameters selected from the group of the product concentration (product per volume), the product yield (product formed per carbon source consumed) and the product formation (product formed per volume and time) or else other process parameters and combinations thereof is improved by at least 0.5%, at least 1%, at least 1.5% or at least 2% relative to the starting strain or parent strain or to the fermentation process.

The isolated coryneform bacteria according to the invention can be cultured continuously—as described for example in PCT/EP2004/008882—or discontinuously in a batch process (batch cultivation) or in fed or repeated fed batch processes for the purpose of producing L-amino acids. A summary of a general nature about known cultivation methods is available in the textbook by Chmiel (Bioprozesstechnik 1. Einführung in die Bioverfahrenstechnik (Gustav Fischer Verlag, Stuttgart, 1991)) or in the textbook by Storhas (Bioreaktoren and periphere Einrichtungen (Vieweg Verlag, Brunswick/Wiesbaden, 1994)).

The culture medium or fermentation medium to be used satisfies in a suitable manner the demands of the respective strains. Descriptions of culture media of various microorganisms are present in the handbook "Manual of Methods for General Bacteriology" of the American Society for Bacteriology (Washington D.C., USA, 1981). The terms culture medium, fermentation medium and nutrient medium or medium are mutually exchangeable.

Carbon sources which can be used are sugars and carbohydrates such as, for example, glucose, sucrose, lactose, fructose, maltose, molasses, sucrose-containing solutions from sugarbeet or sugarcane production, starch, starch hydrolysate and cellulose, oils and fats such as, for example, soya oil, sunflower oil, peanut oil and coconut fat, fatty acids such as, for example, palmitic acid, stearic acid and linoleic acid, alcohols such as, for example, glycerol, methanol and ethanol and organic acids such as, for example, acetic acid. These substances can be used singly or as mixture.

Nitrogen sources which can be used are organic nitrogen-containing compounds such as peptone, yeast extract, meat extract, malt extract, corn steep liquor, soybean flour and urea or inorganic compounds such as ammonium sulphate, ammonium chloride, ammonium phosphate, ammonium carbonate and ammonium nitrate. The nitrogen sources can be used singly or as mixture.

Phosphorus sources which can be used are phosphoric acid, potassium dihydrogen phosphate or dipotassium hydrogen phosphate or the corresponding sodium-containing salts.

The culture medium must additionally comprises salts for example in the form of chlorides or sulphates of metals such as, for example, sodium, potassium, magnesium, calcium and iron, such as, for example, magnesium sulphate or iron sulphate, which are necessary for growth. Finally, essential growth factors such as amino acids, for example homoserine and vitamins, for example thiamine, biotin or pantothenic acid, can be employed in addition to the abovementioned substances. It is moreover possible to add to the culture medium suitable precursors of the respective amino acid.

The said starting materials can be added to the culture in the form of a single batch or be fed during the culturing in a suitable manner.

To control the pH of the culture, basic compounds such as sodium hydroxide, potassium hydroxide, ammonia or aqueous ammonia or acidic compounds such as phosphoric acid or sulphuric acid are employed. The pH is adjusted to a value of from 6.0 to 9.0, preferably 6.5 to 8. To control foaming, it is possible to employ antifoams such as, for example, fatty acid polyglycol esters. To maintain the stability of plasmids, it is possible to add to the medium suitable selectively acting substances such as, for example, antibiotics. In order to maintain aerobic conditions, oxygen or oxygen-containing gas mixtures such as, for example, air are introduced into the culture. It is possible to use liquids enriched with hydrogen peroxide. The fermentation is carried out where appropriate with excess pressure, for example with an excess pressure of from 0.03 to 0.2 MPa. The temperature of the culture is 20° C. to 45° C. and preferably 25° C. to 40° C. In batch processes, the culturing is continued until a maximum of the desired amino acid has formed. This aim is normally reached within 10 hours to 160 hours. In continuous processes, longer culturing times are possible.

Fermentation media are described inter alia in U.S. Pat. No. 6,221,636, in U.S. Pat. No. 5,840,551, in U.S. Pat. No. 5,770,409, in U.S. Pat. No. 5,605,818, in U.S. Pat. No. 5,275,940, in U.S. Pat. No. 4,275,157 and in U.S. Pat. No. 4,224,409.

Methods for determining L-amino acids are known. The analysis can take place for example as described by Spackman et al. (Analytical Chemistry, 30, (1958), 1190) by anion exchange chromatography with subsequent ninhydrin derivatization, or by reversed phase HPLC as described by Lindroth et al. (Analytical Chemistry (1979) 51: 1167-1174).

In one aspect of the invention, a process for producing an L-amino acid in which
a) an isolated coryneform bacterium is fermented in a suitable medium, where the bacterium comprises a gene coding for a polypeptide having 2-methylcitrate dehydratase enzymic activity, where the L-proline at position 272 in the amino acid sequences of the polypeptide, or the corresponding position, is replaced by another proteinogenic amino acid, preferably L-leucine, and
b) the L-amino acid is accumulated in the fermentation broth or in the cells of the isolated coryneform bacterium.

This may be followed by collecting the L-amino acid which has accumulated in the nutrient medium or in the fermentation broth and/or in the cells of the bacteria in order to obtain a solid or liquid product.

A fermentation broth means a fermentation medium in which a microorganism has been cultured for a certain time and at a certain temperature. The fermentation medium, or the media employed during the fermentation, comprise(s) the substances and components ensuring growth of the microorganism and formation of the desired amino acid.

When the fermentation is complete, the resulting fermentation broth accordingly comprises a) the biomass of the microorganism which has been produced as a result of the growth of the cells of the microorganism, b) the desired amino acid formed during the fermentation, c) the organic by-products formed during the fermentation, and d) the constituents of the fermentation medium/media employed or of the starting materials such as, for example, vitamins such as biotin, amino acids such as homoserine or salts such as magnesium sulphate, which have not been consumed by the fermentation.

The organic by-products include substances which are produced by the microorganisms employed in the fermentation where appropriate in addition to the respective desired L-amino acid and are secreted where appropriate. These include L-amino acids which account for less than 30%, 20% or 10% compared with the desired amino acid. These further include organic acids which have one to three carboxyl groups, such as, for example, acetic acid, lactic acid, citric acid, malic acid or fumaric acid. Also included finally are sugars such as, for example, trehalose.

Fermentation broths suitable for industrial purposes may have an amino acid content of 30 g/kg to 200 g/kg or 40 g/kg to 180 g/kg or 50 g/kg to 150 g/kg. The biomass content (as dry biomass) may be 20 to 50 g/kg.

In the case of the amino acid L-lysine, substantially four different product forms are known in the state of the art.

One group of L-lysine-containing products includes concentrated aqueous alkaline solutions of purified L-lysine (EP-B-0534865). A second group as described for example in U.S. Pat. No. 6,340,486 and U.S. Pat. No. 6,465,025 includes aqueous acidic biomass-containing concentrates of L-lysine-containing fermentation broths. A third group of solid products includes powder or crystalline forms of purified or pure L-lysine which is preferably in the form of a salt such as, for example, L-lysine monohydrochloride. A fourth group of solid product forms is described for example in EP-B-0533039. Besides L-lysine, the product form described therein comprises most of the starting materials which were used during the fermentative production and were not consumed and, where appropriate, the biomass of the microorganism employed with a content of >0%-100%.

In case of the amino acids L-valine, L-isoleucine, L-proline, L-tryptophan and L-homoserine, known product forms are substantially those containing the relevant amino acids in purified or pure form ($\geq$95% by weight or $\geq$98% by weight).

Corresponding to the different product forms, a wide variety of processes are known with which the L-amino acid is collected, isolated or purified from the fermentation broth in order to produce the L-amino acid-containing product or the purified L-amino acid.

Solid pure L-amino acids may be produced by using methods of ion exchange chromatography, where appropriate with use of activated carbon, and methods of crystallization. In the case of lysine, the corresponding base or a corresponding salt such as, for example, the monohydrochloride (Lys-HCl) or lysine sulphate ($Lys_2$-$H_2SO_4$) is obtained in this way.

In case of lysine, EP-B-0534865 describes a process for producing aqueous, basic L-lysine-containing solutions from fermentation broths. In the process described therein, the biomass is removed from the fermentation broth and discarded. A base such as, for example, sodium, potassium or ammonium hydroxide is used to adjust a pH of between 9 to 11. The mineral constituents (inorganic salts) are removed from the broth after concentration and cooling by crystallization and either used as fertilizers or discarded.

In processes for producing lysine using the bacteria according to one embodiment, processes resulting in products which comprise components of the fermentation broth are also employed. These are used in particular as animal feed additives.

Depending on requirements, the biomass can be removed wholly or partly from the fermentation broth by separation methods such as, for example, centrifugation, filtration, decantation or a combination thereof, or be left completely therein. Where appropriate, the biomass or the biomass-containing fermentation broth is inactivated during a suitable process step, for example by thermal treatment (heating) or by addition of acid.

The chemical constituents of the biomass are inter alia the cell envelope, for example the peptidoglycan and the arabinogalactan, the protein or polypeptide, for example the 2-methylcitrate dehydratase polypeptide, lipids and phospholipids and nucleic acids (DNA and RNA), for example polynucleotides comprising the mutation according to the invention. As a result of the measures of inactivation and/or of the further process steps (for example acidification, spray drying, granulation etc.), nucleic acids are preferably present as fragments with a length of inter alia $\geq$40-60 bp, >60-80 bp, >80-100 bp, >100-200 bp, >200-300 bp, >300-400 bp, >400-500 bp, >500-750 bp, >750-1000 bp, >1000-1250 bp, >1250-1500 bp, >1500-1750 bp, >1750-2000 bp, >2000-2500 bp, >2500-3000 bp, >3000-4000 bp, >4000-5000 bp.

In one procedure, the biomass is removed completely or almost completely so that no (0%) or not more than 30%, not more than 20%, not more than 10%, not more than 5%, not more than 1% or not more than 0.1% biomass remains in the product produced. In a further procedure, the biomass is not removed, or is removed only in small proportions, so that all (100%) or more than 70%, 80%, 90%, 95%, 99% or 99.9% biomass remains in the product produced. In one aspect of the invention, the biomass is removed in proportions $\geq$0% to $\leq$100%.

Fermentation broth obtained after the fermentation can be adjusted, before or after the complete or partial removal of the biomass, to an acidic pH with an inorganic acid such as, for example, hydrochloric acid, sulphuric acid or phosphoric acid or organic acid such as, for example, propionic acid (GB 1,439,728 or EP 1 331 220). It is possible to acidify the fermentation broth with the complete content of biomass (U.S. Pat. No. 6,340,486 or U.S. Pat. No. 6,465,025). The broth can also be stabilized by adding sodium bisulphite ($NaHSO_3$, GB 1,439,728) or another salt, for example ammonium, alkali metal or alkaline earth metal salt of sulphurous acid.

During the removal of the biomass, organic or inorganic solids present where appropriate in the fermentation broth are partially or completely removed. The organic by-products dissolved in the fermentation broth and the dissolved unconsumed components of the fermentation medium (starting materials) remain at least partly (>0%), preferably to the extent of at least 25%, preferably to the extent of at least 50% and more preferably to the extent of at least 75% in the product. Where appropriate, they also remain completely (100%) or almost completely, meaning >95% or >98%, in the product. In this sense, the term "based on fermentation broth" means that the product comprises at least part of the components of the fermentation broth.

Subsequently, water is removed or thickened or concentrated from the broth by known methods such as, for example, with the aid of a rotary evaporator, thin-film evaporator, falling film evaporator, by reverse osmosis or by nanofiltration. This concentrated fermentation broth can then be worked up to free-flowing products, in particular to a fine-particle powder or preferably coarse granules, by methods of freeze drying, of spray drying, of spray granulation or by other processes as described for example in the circulating fluidized bed according to PCT/EP2004/006655. A desired product is isolated where appropriate from the resulting granules by screening or dust removal.

It is likewise possible to dry the fermentation broth directly, i.e. without previous concentration by spray drying or spray granulation.

"Free-flowing" means powders which flow unimpeded out of a series of glass orifice vessels with orifices of different sizes at least out of the vessel with a 5 mm (millimetres) orifice (Klein: Seifen, Öle, Fette, Wachse 94, 12 (1968)).

"Fine-particle" means a powder predominantly (>50%) of a particle size of diameter from 20 to 200 μm.

"Coarse" means a product predominantly (>50%) of a particle size of diameter from 200 to 2000 μm.

The particle size determination can be carried out by methods of laser diffraction spectrometry. Corresponding methods are described in the textbook on "Teilchengrößenmessung in der Laborpraxis" by R. H. Müller and R. Schuhmann, Wissenschaftliche Verlagsgesellschaft Stuttgart (1996) or in the textbook "Introduction to Particle Technology" by M. Rhodes, published by Wiley & Sons (1998).

The free-flowing, fine-particle powder can in turn be converted by suitable compaction or granulation processes into a coarse, very free-flowing, storable and substantially dust-free product.

The term "dust-free" means that the product comprises only small proportions (<5%) of particle sizes below 100 μm in diameter.

"Storable" in the sense of this invention means a product which can be stored for at least one (1) year or longer, preferably at least 1.5 years or longer, particularly preferably two (2) years or longer, in a dry and cool environment without any substantial loss (<5%) of the respective amino acid occurring.

In one aspect of the invention, a process for producing an L-amino acid, preferably L-lysine or L-tryptophan, containing product, preferably animal feed additive, from fermentation broths, comprises:
a) culturing and fermentation of an L-amino acid-secreting coryneform bacterium which comprises at least one prpD1 allele which codes for a polypeptide having 2-methylcitrate dehydratase activity, which comprises an amino acid sequence in which at position 272 or the comparable position a proteinogenic amino acid except L-proline, preferably L-leucine, is present, in a fermentation medium,
b) removal of the biomass formed during the fermentation in an amount of from 0 to 100% by weight, and
c) drying of the fermentation broth obtained as in a) and/or b) in order to obtain the product in the desired powder or granular form,
where an acid selected from the group consisting of sulphuric acid, phosphoric acid or hydrochloric acid is added where appropriate before step b) or c). Step a) or b) is preferably followed by removal of water from the L-amino acid-containing fermentation broth (concentration).

In another embodiment, a process for producing a lysine sulphate-containing product is described in principle in DE 102006016158, and in which the fermentation broth obtained using the microorganisms according to the invention, from which the biomass has been removed completely or partly where appropriate, is further processed by carrying out a process which comprises at least the following steps:
a) the pH is reduced by adding sulphuric acid to 4.0 to 5.2, in particular 4.9 to 5.1, and a molar sulphate/L-lysine ratio of from 0.85 to 1.2, preferably 0.9 to 1.0, particularly preferably >0.9 to <0.95, is adjusted in the broth, where appropriate by adding a further or a plurality of sulphate-containing compound(s) and
b) the mixture obtained in this way is concentrated by removal of water, and granulated where appropriate,
where one or both of the following measures is/are carried out where appropriate before step a):
c) measurement of the molar sulphate/L-lysine ratio to ascertain the required amount of sulphate-containing compound(s)
d) addition of a sulphate-containing compound selected from the group of ammonium sulphate, ammonium bisulphate and sulphuric acid in appropriate ratios.

Where appropriate, also before step b), a salt of sulphurous acid, preferably alkali metal bisulphite, more preferably sodium bisulphit, is added in a concentration of 0.01 to 0.5 by weight, preferably 0.1 to 0.3% by weight, more preferably 0.1 to 0.2% by weight, based on the fermentation broth.

Preferred sulphate-containing compounds which should be mentioned in the context of the abovementioned process steps are ammonium sulphate and/or ammonium bisulphate or corresponding mixtures of ammonia and sulphuric acid and sulphuric acid itself.

The molar sulphate/L-lysine ratio V is calculated by the formula: $V=2\times[SO_4^{2-}]/[L\text{-lysine}]$. This formula takes account of the fact that the $SO_4^{2-}$ anion has two charges. A ratio of V=1 means that the stoichiometric composition $Lys_2(SO_4)$ is present, whereas the finding with a ratio of V=0.9 is a 10% sulphate deficit and with a ratio of V=1.1 is a 10% sulphate excess.

The organic or inorganic auxiliaries or carriers such as starch, gelatin, cellulose derivatives or similar substances, as used in the processing of food products or feeds as binders, gelling agents or thickeners, or further substances such as, for example, silicas, silicates (EP0743016A) stearates may be used during the granulation or compaction.

The surface of the resulting granules may be provided with oils as described in WO 04/054381. Oils which can be used are mineral oils, vegetable oils or mixtures of vegetable oils. Examples of such oils are soya oil, olive oil, soya oil/lecithin mixtures. In the same way, silicone oils, polyethylene glycols or hydroxyethylcellulose are also suitable. Treatment of the surfaces with the said oils achieves an increased abrasion resistance of the product and a reduction in the dust content. The oil content in the product is 0.02 to 2.0% by weight, preferably 0.02 to 1.0% by weight, and more preferably 0.2 to 1.0% by weight based on the total amount of the feed additive.

Preferred products have a proportion of ≧97% by weight of a particle size of from 100 to 1800 μm or a proportion of ≧95% by weight of a particle size of from 300 to 1800 μm diameter. The proportion of dust, i.e. particles with a particle size <100 μm, is preferably >0 to 1% by weight, more preferably not exceeding 0.5% by weight.

However, alternatively, the product may also be absorbed on an organic or inorganic carrier known in the processing of feeds, such as, for example, silicas, silicates, meals, brans, flours, starches, sugars or others, and/or be mixed and stabilized with customary thickeners and binders. Examples of use and processes therefor are described in the literature (Die Mühle+Mischfuttertechnik 132 (1995) 49, page 817).

The product can also be brought by coating processes with film-formers such as, for example, metal carbonates, silicas, silicates, alginates, stearates, starches, gums and cellulose ethers as described in DE-C-4100920 to a state in which the product is stable to digestion by animal stomachs, for example, the stomach of ruminants.

To adjust a desired amino acid concentration in the product it is possible, depending on requirements, to add the appropriate amino acid during the process in the form of a concentrate or, if appropriate, of a substantially pure substance or its salt in liquid or solid form. These can be added singly or as mixtures to the resulting or concentrated fermentation broth, or else during the drying or granulation process.

In another embodiment, a process for producing a solid lysine-containing product as described in principle in US 20050220933, and which comprises the working up of the fermentation broth obtained using microorganisms according to the invention, in the following steps:

a) filtration of the fermentation broth, preferably with a membrane filter, to result in a biomass-containing sludge and a filtrate,
b) concentration of the filtrate, preferably so as to result in a solids content of from 48 to 52% by weight,
c) granulation of the concentrate obtained in step b), preferably at a temperature of from 50° C. to 62° C., and
d) coating of the granules obtained in c) with one or more of the coating agent(s)

The coating agents used for the coating in step d) are preferably selected from the group consisting of
  d1) the biomass obtained in step a),
  d2) an L-lysine-containing compound, preferably selected from the group of L-lysine hydrochloride or L-lysine sulphate,
  d3) a substantially L-lysine-free substance with an L-lysine content of <1% by weight, preferably <0.5% by weight, preferably selected from the group of starch, carageenan, agar, silicas, silicates, meals, brans and flours, and
  d4) a water-repellant substance, preferably selected from the group of oils, polyethylene glycols and liquid paraffins.

In the case of lysine, the ratio of the ions during the production of lysine-containing products is preferably adjusted so that the equivalent ion ratio corresponding to the following formula $$2\times[SO_4^{2-}]+[Cl^-]-[NH_4^+]-[Na^+]-[K^+]-2\times[Mg^{2+}]-2\times[Ca^{2+}]/[L\text{-}Lys]$$

results in 0.68 to 0.95, preferably 0.68 to 0.90, as described by Kushiki et al. in US 20030152633 (the molar concentrations are to be given in the "[ ]").

In case of lysine, the solid product produced in this way has, based on the fermentation broth, a lysine content (as lysine base) of 10% by weight to 70% by weight or 20% by weight to 70% by weight, preferably 30% by weight to 70% by weight and more preferably of 40% by weight to 70% by weight, based on the dry matter of the product. Maximum contents of lysine base of 71% by weight, 72% by weight, 73% by weight are possible.

In case of an electrically neutral amino acid such as L-tryptophan, the solid product produced in this way has, based on the fermentation broth, an amino acid content of at least 5% by weight, 10% by weight, 20% by weight, 30% by weight and at most 50% by weight, 60% by weight, 70% by weight, 80% by weight, 90% by weight or up to 95% by weight.

The water content of the solid product is up to 5% by weight, preferably up to 4% by weight, and more preferably less than 3% by weight.

In another embodiment, an L-lysine-containing feed additive based on fermentation broth exhibits the following features
  a) a lysine content (as base) of at least 10% by weight up to a maximum of 73% by weight,
  b) a water content not exceeding 5% by weight, and
  c) a biomass content corresponding to at least 0.1% of the biomass present in the fermentation broth, where the biomass, inactivated where appropriate, is formed by coryneform bacteria according to the invention.

In another embodiment, an L-tryptophan-containing feed additive based on fermentation broth exhibits the following features
  a) a tryptophan content of at least 5% by weight up to a maximum of 95% by weight,
  b) a water content not exceeding 5% by weight, and
  c) a biomass content corresponding to at least 0.1% of the biomass present in the fermentation broth, where the biomass, inactivated where appropriate, is formed by coryneform bacteria according to the invention.

The strain MH20-22B was deposited on 28 Oct. 2004 at the Deutsche Sammlung für Mikroorganismen and Zellkulturen (DSMZ, Brunswick, Germany) as DSM 16835.

The *Corynebacterium glutamicum* mutant DM1916 comprises L-leucine at position 272 of the amino acid sequence of the PrpD1 polypeptide was deposited on 15 May 2006 at the Deutsche Sammlung für Mikroorganismen and Zellkulturen (DSMZ, Brunswick, Germany) as DSM 18258.

The present invention is explained in more detail below by means of exemplary embodiments.

EXAMPLE 1

Mutagenesis of the L-Lysine-Producing Strain DM416

The *Corynebacterium glutamicum* strain DM416 was employed as starting strain for the mutagenesis with N-methyl-N'-nitro-N-nitrosoguanidine (MNNG). The strain DM416 is a homoserine- and leucine-requiring mutant of *Corynebacterium glutamicum* and is deposited under the designation ATCC21543 at the American Type Culture Collection (Manassas, Va., USA).

The strain DM416 was cultured in 10 ml of LB broth (Merck, Darmstadt, Germany) which were present in a 100 ml Erlenmeyer flask at 33° C. and 200 rpm on an orbital shaker of the Certomat BS-1 type (B. Braun Biotech International, Melsungen, Germany) for 24 hours. The culture was then centrifuged, the sediment was resuspended in 10 ml of 0.9% NaCl solution, the resulting suspension was again centrifuged, and the resulting sediment was taken up in 10 ml of 0.9% NaCl solution. 5 ml of this cell suspension were treated with 400 μg/ml MNNG at 30° C. and 200 rpm on a shaker (see above) for 15 minutes. The mutagenesis mixture was then centrifuged and the sediment was taken up in 10 ml of 2% Na thiosulphate in 0.9% NaCl buffer (pH=6.0). The cell suspension was then diluted in the ratio 1:1000, 1:10 000 and 1:100 000 with 0.9% NaCl solution, and aliquots were plated on brain-heart agar (Merck, Darmstadt, Germany). Approximately 4000 mutants were isolated in this way.

EXAMPLE 2

Output Test on the Mutants of the Strain DM416

The mutants obtained in Example 1 were cultured in a nutrient medium suitable for producing lysine and the lysine content in the culture supernatant was determined.

For this purpose, the clones were initially grown on brain-heart agar plates (Merck, Darmstadt, Germany) at 33° C. for 24 hours. A preculture was inoculated (10 ml of medium in 100 ml Erlenmeyer flask) starting from each of these agar plate cultures. The medium used for the preculture was the MM medium. The preculture was incubated at 33° C. and 240 rpm on a shaker for 24 hours. A main culture was inoculated from this preculture in such a way that the initial OD (660 nm) of the main culture was 0.1 OD. The MM medium was likewise used for the main culture.

| MM medium | |
| --- | --- |
| CSL | 5 g/l |
| MOPS | 20 g/l |
| Glucose (autoclaved separately) | 50 g/l |
| Salts: | |
| $(NH_4)_2SO_4)$ | 25 g/l |
| $KH_2PO_4$ | 0.1 g/l |
| $MgSO_4 * 7H_2O$ | 1.0 g/l |
| $CaCl_2 * 2H_2O$ | 10 mg/l |
| $FeSO_4 * 7H_2O$ | 10 mg/l |
| $MnSO_4 * H_2O$ | 5.0 mg/l |
| Biotin (sterilized by filtration) | 0.3 mg/l |
| Thiamine * HCl (sterilized by filtration) | 0.2 mg/l |
| L-Leucine (sterilized by filtration) | 0.2 g/l |
| L-Homoserine (sterilized by filtration) | 0.2 g/l |
| $CaCO_3$ | 25 g/l |

CSL (corn steep liquor), MOPS (morpholinopropanesulphonic acid) and the salt solution were adjusted to pH 7 with aqueous ammonia and autoclaved. The sterile substrate and vitamin solutions, and the dry autoclaved $CaCO_3$ were then added.

The culturing took place in volumes of 10 ml which were present in 100 ml Erlenmeyer flasks with baffles. The temperature was 33° C., the number of revolutions was 250 rpm and the humidity was 80%.

After 24 hours, the optical density (OD) at a measurement wavelength of 660 nm was determined using a Biomek 1000 (Beckmann Instruments GmbH, Munich, Germany). The amount of lysine formed was determined using an amino acid analyser from Eppendorf-BioTronik (Hamburg, Germany) by ion exchange chromatography and post-column derivatization with ninhydrin detection. A mutant distinguished by increased formation of lysine was called DM1916.

TABLE 1

| Strain | OD (660) | Lysine HCl (g/l) |
| --- | --- | --- |
| DM416 | 6.3 | 1.43 |
| DM1916 | 6.3 | 1.61 |

EXAMPLE 3

Sequencing of the prpD1 Allele of the Mutant DM1916

Chromosomal DNA was isolated from the clone DM1916 by the method of Eikmanns et al. (Microbiology 140: 1817-1828 (1994)). The polymerase chain reaction was used to amplify a DNA segment which harbours the prpD1 gene or allele. On the basis of the known sequence of the prpD1 gene for *C. glutamicum* (sequence No. 770 from EP1108790), the following primer oligonucleotides were selected for the PCR:

```
prpD1_XL_A1 (SEQ ID NO: 9):
5' gcgaattcta aactgcgtga ggttgtgg 3' prpD1_XL_A2 (SEQ ID NO: 10):
5' gcgaattctc cccacatcaa caccattc 3'
```

The depicted primers were synthesized by MWG Biotech (Ebersberg, Germany) and the PCR reaction was carried out by the standard PCR method of Innis et al. (PCR Protocols. A Guide to Methods and Applications, 1990, Academic Press). The primers make it possible to amplify a DNA segment which is about 1.63 kb in length and which harbours the prpD1 gene or allele. In addition, the primers contain the sequence for a cleavage site of the restriction endonuclease EcoRI, which is marked by underlining in the nucleotide sequence depicted above.

The amplified DNA fragment which has a length of about 1.63 kb and which harbours the prpD1 allele of the strain DM1916 was identified by electrophoresis in a 0.8% agarose gel, isolated from the gel and purified by conventional methods (QIAquick Gel Extraction Kit, Qiagen, Hilden).

The nucleotide sequence of the amplified DNA fragment or PCR product was ascertained by sequencing by Agowa (Berlin, Germany). The sequence of the PCR product is depicted in SEQ ID NO: 13. The sequence of the coding region is additionally depicted in SEQ ID NO: 5. The amino acid sequence of the relevant methylcitrate dehydratase protein which was obtained with the aid of the Patentin program is depicted in SEQ ID NO: 6.

The base thymine is located at position 815 of the nucleotide sequence of the coding region of the prpD1 allele of the strain DM1916 (SEQ ID NO: 5). The base cytosine is located at the corresponding position of the wild-type gene (SEQ ID NO: 1).

The amino acid leucine is located at position 272 of the amino acid sequence of the methylcitrate dehydratase protein of strain DM1916 (SEQ ID NO: 6). The amino acid proline is located at the corresponding position of the wild-type protein (SEQ ID NO: 2).

The prpD1 allele which comprises the base thymine at position 815 of the coding region, and accordingly codes for a methylcitrate dehydratase protein which comprises the amino acid leucine at position 272 of the amino acid sequence, is referred to hereinafter as prpD1_P272L allele. In the designation "prpD1_P272L" P stands for L-proline, L for L-leucine and 272 indicates the position of the amino acid exchange (see SEQ ID NO: 2 and 6).

The *Corynebacterium glutamicum* mutant DM1916 which comprises L-leucine at position 272 of the amino acid sequence of the PrpD1 polypeptide was deposited on 15 May 2006 at the Deutsche Sammlung für Mikroorganismen and Zellkulturen (DSMZ, Brunswick, Germany) as DSM 18258.

EXAMPLE 4

Exchange of the prpD1 Wild-Type Gene of Strain DM416 for the prpD1_P272L Allele 4.1 Construction of the Exchange Vector pK18mobsacB_prpD1_P272L The DNA fragment which has a length of about 1.63 kb, which harbours the prpD1_P272L allele and which was prepared by PCR and described in Example 3 was incorporated by exchange mutagenesis with the aid of the sacB system described in Schäfer et al. (Gene, 14, 69-73 (1994)) into the chromosome of the *C. glutamicum* strain DM416 described in Example 1. This system makes it possible to produce and select allele exchanges accomplished by homologous recombination.

For this purpose the prpD1_P272L fragment about 1.63 kb in size was cleaved with the restriction endonuclease EcoRI, identified by electrophoresis in a 0.8% agarose gel and then isolated from the gel and purified by conventional methods (QIAquick Gel Extraction Kit, Qiagen, Hilden).

The mobilizable cloning vector pK18mobsacB was digested with the restriction enzyme EcoRI, and the ends were dephosphorylated with alkaline phosphatase (Alkaline Phosphatase, Boehringer Mannheim, Germany). The vector prepared in this way was mixed with the approx. 1.63 kb prpD1_P272L fragment, and the mixture was treated with T4-DNA ligase (Amersham-Pharmacia, Freiburg, Germany).

The *E. coli* strain S17-1 (Simon et al., Bio/Technology 1: 784-791, 1993) was then transformed with the ligation mixture (Hanahan, In. DNA Cloning. A Practical Approach. Vol. 1, ILR-Press, Cold Spring Harbor, N.Y., 1989). Selection of the plasmid-harbouring cells took place by plating out the transformation mixture on LB agar (Sambrook et al., Molecular Cloning: A Laboratory Manual. 2nd Ed., Cold Spring Harbor, N.Y., 1989) which was supplemented by 25 mg/l kanamycin.

Plasmid DNA was isolated from a transformant with the aid of the QIAprep Spin Miniprep Kit from Qiagen and examined by restriction cleavage with the enzyme PstI and subsequent agarose gel electrophoresis. The plasmid is called pK18mobsacB_prpD1_P272L and is depicted in the FIGURE.

4.2 Allele Exchange

The vector pK18mobsacB_prpD1_P272L mentioned in Example 4.1 was transferred by a protocol of Schäfer et al. (Journal of Microbiology 172: 1663-1666 (1990)) into the *C. glutamicum* strain DM416 by conjugation. The vector is not capable of independent replication in DM416 and remains in the cell only if it is integrated into the chromosome as the result of a recombination event. Selection of transconjugants, i.e. of clones with integrated pK18mobsacB_prpD1_P272L took place by plating out the conjugation mixture on LB agar (Sambrook et al., Molecular Cloning: A Laboratory Manual. 2nd Ed. Cold Spring Harbor, N.Y., 1989) which was supplemented with 15 mg/l kanamycin and 50 mg/l nalidixic acid. Kanamycin-resistant transconjugants were streaked onto LB agar plates with 25 mg/l kanamycin and incubated at 33° C. for 24 hours. Mutants in which the plasmid had been excised as the result of a second recombination event were selected by culturing the clones nonselectively in LB liquid medium for 30 hours, followed by streaking on LB agar with 10% sucrose and incubating for 16 hours.

The plasmid pK18mobsacB_prpD1_P272L comprises, just like the initial plasmid pK18mobsacB, besides the kanamycin-resistance gene a copy of the sacB gene which codes for the laevan sucrase from *Bacillus subtilis*. The sucrose-inducible expression leads to the formation of laevan sucrase which catalyses the synthesis of the product laevan which is toxic for *C. glutamicum*. Thus, the only clones to grow on LB agar with sucrose are those in which the integrated pK18mobsacB_prpD1_P272L has excised as a result of a second recombination event. Depending on the position of the second recombination event in relation to the site of mutation, the allele exchange or incorporation of the mutation takes place on excision, or the original copy remains in the host's chromosome.

Approximately 40 to 50 colonies were tested for the phenotype "growth in the presence of sucrose" and "no growth in the presence of kanamycin". For 4 colonies which exhibited the phenotype "growth in the presence of sucrose" and "no growth in the presence of kanamycin", a region of the prpD1 gene covering the P272L mutation and starting from the sequencing primer pr1-2 (corresponds to nucleotide sequence position 424-443 of the coding region of the prpD1 gene from SEQ ID NO: 1) was sequenced by Agowa (Berlin, Germany) in order to demonstrate that the mutation of the prpD1_P272L allele is present in the chromosome. The primer pr1-2 used was synthesized by Agowa for this purpose:

```
pr1-2:
5' ggt atc gcc act gcc tat ga 3'
```

A clone which contains the base thymine at position 815 of the coding region of the prpD1 gene, and thus has the prpD1_P272L allele, was identified in this way. This clone is called the DM416prpD1_P272L strain.

EXAMPLE 6

Comparison of the Output of the DM416prpD1_P272L Strain with that of the Starting Strain DM416

The output test on the *C. glutamicum* strain DM416prpD1_P272L obtained in Example 5 was carried out as described in Example 2. The result of the test is depicted in Table 2.

TABLE 2

| Strain | OD (660 nm) | Lysine HCl g/l |
|---|---|---|
| DM416 | 6.2 | 1.40 |
| DM416prpD1_P272L | 6.2 | 1.64 |

The abbreviations and designations used have the following meaning. The stated base pair numbers are approximations obtained within the scope of the reproducibility of measurements.

| | |
|---|---|
| Kan: | kanamycin-resistance gene |
| EcoRI: | cleavage site of the restriction enzyme EcoRI |
| PstI: | cleavage site of the restriction enzyme PstI |
| prpD1: | prpD1_P272L allele |
| sacB: | sacB gene |
| RP4-mob: | mob region with the origin of replication for transfer (oriT) |
| oriV: | origin of replication V |

German patent application 102006050489.5, filed Oct. 26, 2006, is incorporated herein by reference.

Numerous modifications and variations on the present invention are possible in light of the above teachings. It is therefore to be understood that within the scope of the appended claims, the invention may be practiced otherwise than as specifically described herein.

The invention claimed is:

1. A process for producing an L-amino acid, comprising:
   a) fermenting an isolated coryneform bacterium in a suitable medium, wherein the bacterium comprises at least one copy of a gene which encodes for a polypeptide having 2-methylcitrate dehydratase activity, wherein the polypeptide comprises the amino acid sequence of SEQ ID NO: 2 except that one of the proteinogenic amino acids other than L-proline is present at position 272 or at a corresponding or comparable position; or wherein said polypeptide comprises an amino acid sequence at least 90% identical to SEQ ID NO: 6 or SEQ ID NO: 8 except that one of the proteinogenic amino acids other than L-proline is present at position 272 or at a corresponding or comparable position, and
   b) accumulating the L-amino acid in the fermentation medium or inside the bacterial cells.

2. The process according to claim 1, wherein the isolated coryneform bacterium is an isolated mutant of coryneform bacteria comprising a gene which encodes a polypeptide having 2-methylcitrate dehydratase activity, wherein the polypeptide comprises an amino acid sequence in which one of proteinogenic amino acids, except L-proline, is present at position 272 of SEQ ID NO: 2 or a corresponding or comparable position.

3. The process according to claim 1, wherein the isolated coryneform bacterium is a recombinant coryneform bacterium which comprises an isolated polynucleotide encoding a polypeptide having a 2-methylcitrate dehydratase enzymic activity, said polypeptide comprises L-leucine at position 272 of SEQ ID NO: 6 or SEQ ID NO: 8 or a corresponding or comparable position.

4. The process according to claim 1, wherein the L-amino acid is isolated or collected.

5. The process according to claim 4, wherein the L-amino acid is purified.

6. The process according to claim 1, wherein the L-amino acid is isolated or collected together with constituents of the fermentation medium and/or of the biomass in an amount greater than 0% to 100%.

7. The process according to claim 1, further comprising:
   c) removing formed biomass in an amount of from 0 to 100% from the fermentation broth obtained in b), and
   d) producing a substantially dry and shaped product by granulation, compaction, spray drying and/or extrusion, from the fermentation broth obtained in c).

8. The process according to claim 7, wherein an acid selected from the group of sulphuric acid, hydrochloric acid and phosphoric acid is added to the fermentation broth before or after c).

9. The process according to claim 7, wherein water is removed from the resulting broth before or in c).

10. The process according to claim 7, wherein the shaped product obtained in or during d) is sprayed with an oil.

11. The process according to claim 1, further comprising:
    c) filtering the fermentation broth resulting in a biomass-containing sludge and a filtrate,
    d) concentrating the filtrate resulting in a solids content of from 48 to 52% by weight,
    e) granulating the concentrate obtained in d) at a temperature of from 50° C. to 62° C., and
    f) coating the granules obtained in e) with at least one coating agent.

12. The process according to claim 1, wherein the coryneform bacterium is selected from the group consisting of *Corynebacterium efficiens, Corynebacterium glutamicum, Corynebacterium thermoaminogenes* and *Corynebacterium aminogenes*.

13. The process according to claim 1, wherein said bacterium is at least one *Corynebacterium glutamicum* bacterium.

14. The process according to claim 1, wherein said bacterium is L-amino acid-secreting bacterium.

15. The process according to claim 14, wherein said bacterium secrets L-lysine, L-valine, L-isoleucine, L-tryptophan or L-homoserine.

16. The process according to claim 1, wherein the encoded polypeptide comprises L-leucine at position 272 or a comparable position.

17. The process according to claim 1, wherein the encoded polypeptide comprises the amino acid sequence of SEQ ID NO: 2 having one of the proteinogenic amino acids, except L-proline, at position 272.

18. The process according to claim 1, wherein said gene comprises a nucleotide sequence which is identical to the nucleotide sequence of a polynucleotide which is obtainable by a polymerase chain reaction (PCR) using DNA obtained from a coryneform bacterium and using a primer pair consisting of a first primer comprising at least 15 consecutive nucleotides selected from the nucleotide sequence between position 1 and 750 of SEQ ID NO:3 or SEQ ID NO:7, and a second primer comprising at least 15 consecutive nucleotides selected from the complementary nucleotide sequence between position 3000 and 2245 of SEQ ID NO:3 or SEQ ID NO: 7.

19. The process according to claim 1, wherein the encoded polypeptide comprises an amino acid sequence having a length corresponding to 498 L-amino acids.

20. The process according to claim 1, wherein the encoded polypeptide comprises from position 252 to 291 of said amino acid sequence an amino acid sequence corresponding to position 252 to 291 of SEQ ID NO:6.

21. The process according to claim 1, wherein the encoded polypeptide comprises an amino acid sequence which is at least 90% identical to the amino acid sequence of SEQ ID NO:6.

22. The process according to claim 1, wherein the gene comprises a nucleotide sequence which is at least 90% identical to the nucleotide sequence of SEQ ID NO:5.

23. The process according to claim 16, wherein the encoded protein comprises an amino acid sequence selected from the group consisting of
   a) the amino acid sequence of SEQ ID NO:6,
   b) the amino acid sequence of SEQ ID NO:6 comprising at least one conservative amino acid exchange wherein the conservative amino acid exchanges do not affect position 272, and
   c) the amino acid sequence of SEQ ID NO:6 comprising at least one insertion or deletion of at least one amino acid wherein the insertions or deletions do not affect position 272.

24. The process according to claim 17, wherein the amino acid sequence of SEQ ID NO:2 comprises L-leucine at position 272.

25. The process according to claim 24, wherein the gene comprises the nucleotide sequence of SEQ ID NO:5 or SEQ ID NO:7.

* * * * *